(12) United States Patent
Yang et al.

(10) Patent No.: US 11,642,215 B2
(45) Date of Patent: May 9, 2023

(54) KIRIGAMI MODIFICATION OF BIOMEDICAL TISSUE REINFORCING MESHES AND MATRICES FOR EXPANSILE TWO-TO-THREE DIMENSIONAL CONVERSION

(71) Applicant: THE TRUSTEES OF THE UNIVERSITY OF PENNSYLVANIA, Philadelphia, PA (US)

(72) Inventors: Shu Yang, Blue Bell, PA (US); Suhail K. Kanchwala, Merion, PA (US); Randall D. Kamien, Philadelphia, PA (US); Eric Jablonka, Philadelphia, PA (US); Jason Christopher Jolly, Philadelphia, PA (US); Young-Joo Lee, Philadelphia, PA (US); Hyesung Cho, Philadelphia, PA (US); Michael Tanis, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 164 days.

(21) Appl. No.: 16/967,909

(22) PCT Filed: Feb. 6, 2019

(86) PCT No.: PCT/US2019/016842
§ 371 (c)(1),
(2) Date: Aug. 6, 2020

(87) PCT Pub. No.: WO2019/157048
PCT Pub. Date: Aug. 15, 2019

(65) Prior Publication Data
US 2021/0052367 A1    Feb. 25, 2021

Related U.S. Application Data

(60) Provisional application No. 62/643,973, filed on Mar. 16, 2018, provisional application No. 62/627,142, filed on Feb. 6, 2018.

(51) Int. Cl.
*A61F 2/12*  (2006.01)

(52) U.S. Cl.
CPC ........ *A61F 2/12* (2013.01); *A61F 2210/0004* (2013.01); *A61F 2210/0057* (2013.01); *A61F 2240/001* (2013.01); *A61F 2250/003* (2013.01)

(58) Field of Classification Search
CPC ................ A61F 2/12; A61F 2210/0004; A61F 2210/0057; A61F 2240/001; A61F 2250/003; A61F 2/00; A61G 2/0063
See application file for complete search history.

(56) References Cited

U.S. PATENT DOCUMENTS

| 8,506,582 B2 | 8/2013 | Kammerer et al. |
| 2002/0055701 A1 | 5/2002 | Fischell et al. |

(Continued)

*Primary Examiner* — Brian A Dukert
*Assistant Examiner* — Rebecca Lynee Zimmerman
(74) *Attorney, Agent, or Firm* — BakerHostetler

(57) ABSTRACT

Provided are intraoperative devices, the devices comprising a substrate having a plurality of discontinuous cuts formed therein, the plurality of discontinuous cuts being formed such that when the substrate is subjected to deformation, the substrate is capable of deformation beyond an initial state so as to achieve a first shaped three-dimensional state. Through design of the cut patterns in 2D, one can locally control the stretchability and elasticity within the substrate. The substrate can then be deformed into a 3D structure that can provide shape and support to reconstructed tissue in the desired regions while also minimizing operative time and cost. Also provided are related methods of using the disclosed devices; the devices can be used in autologous tissue donation procedures as well as prosthetic procedures.

19 Claims, 52 Drawing Sheets

(56) References Cited

U.S. PATENT DOCUMENTS

| | | |
|---|---|---|
| 2006/0030939 A1 | 2/2006 | Frank |
| 2011/0022171 A1 | 1/2011 | Richter et al. |
| 2012/0226352 A1 | 9/2012 | Becker |
| 2015/0223928 A1 | 8/2015 | Limem et al. |
| 2015/0351889 A1 | 12/2015 | Reddy et al. |
| 2020/0222177 A1* | 7/2020 | Paydar .................. A61F 2/12 |

* cited by examiner

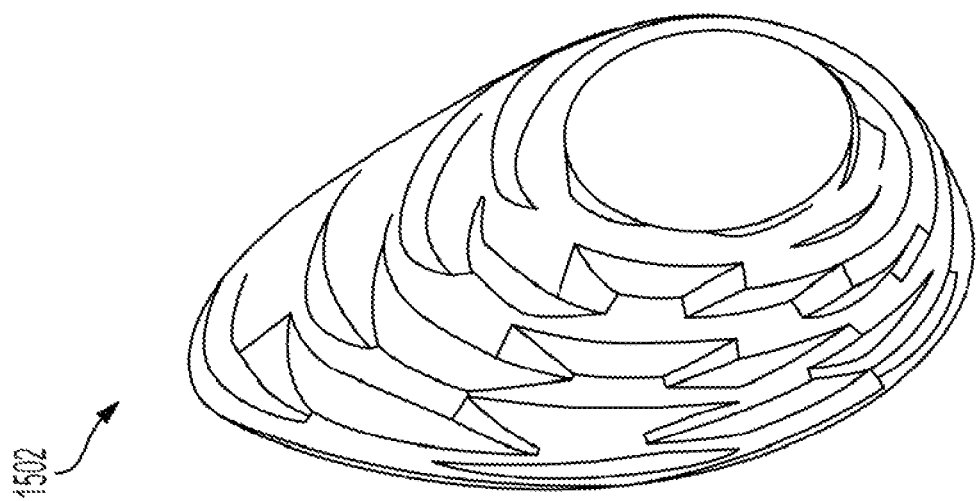
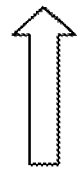
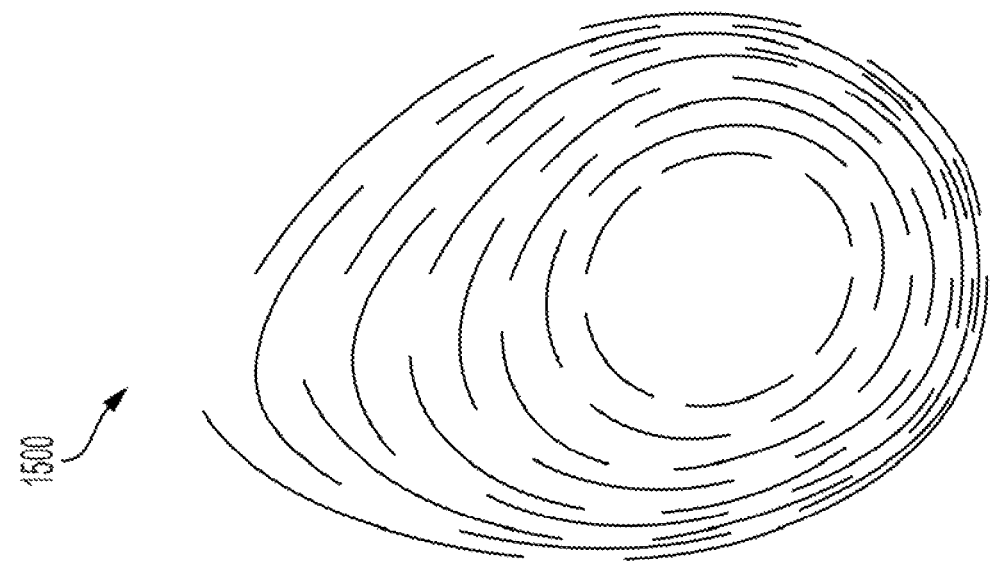
FIG. 15 ii) Circular shape
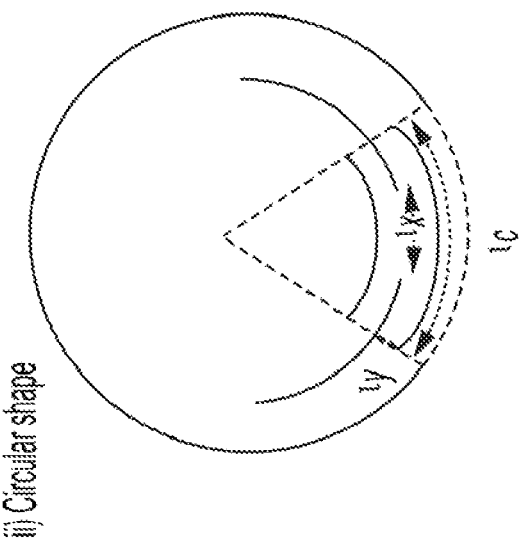
i) Rectangular shape
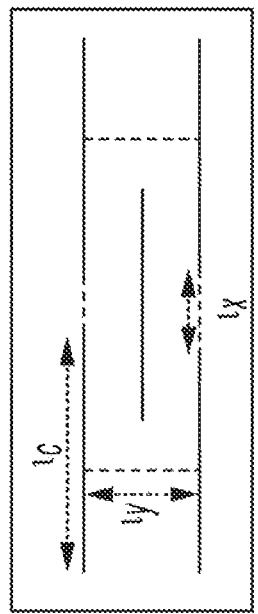
- Shape: Rectangular & Circular design
- Design parameters: $l_c/l_y$, $l_c/l_x$
  - ✓ $l_c/l_y = 10, 7, 4$  ($l_c/l_y = 10$ & $l_c/l_x = 3$ for previous design)
  - ✓ $l_c/l_x = 3, 2.5, 2$
- Tensile test: $E_{\text{eff}}$ & stretchability
- Material: Dupont™ Tyvek
FIG. 31 i) $\iota_C/\iota_y = 10, \iota_C/\iota_x = 3$
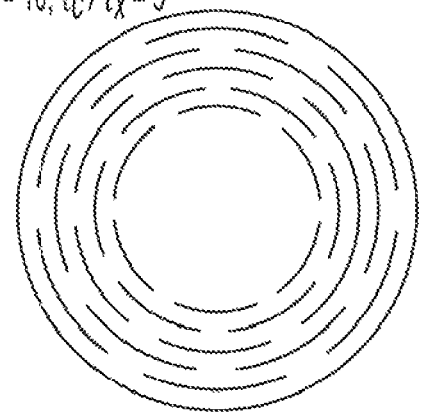
ii) $\iota_C/\iota_y = 7, \iota_C/\iota_x = 3$
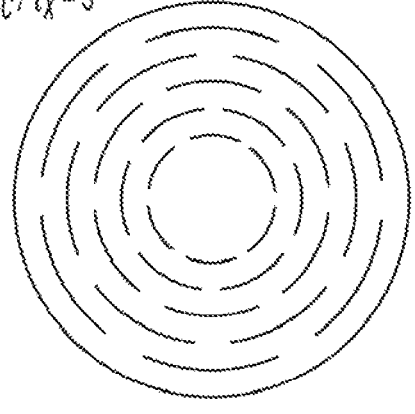
iii) $\iota_C/\iota_y = 10, \iota_C/\iota_x = 2.5$
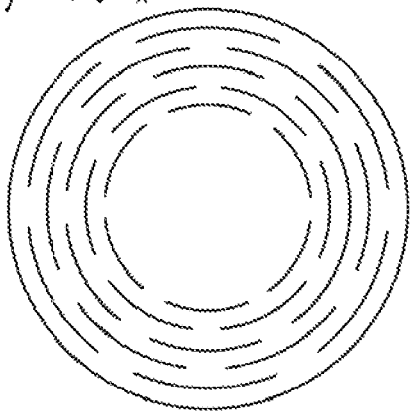
iv) $\iota_C/\iota_y = 7, \iota_C/\iota_x = 2.5$
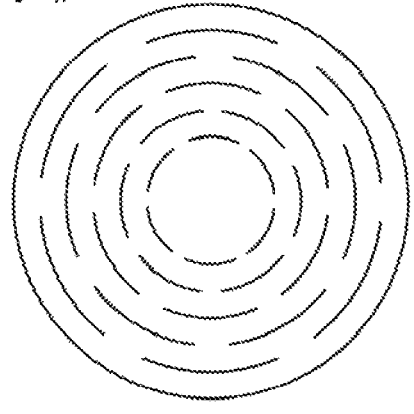
FIG. 35

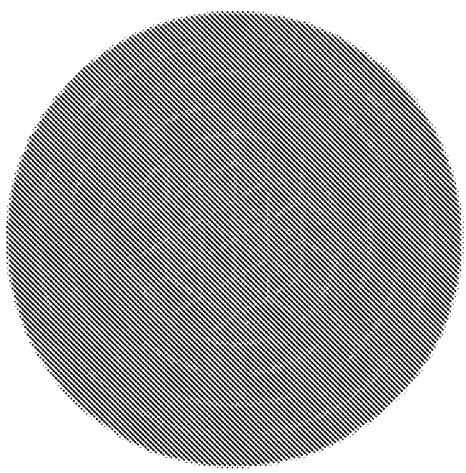
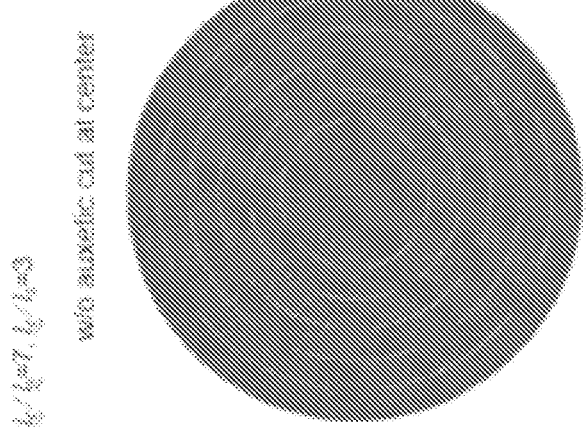
FIG. 42

○ Fractal cut: Improving stretchability/surface conformability
Level 1 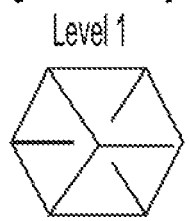  Level 2 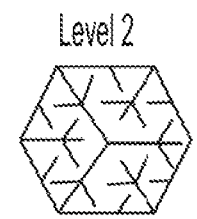
○ Releasing strain/stress concentration: Cut edge design modification
Sharp edge 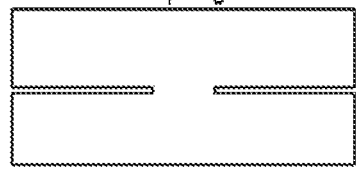  Blunt edge 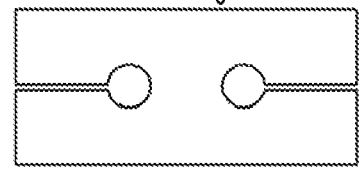
FIG. 45

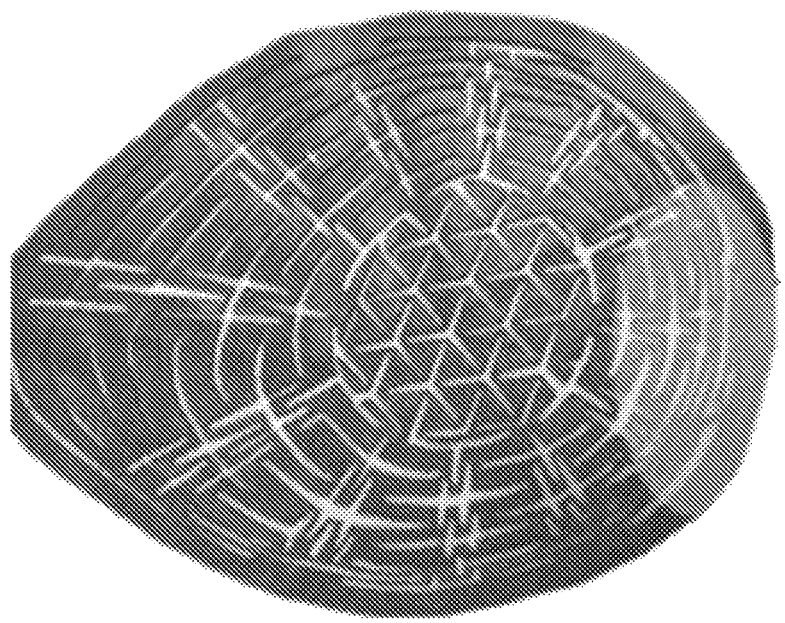
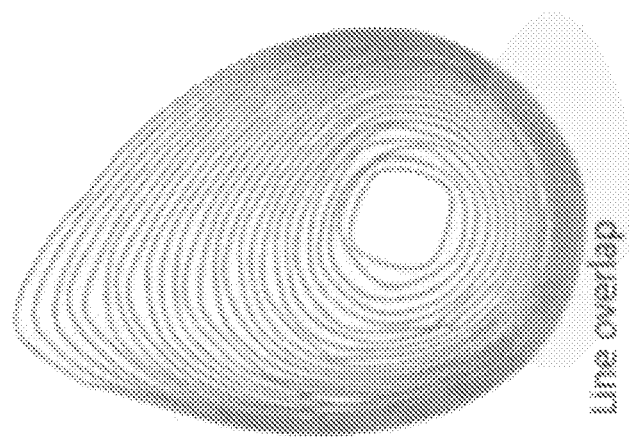
FIG. 47

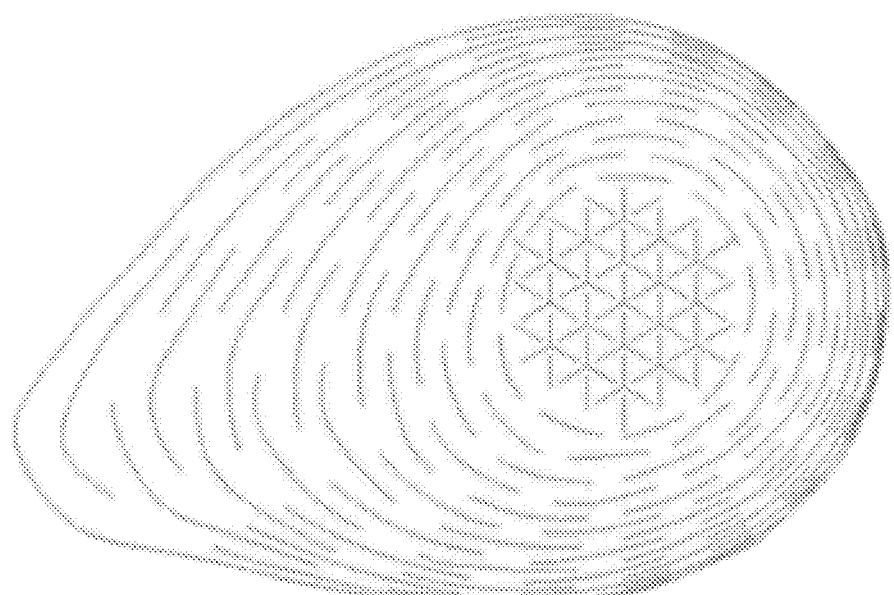
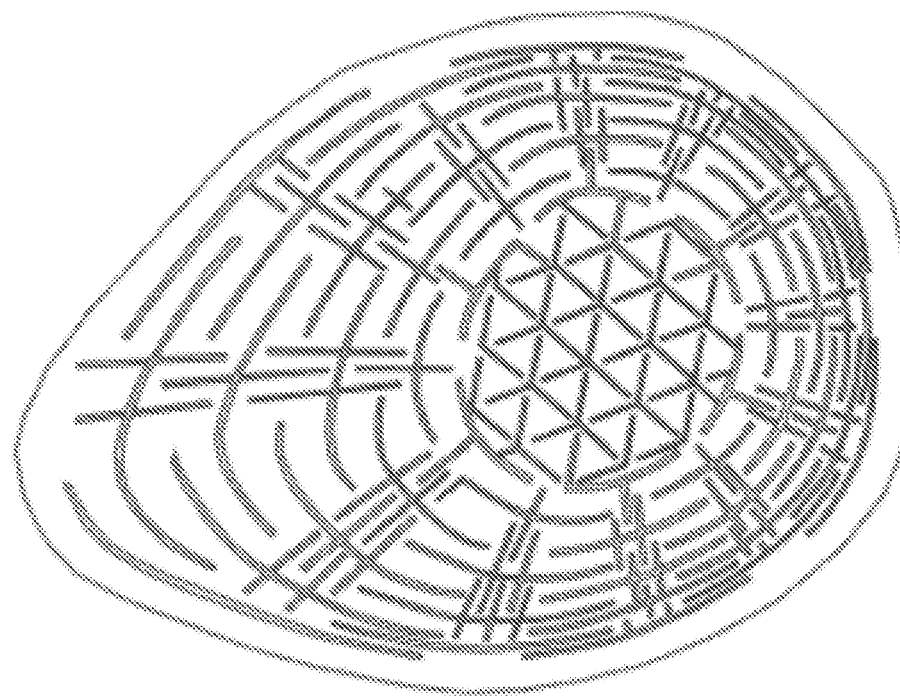
FIG. 48

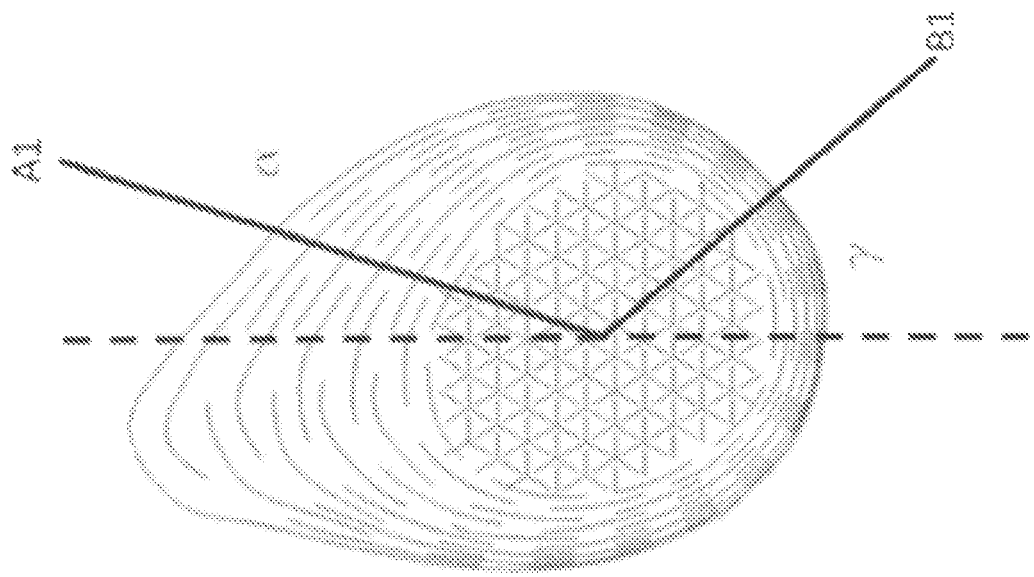
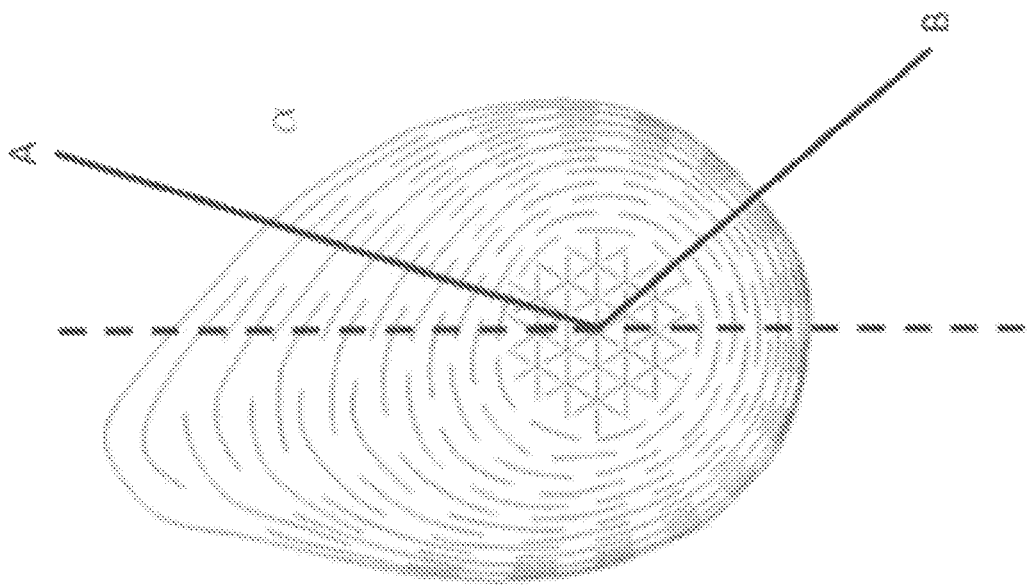
FIG. 49

KIRIGAMI MODIFICATION OF BIOMEDICAL TISSUE REINFORCING MESHES AND MATRICES FOR EXPANSILE TWO-TO-THREE DIMENSIONAL CONVERSION

CROSS-REFERENCE TO RELATED APPLICATIONS

This application is the National Stage Application of International Patent Application No. PCT/US2019/016842, filed Feb. 6, 2019, which claims priority to and the benefit of U.S. patent application No. 62/627,142, "Kirigami Breast Reconstruction Flap Wrap" (filed Feb. 6, 2018) and U.S. patent application no. 62/643,973, "Kirigami Modification Of Biomedical Tissue Reinforcing Meshes And Matrices For Expansile Two-To-Three Dimensional Conversion" (filed Mar. 16, 2018), the entireties of which foregoing applications are incorporated herein by reference for any and all purposes.

TECHNICAL FIELD

The present disclosure relates to the field of intraoperative surgical support devices, in particular to the field of such devices used in the field of reconstructive breast surgery.

BACKGROUND

Many thousands of women are diagnosed with breast cancer each year in the United States; with these numbers climbing due to better detection/screening and patient education. In addition, as a result of genetic screening of high risk individuals, many women who are identified to carry genetic mutations that leave them prone to developing breast cancer in the future will elect to have their breasts removed prophylactically. Many of these women will elect to pursue some form of breast reconstruction.

Currently, there are two main forms of breast reconstruction: implants and autologous tissue transfer. The most common form of breast reconstruction performed is implant-based breast reconstruction; making up 80% of the breast reconstructions performed.

To assist plastic surgeons in completing a successful and aesthetically pleasing breast reconstruction (whether it is implant-based or autologous tissue transfer), tissue reinforcing products are widely utilized across the world to achieve such results. Particularly, acellular dermal matrices (ADM) (e.g., Alloderm™, AlloMax™, FlexHD™). Such materials are sheets of skin processed in such a way to make them biocompatible for implantation. They can be used to create slings/pockets to keep breast implants or autologous tissue transfer secured against the chest wall in the desired shape/location to recreate a breast mound. These products are lucrative for their manufacturers and are commonly used by breast reconstruction surgeons.

Autologous breast reconstruction is an important but also labor-intensive procedure, as shaping of tissue transferred to the chest can require many operative hours to achieve an acceptable cosmetic result. At present, most plastic surgeons performing such procedures rely only on single sutures to shape flat blocks of transferred tissue into the more complex anatomic shape of a breast. These sutures, however, are often insufficient to hold the tissue in place for long periods, and the desired shape of the transferred tissue is ultimately lost. Further, even after a surgeon's meticulous work, the patient may not be content with the cosmetic outcome. As a result, a return to the operating room for revisions is common for many patients, leading to stress for the patient and also to stress for the patient's care team.

Accordingly, there is a long-felt need in the art for technology that would improve autologous breast reconstruction, breast implant procedures, and other surgical procedures.

SUMMARY

In meeting the described long-felt needs, the present disclosure first provides intraoperative devices, comprising: a substrate having a plurality of discontinuous cuts formed therein, the plurality of discontinuous cuts being formed such that when the substrate is subjected to deformation, the substrate is capable of deformation beyond an initial state so as to achieve a first shaped three-dimensional state.

Also provided are methods, comprising implanting a device according to the present disclosure into a subject.

Further disclosed are methods, comprising contacting the tissue of a subject to an intraoperative device according to the present disclosure.

Additionally disclosed are templates, comprising: a stencil pattern configured to overlay a substrate, the stencil being configured such that cutting the substrate in accordance with the stencil pattern gives rise to an intraoperative device according to the present disclosure.

Also provided are methods, comprising: forming a plurality of discontinuous cuts in a substrate such that when the substrate is subsequently subjected to deformation, the substrate is capable of deformation beyond an initial state so as to achieve a first shaped three-dimensional state.

Further provided are methods, comprising: defining a plurality of contour lines on a substrate in an initial state, the contour lines corresponding to planes in a first shaped three-dimensional state of the substrate, the planes being parallel to one another and being normal to a direction Z that is normal to the substrate in the initial state; defining a plurality of guide lines emanating from an origin point on the substrate; forming a cut through the substrate along a contour line so as to give rise to a contour cut between an intersection of the contour line with a first guide line and an intersection of the contour line with a second guide line that is adjacent to the first guide line, the cut being performed such that when the substrate is subjected to deformation, the substrate is capable of deformation beyond an initial state so as to achieve a first shaped three-dimensional state.

Also disclosed are intraoperative devices, comprising: a substrate having a perimeter, and the substrate having a plurality of contour cuts (sometimes termed contour line cuts) formed therethrough, a contour cut being formed along at least a portion of a contour line that corresponds to a plane of a three-dimensional template projected onto the substrate, the contour cut optionally being defined between an intersection of the contour line with a first guide line and an intersection of the contour line with a second guide line that is adjacent to the first guide line, the first guide line and the second guide line optionally intersecting at a common origin point on the substrate; the contour cut being formed such that when the substrate is subjected to deformation, the substrate is capable of deformation beyond an initial state so as to achieve a first shaped three-dimensional state, the first shaped three-dimensional state defining a perimeter.

Further provided are intraoperative devices, comprising: a substrate having a perimeter, and the substrate having at least a first plurality of contour cuts formed therethrough and a second plurality of contour cuts formed therethrough, wherein the first plurality of contour cuts lie on a first enclosed loop defined on the substrate, the first enclosed loop optionally overlaying or being symmetric with a first contour line that corresponds to a first plane of a three-dimensional template projected onto the substrate, wherein the second plurality of contour cuts lie on a second enclosed loop defined on the substrate, the second enclosed loop optionally overlaying or being symmetric with a second contour line that corresponds to a second plane of a three-dimensional template projected onto the substrate, the second enclosed loop enclosing the first enclosed loop, the first plurality of contour cuts and the second plurality of contour cuts being formed such that when the substrate is subjected to deformation, the substrate is capable of deformation beyond an initial state so as to achieve a first shaped three-dimensional state, the first shaped three-dimensional state defining a perimeter.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various aspects discussed in the present document. In the drawings:

FIG. 15 provides an illustration of a 3D shape formed from a cut 2D substrate according to the present disclosure;

FIG. 25B provides an illustration of an exemplary substrate in a pre-cut and unexpanded form according to the present disclosure;

FIG. 31 provides an illustration of exemplary parameters used to characterized the disclosed technology;

FIG. 35 provides exemplary embodiments of the disclosed technology;

FIG. 42 provides exemplary embodiments of the disclosed technology;

FIG. 45 provides exemplary embodiments of the disclosed technology;

FIG. 47 provides exemplary embodiments of the disclosed technology;

FIG. 48 provides exemplary embodiments of the disclosed technology;

FIG. 49 provides exemplary embodiments of the disclosed technology; and

DETAILED DESCRIPTION OF ILLUSTRATIVE EMBODIMENTS

Figure 1:
FIG. 1 provides an illustrative image of an intraoperative device (in a planar, initial state) according to the present disclosure.

The present disclosure may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable, and it should be understood that steps can be performed in any order.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range. In addition, the term "comprising" should be understood as having its standard, open-ended meaning, but also as encompassing "consisting" as well. For example, a device that comprises Part A and Part B may include parts in addition to Part A and Part B, but may also be formed only from Part A and Part B.

Existing tissue reinforcing matrices (ADMs) come in either square/rectangular/contoured flat two-dimensional sheets. The surgeon will take these sheets of ADM and inset them against the chest wall to create the sling/pocket necessary to support the implant or the autologous tissue transfer. Not only does this method require the use of these expensive ADMs (e.g., appx. $5000 for one sheet of 8"×16" of AlloDerm™ to reconstruct one breast), it requires valuable operating room time and demanding surgical skill to perform safely and correctly.

Through applying principles from kirigami, the present disclosure provides medical devices (along with related methods) that allow for improved outcomes in surgical procedures, e.g., autologous breast reconstruction. Kirigami uses bending, folding, cutting, (and in some instances) pasting to create complex three-dimensional (3D) structures from a flat sheet.

The proposed approach provides a number of advantages including, e.g., (a) increased speed and ease for surgeons, (b) lower costs for third-party payers (less ADM used to reconstruct a single breast), (c) reduced costs for hospitals (including reduced operating room times), (d) improved profits for ADM manufacturers (increased value density of ADM by increasing price per volume, and reduced waste of ADM), and (e) promotion of positive patient outcomes (better stability of the implant in chest wall, and optimal aesthetic outcomes with fewer revisions and complications)

By pre-cutting two-dimensional sheets of ADM using kirigami-type techniques, these modified sheets of ADM can quickly expand into the desired three-dimensional shape/pocket/sling that the surgeon needs to perform a successful breast reconstruction. These three-dimensional sheets of ADM can be used to wrap either implants or autologous tissue in their entirety. Once wrapped, the implant or tissue can be secured by simply stitching the ADM to the chest wall. It is currently impossible to suture a permanent breast implant to the chest wall; therefore, by wrapping an implant with a kirigami-ADM, the surgeon can now secure the implant to the chest wall by simply suturing the kirigami-ADM.

By pre-cutting two-dimensional sheets of pre-packaged ADM using kirigami, these modified sheets of ADM can quickly expand into the desired three-dimensional shape/pocket/sling that the surgeon needs to perform a successful breast reconstruction. These three-dimensional sheets of ADM can be used to wrap either implants or autologous tissue in their entirety. Once wrapped, the implant or tissue can be secured by simply stitching the ADM to the chest wall. It is currently impossible to suture a permanent breast implant to the chest wall; therefore, by wrapping an implant with a kirigami-ADM, the surgeon can now secure the implant to the chest wall by simply suturing the kirigami-ADM.

In one aspect, the present disclosure provides intra-operative medical devices designed to achieve better long-lasting aesthetic outcomes in immediate autologous breast reconstruction following skin/nipple sparing mastectomy for breast cancer patients. A device can be, e.g., a cutting-guide flap wrap that allows the plastic surgeon to build an anatomically breast-shaped envelope made from a bio-absorbable mesh that will house a free-flap for ultimate transfer to the chest wall for breast reconstruction. The envelope can line a breast mold for better intra-operative control during free-flap shaping and better support in breast reconstruction.

The disclosed technology can include cut patterns on an existing bio-absorbable material (e.g., Vicryl™ mesh, acellular dermal matrices, and the like) that in turn allows surgeons to stretch the 2D mesh into a 3D shape, and wrap the 3D shape about the transferred tissues for implant. Through design of the cut patterns in 2D, one can locally control the stretchability and elasticity within the mesh. In turn, the wrap can then provide shape and support to the reconstructed breast in the desired regions while minimizing operative time and cost.

By use of the disclosed technology, one can minimize the materials required (i.e., size of meshes/matrices) by maximizing the stretchability and mater strength. A device can be, e.g., seamless with only a single suture used to hold the mesh wrap in place. The present disclosure also provides templates to guide the cut of the mesh to a "patient-specific" design that can be used for customized breast reconstruction.

Figures

FIG. 1 provides an exemplary device according to the present disclosure. As shown in FIG. 1, a device can be present in planar (2D) form. As shown in FIG. 1, a device can include a plurality of cuts formed in the substrate of the device. A cut need not be symmetric (either self-symmetric or symmetrically-arranged relative to other cuts), but it can be one or both of the foregoing. A cut can also be asymmetric. As shown, the cuts can be arranged in a roughly circular pattern, but this is not a requirement. Also as shown in FIG. 1, a substrate can include a region (in this FIG., the circular region disposed toward the middle of the substrate) that is free of cuts or substantially free of cuts.

Figure 2:
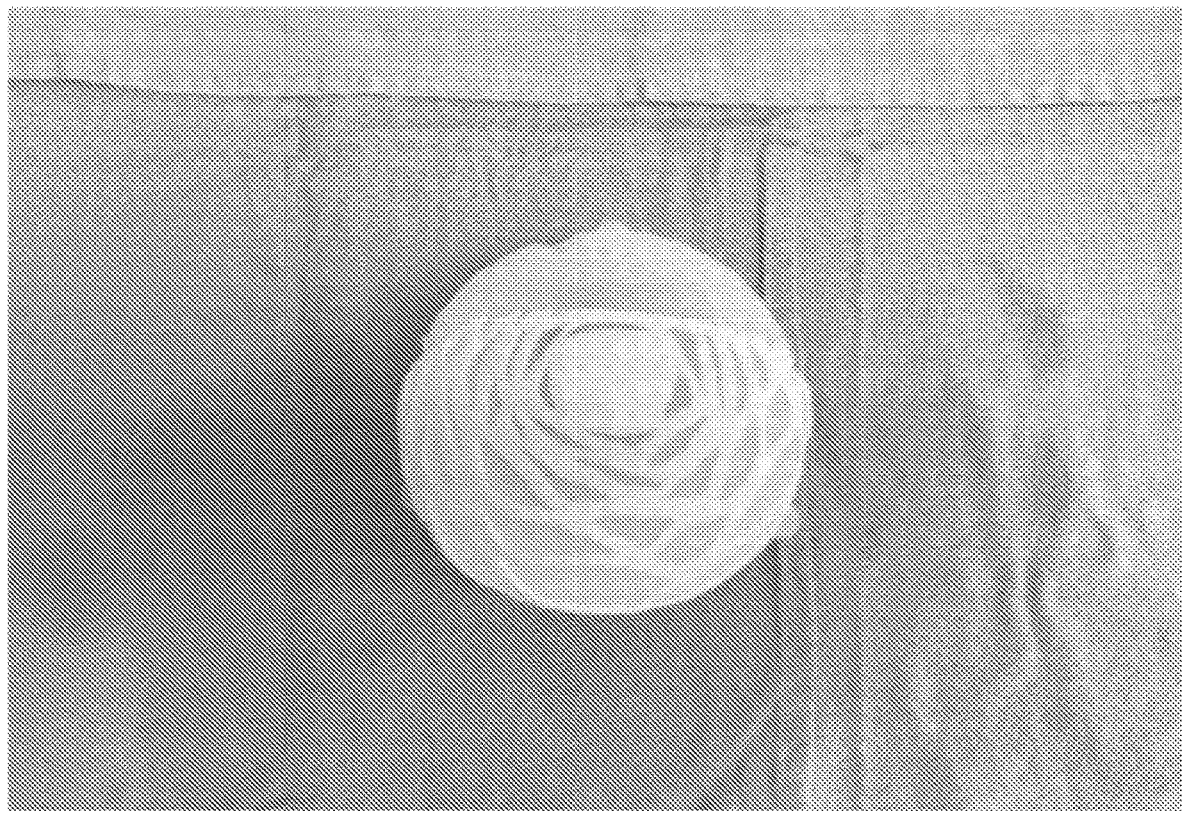
FIG. 2 provides an image of the device of FIG. 1, showing the device in a 3D state and disposed about a tissue model showing the device conforming to the model.

FIG. 2 shows the device of FIG. 1 in a deployed, 3D configuration. As shown in FIG. 2, the device has been deformed so that it achieves a 3D configuration, in this case a configuration that is cup-like or otherwise concave configuration. (This configuration is illustrative only.) As shown, the cup-like configuration can conform to the exterior of tissue, in this instance a breast implant model. Although not labeled in FIG. 2, a device (particularly in a 3D configuration) can include a region that differ from one another in rigidity, stretchability, elasticity, or any combination of the foregoing. In this way, a 3D configuration of a disclosed device can provide relatively rigid support to breast tissue in one location, but also provide elasticity and/or stretchability in another location. By configuration of the pattern and/or shape of the cuts in the 2D substrate that is used to form the 3D configuration, one can give rise to regions of the 3D configuration that have different properties.

Figure 3:
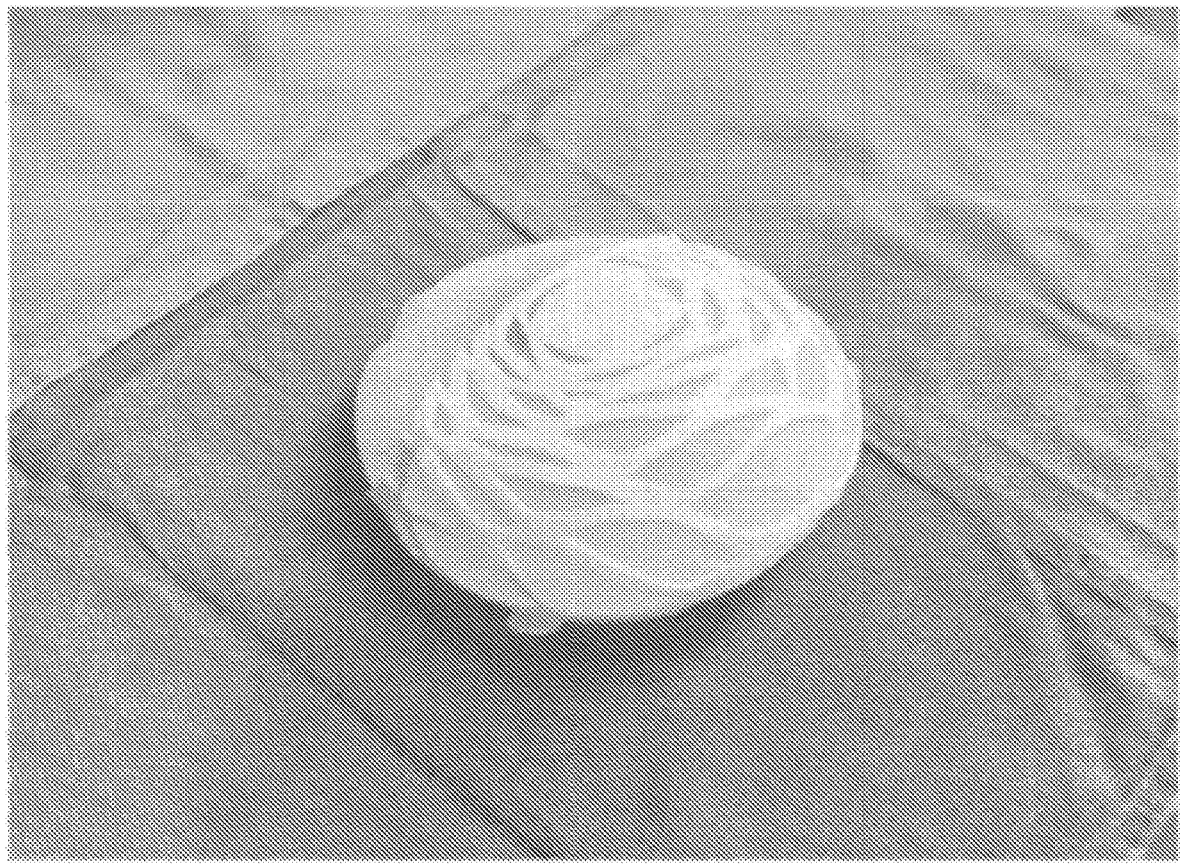
FIG. 3 provides a further view of the device of FIG. 1, showing the device in a 3D state and disposed about a tissue model showing the device conforming to the model.

FIG. 3 provides an alternative view of the device of FIG. 2. As shown in FIG. 3, a device can conform to tissue and can even wrap partially or even completely around tissue. Also as shown in FIG. 3, a device can envelop only a portion of a tissue; as shown, part of the breast implant in FIG. 3 is not covered by the device.

Figure 4:
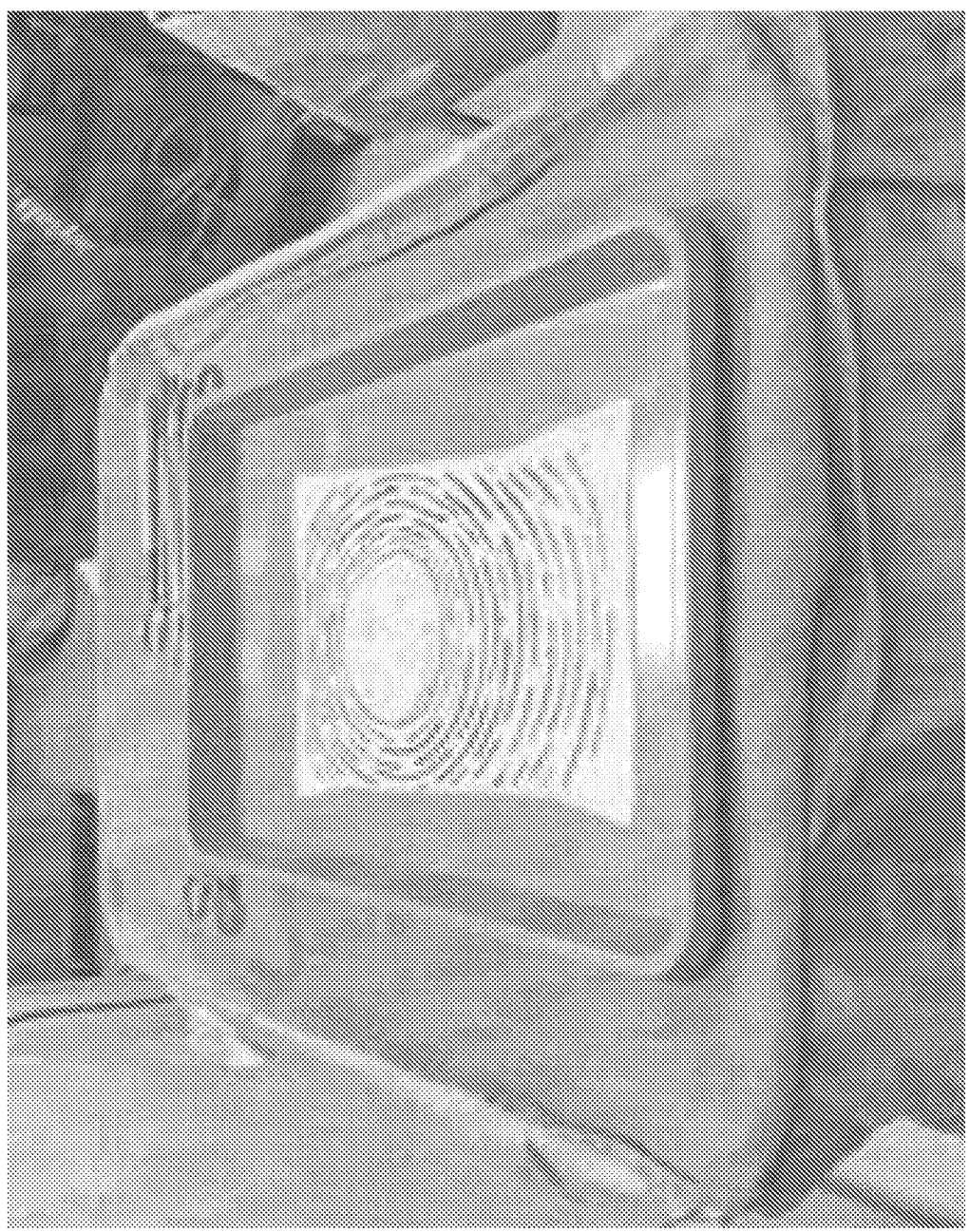
FIG. 4 provides an exemplary ADM sheet having formed thereon an exemplary design according to the present disclosure.

FIG. 4 provides an exemplary ADM sheet having formed thereon an exemplary design according to the present disclosure. After cuts are made in the sheet according to the design, the two-dimensional sheet of ADM will expand into the desired three-dimensional construct required to wrap the entire implant; these cuts can be made in the ADM before to sterile packaging so that the ADM sheet will be ready for immediate use by the surgeon. (In existing approaches, multiple sheets of ADM are used to wrap an implant in its entirety, which can take the surgeon valuable time to do—the disclosed approach allows a surgeon to wrap an entire implant using just a single sheet and in less time.)

Figure 5:
FIG. 5 provides an alternate view of the sheet of FIG. 4.

FIG. 5 provides an alternate view of the sheet of FIG. 4.

Figure 6:
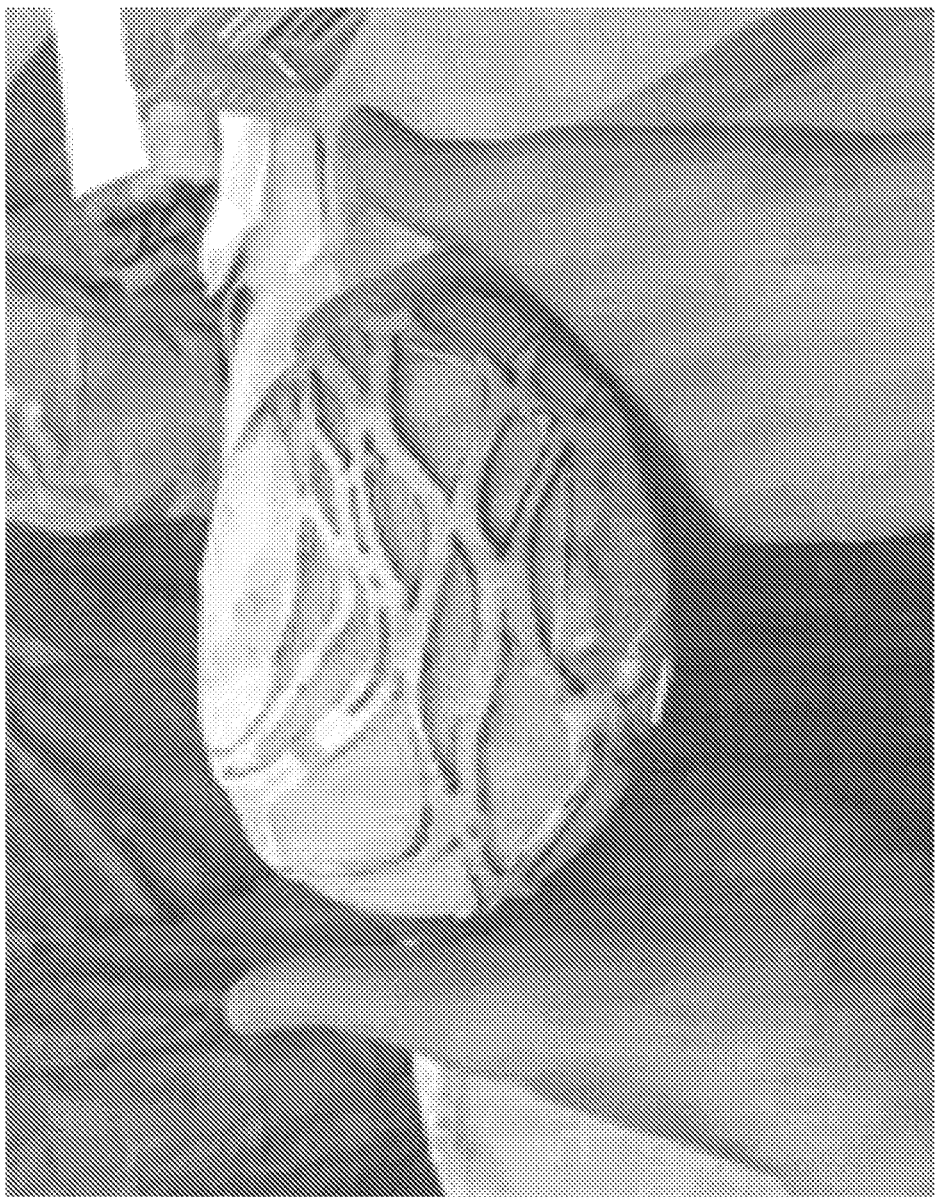
FIG. 6 provides an illustrative patterned sheet according the present disclosure wrapped about an exemplary breast prosthesis.

FIG. 6 provides an illustrative patterned sheet according the present disclosure wrapped about an exemplary breast prosthesis. As shown, a single sheet of Kirigami-ADM can expand and easily wrap the entire breast implant. The ADM is wrapped around a breast-tissue expander to demonstrate the effectiveness of the Kirigami-ADM prototype; the disclosed technology can be easily applied to permanent breast prostheses. Once wrapped, only a few sutures are necessary to secure the Kirigami-ADM around the breast implant, as shown in FIG. 6, and the implant is ready for implantation and can be secured by suturing the Kirigami-ADM to the chest wall in a fraction of the time needed by traditional methods.

Figure 7:
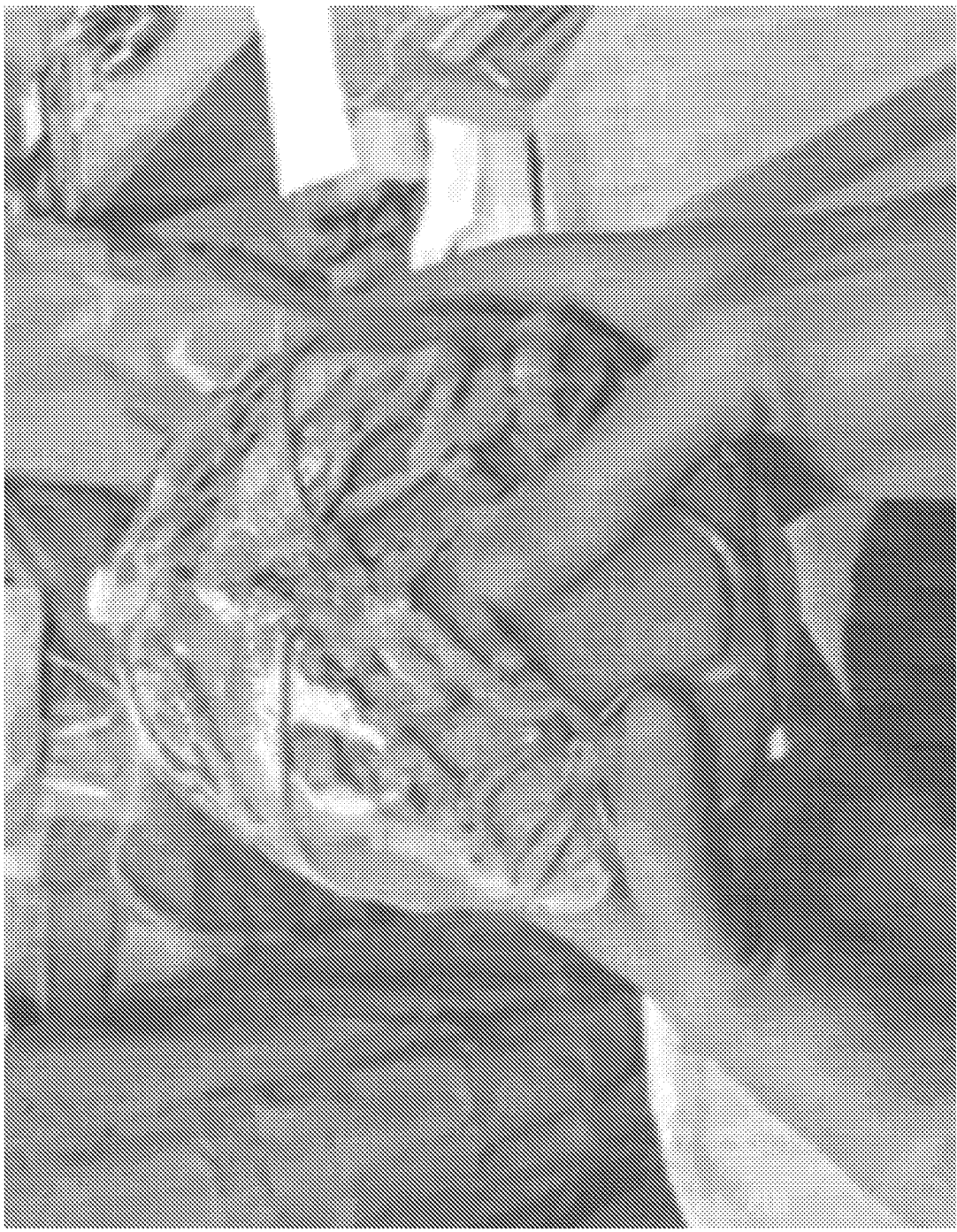
FIG. 7 provides a view of an illustrative patterned sheet according to the present disclosure wrapped about an exemplary breast prosthesis, with a few sutures used to secure the sheet around the prosthesis.

FIG. 7 provides a view of an illustrative patterned sheet according to the present disclosure wrapped about an exemplary breast prosthesis, with a few sutures used to secure the sheet around the prosthesis. As shown, the disclosed sheet can expand quickly and easily to provide full implant coverage with just a few sutures to secure the sheet about the implant—the implant can then be secured by suturing the Kirigami-ADM sheet to the chest wall, which can be done in a fraction of the time needed when using traditional methods FIG. 8 provides a view of an illustrative patterned sheet according to the present disclosure wrapped about an exemplary breast prosthesis.

Figure 8:
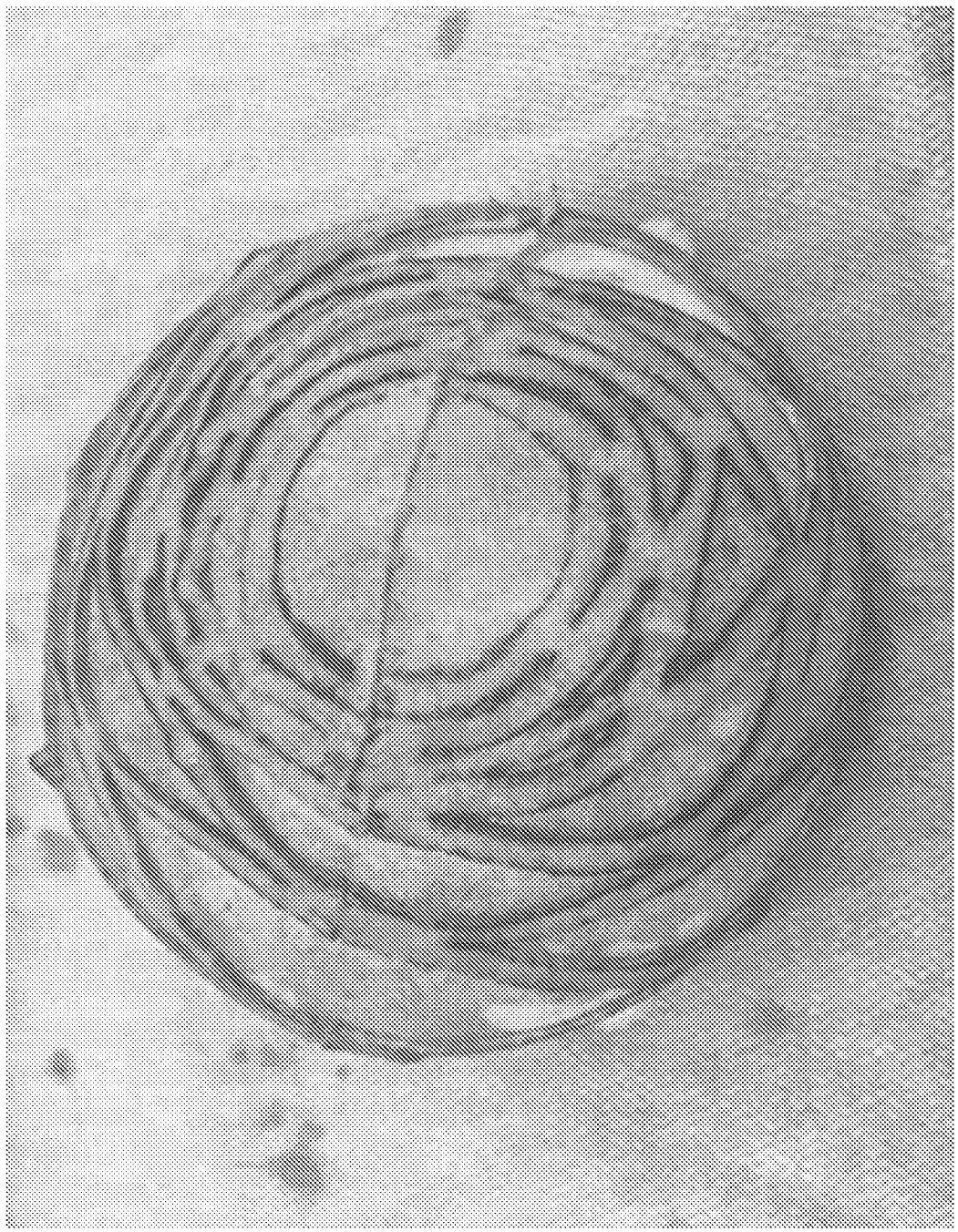
FIG. 8 provides a view of an illustrative patterned sheet according to the present disclosure wrapped about an exemplary breast prosthesis.
Figure 9:
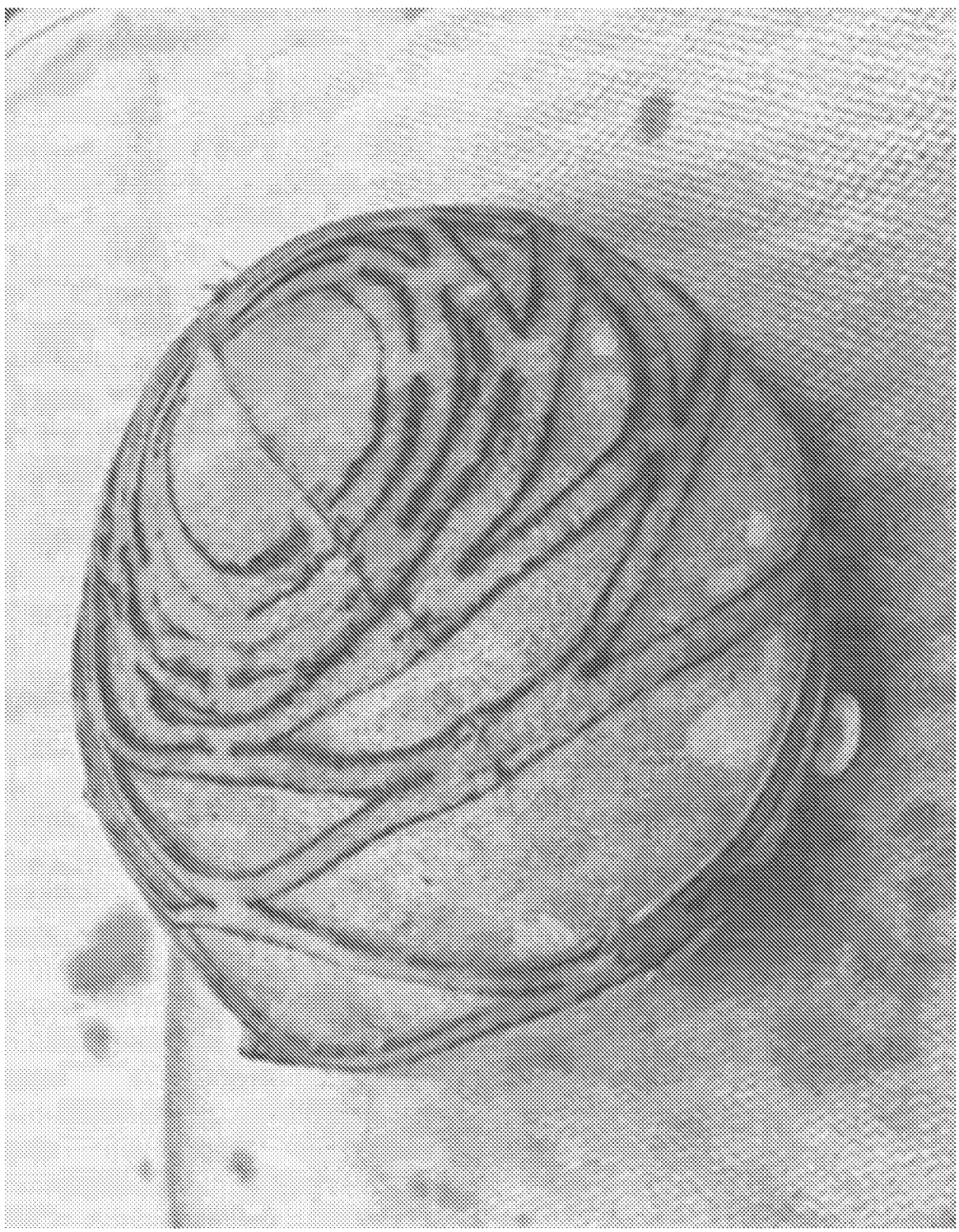
FIG. 9 provides another view of the patterned sheet of FIG. 8.

FIG. 9 provides another view of the patterned sheet of FIG. 8.

Figure 10:
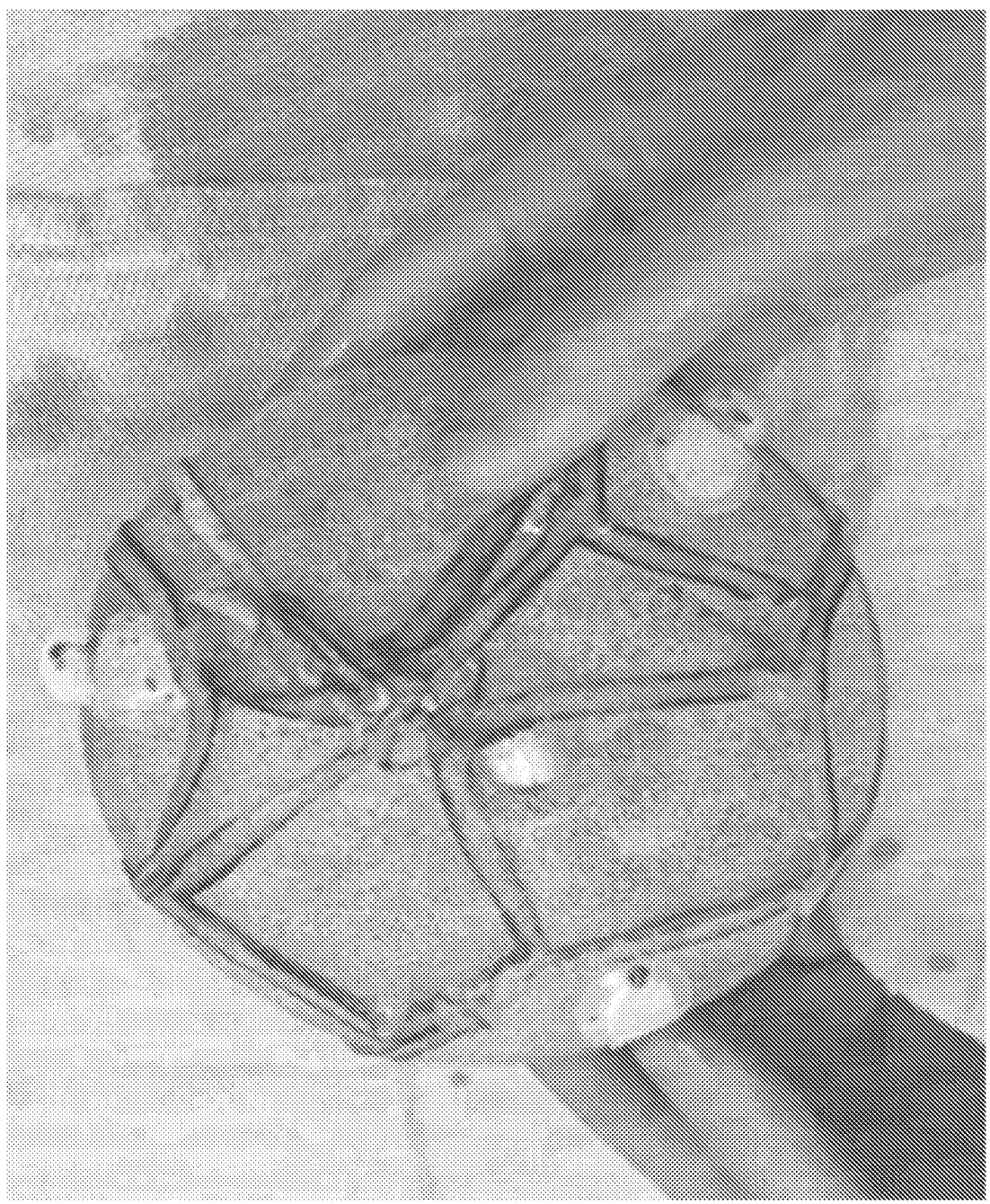
FIG. 10 provides a further view of the patterned sheet of FIG. 8 and FIG. 9.

FIG. 10 provides a further view of the patterned sheet of FIG. 8 and FIG. 9

Figure 11:
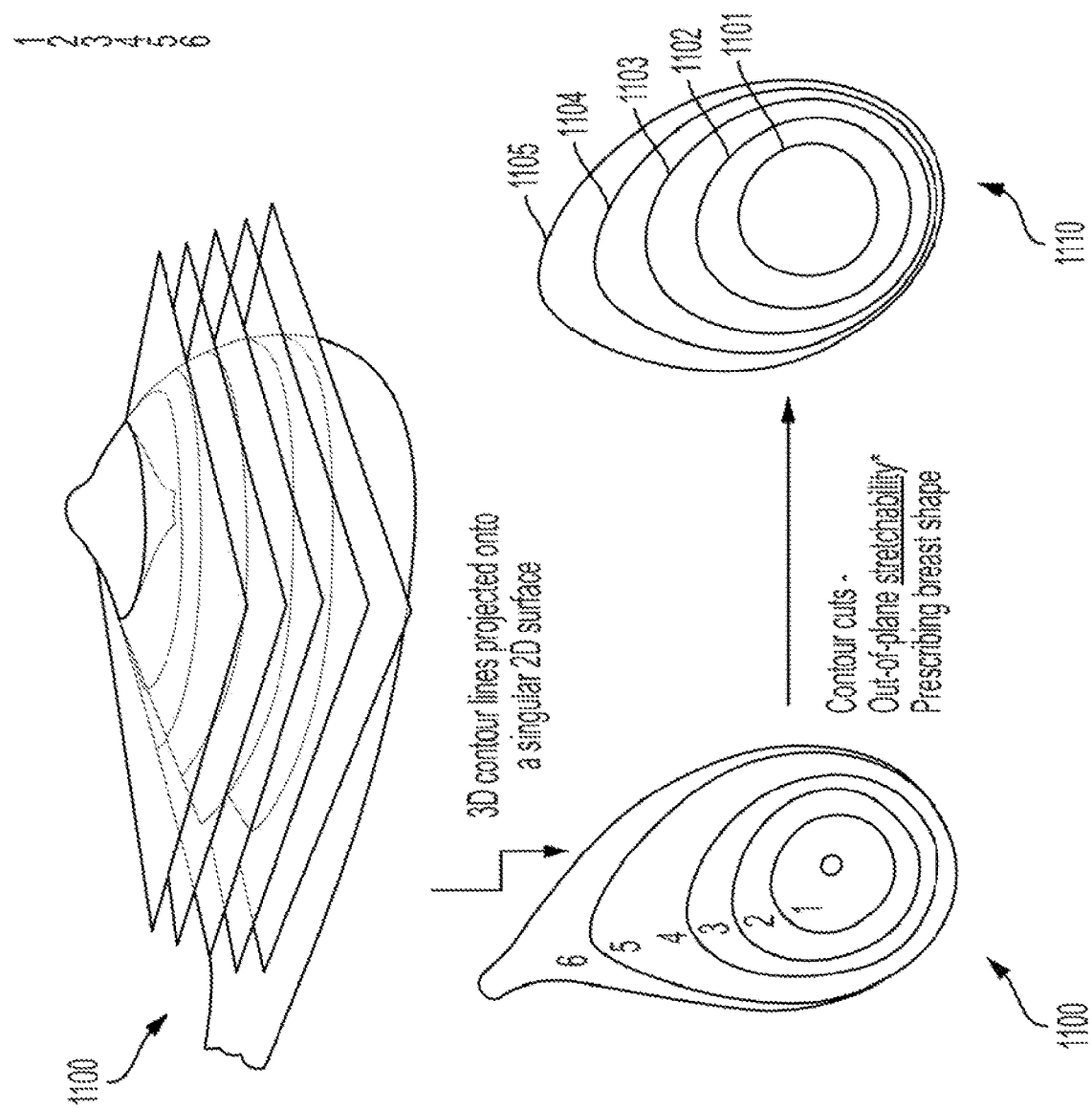
FIG. 11 provides an overview of creating contour lines on a 2D substrate corresponding to planes of a 3D form.

FIG. 10 provides a further view of the patterned sheet of FIG. 8 and FIG. 9;

FIG. 11 provides an overview of creating contour lines on a 2D substrate corresponding to planes of a 3D form 1100. As shown, a 3D model can be made of a desired form, e.g., a breast (upper panel). Contour lines can then be projected onto a 2D surface. The contour lines can be applied such that each "slice" between two contour lines is of the same thickness, although this is not a requirement. In FIG. 11, the 3D model has six contour lines projected onto the 2D surface. The projected contour lines are shown on substrate 1110, with contour line 1101 representing the boundary of slice 1 and slice 2, contour line 1102 representing the boundary of slice 2 and slice 3, contour line 1103 representing the boundary of slice 3 and slice 4, contour line 1104 representing the boundary of slice 4 and slice 5, and contour line 1105 representing the boundary of slice 6.

Figure 12:
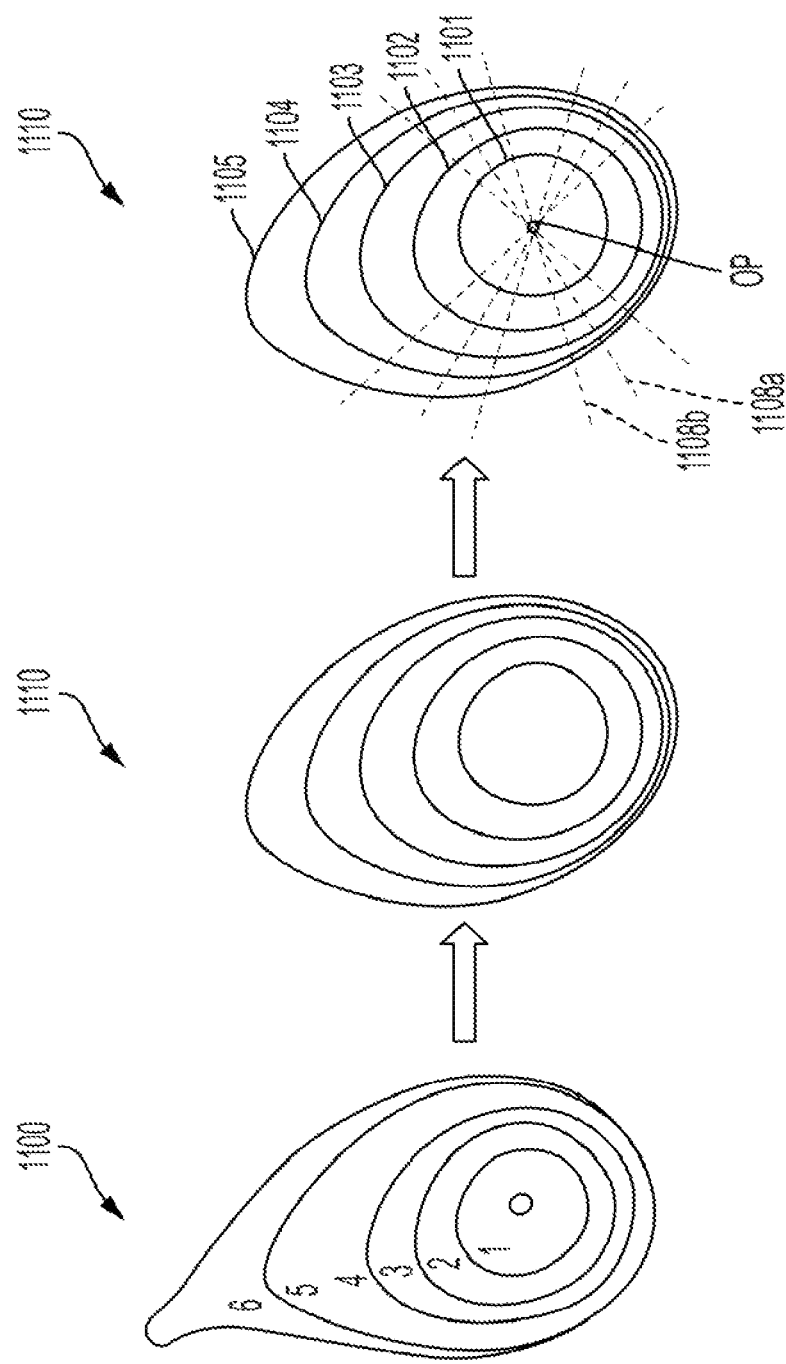
FIG. 12 provides a further overview of defining certain lines on a 2D substrate corresponding to the planes of a 3D form of the substrate.

FIG. 12 provides a further overview of defining certain lines on a 2D substrate corresponding to the planes of a 3D form of the substrate. In FIG. 12, the 3D model has six contour lines projected onto the 2D surface. The projected contour lines are shown on substrate 1110, with contour line 1101 representing the boundary of slice 1 and slice 2, contour line 1102 representing the boundary of slice 2 and slice 3, contour line 1103 representing the boundary of slice 3 and slice 4, contour line 1104 representing the boundary of slice 4 and slice 5, and contour line 1105 representing the boundary of slice 6. As shown on the right-hand panel, guide lines 1108a and 1108b emanate from origin point OP on substrate 1110. A plurality of guidelines can emanate from an origin point, and each of the plurality of guide lines can be onset by the same number of degrees from its neighboring guide lines. As an example, in a case where there are 10 guide lines, each guide line is offset from its neighbors by 360/10=36 degrees.

Figure 13:
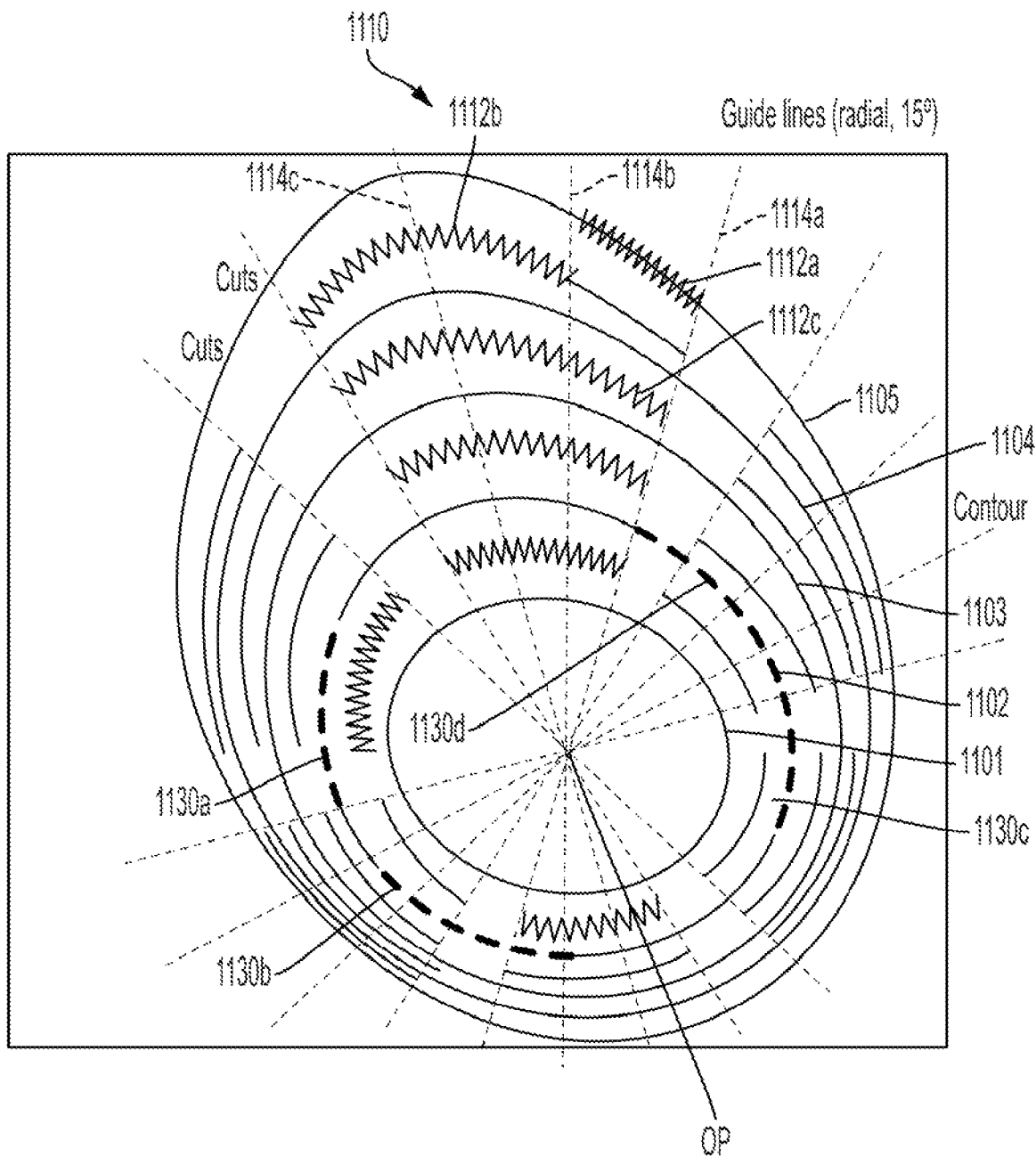
FIG. 13 provides an exemplary configuration for cuts in a substrate according to the present disclosure.

FIG. 13 provides an exemplary configuration for cuts in a substrate 1110 according to the present disclosure. As shown, contour lines 1101, 1102, 1103, 1104, and 1105 represent planes in a 3D form that have been projected onto 2D substrate 1110. Guide lines 1114a, 1114b, and 1114c emanate from origin point OP on substrate 1110. As shown by the heavier lines, a user can then form cuts along the contour lines; example cuts 1112a is shown. As shown a cut can be formed along a contour line to as to connect the intersection of that contour line with two adjacent guide lines. A cut can span two, three or more guidelines. A cut can cross a guide line, but this is not a requirement, as a cut can be formed along a contour line but not cross any guide lines. Cuts (e.g., 1112b and 1112c) can also be formed between contour lines.

Figure 14:
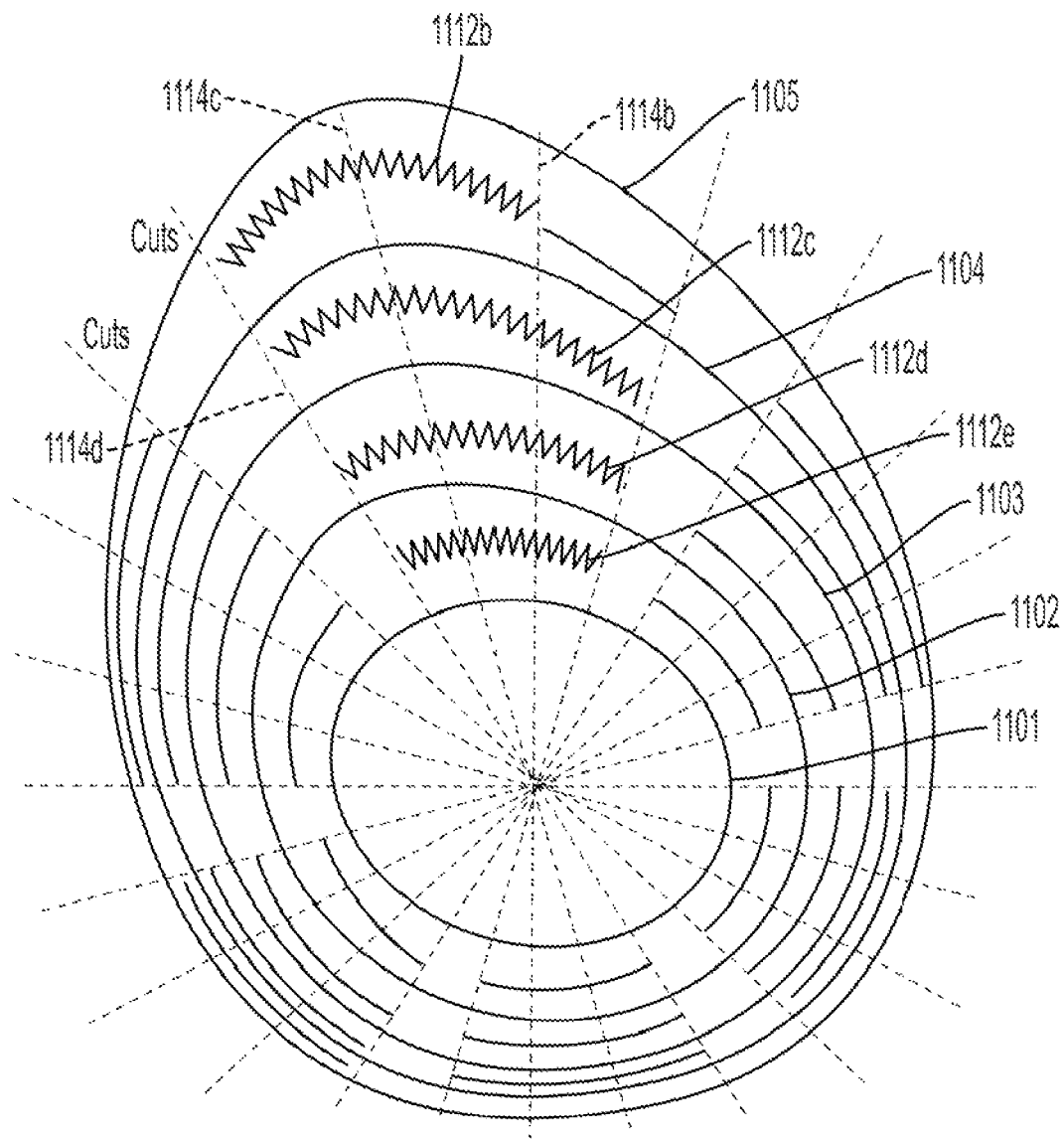
FIG. 14 provides an exemplary configuration for cuts in a substrate according to the present disclosure.

FIG. 14 provides an exemplary configuration for cuts in a substrate according to the present disclosure. As shown, contour lines 1101, 1102, 1103, 1104, and 1105 represent planes in a 3D form that have been projected onto 2D substrate 1110. Guide lines 1114a, 1114b, and 1114c emanate from origin point OP on substrate 1110. A user can then form cuts along contour lines (e.g., cuts 1112b, 1112c, and 1112d; contour lines for these cuts are not shown). Contour cuts can be formed along non-adjacent contour lines, along a given guide line. Contour cuts can also be formed along a given guide line between contour lines; for example, guide line 1114 crosses contour lines 1105, 1104, 1103, 1102, and 1101, and cuts are formed between, e.g., contour lines 1105 and 1104.

FIG. 15 provides an illustration of a 3D shape formed from a cut 2D substrate according to the present disclosure. As shown, 2D substrate 1500 bears a plurality of cuts (e.g., cuts along contour lines previously projected onto the substrate). Cut substrate 1500 can be expanded in a direction, e.g., a direction Z normal to the surface of the cut substrate, which expansion gives rise to 3D form 1502. As shown, the pattern of cuts in substrate 1500 allows for control over the conformation of 3D form 1502, as certain areas of substrate 1500 allow for more expansion in a direction (e.g., direction Z normal to the surface of the substrate) than other areas of the substrate.

Figure 16:
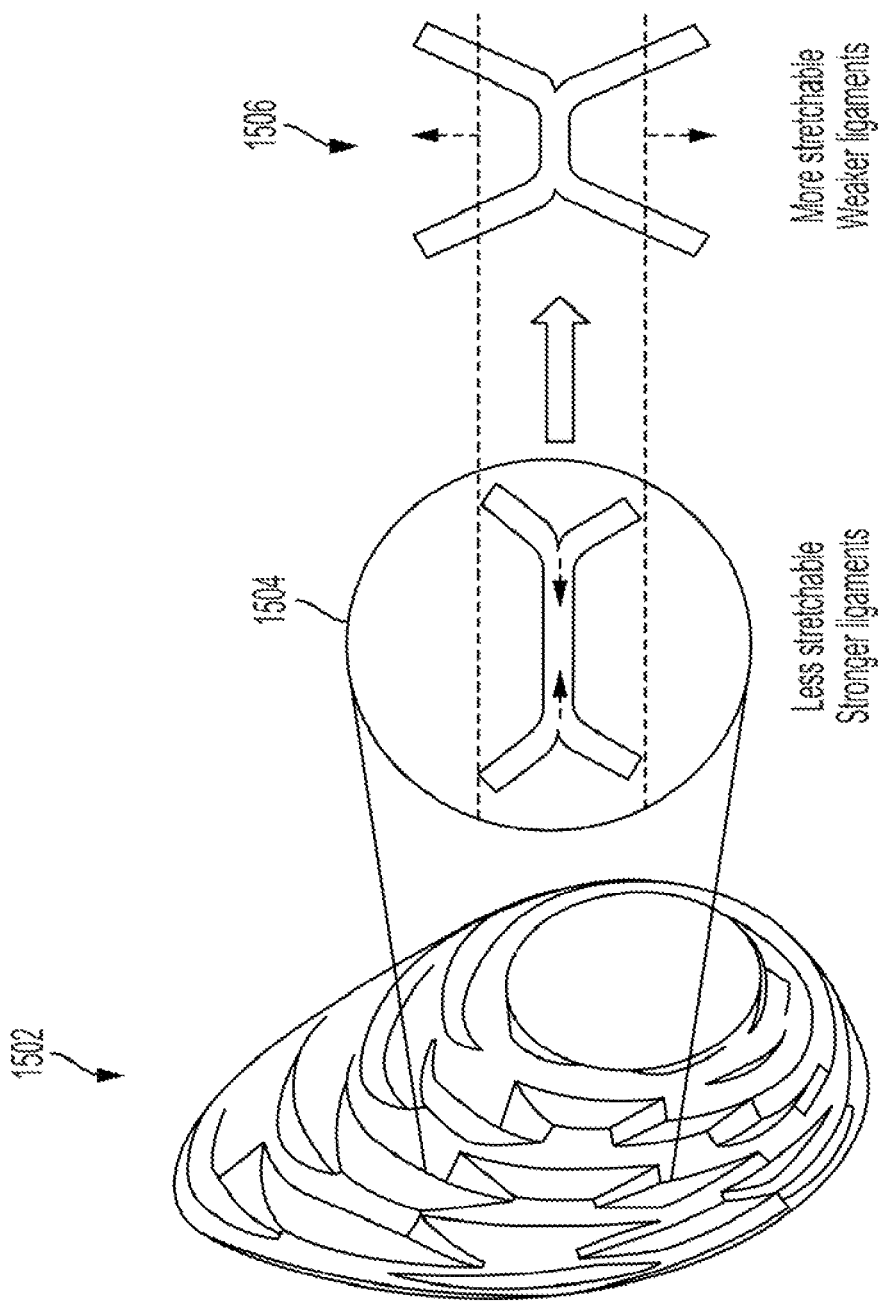
FIG. 16 provides further detail of a 3D shape formed from a cut 2D substrate according to the present disclosure.

FIG. 16 provides further detail of a 3D shape formed from a cut 2D substrate according to the present disclosure. FIG. 16 provides close-ups 1504 and 1506 of certain regions of cut 2D substrate 1502. As shown, the configuration of cuts in the substrate can allow for stretching/expansion in a particular direction and allow for less expansion in a different direction.

Figure 17:
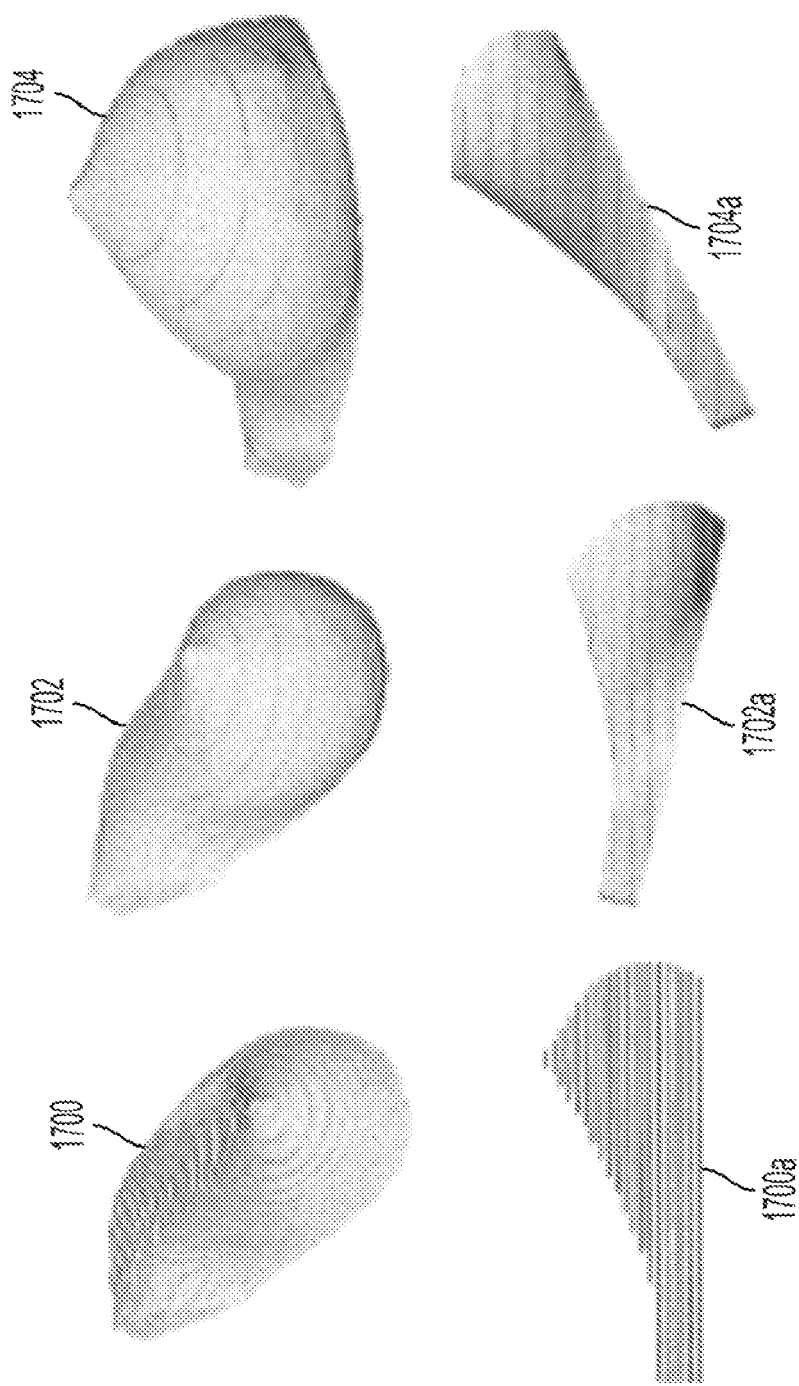
FIG. 17 provides exemplary renderings of 3D breast shapes, showing contour lines formed on the shapes.

FIG. 17 provides exemplary renderings of 3D breast shapes, showing contour lines formed on the shapes. Rendering 1700 provides a view of a particular 3D breast shape with contour lines, and view 1700a provides a side view of rendering 1700, showing the planes that correspond to the contour lines shown in 1700. Rendering 1702 provides a view of a particular 3D breast shape with contour lines, and view 1702a provides a side view of rendering 1702, showing the planes that correspond to the contour lines shown in 1702. Rendering 1704 provides a view of a particular 3D breast shape with contour lines, and view 1704a provides a side view of rendering 1704, showing the planes that correspond to the contour lines shown in 1704. As shown, renderings 1700, 1702, and 1704 illustrate differently-shaped breasts, as well as breasts that are tilted at different angles/attitudes. Thus, 3D objects of various shapes and attitudes can be represented with contour lines projected onto a 2D substrate.

Figure 18:
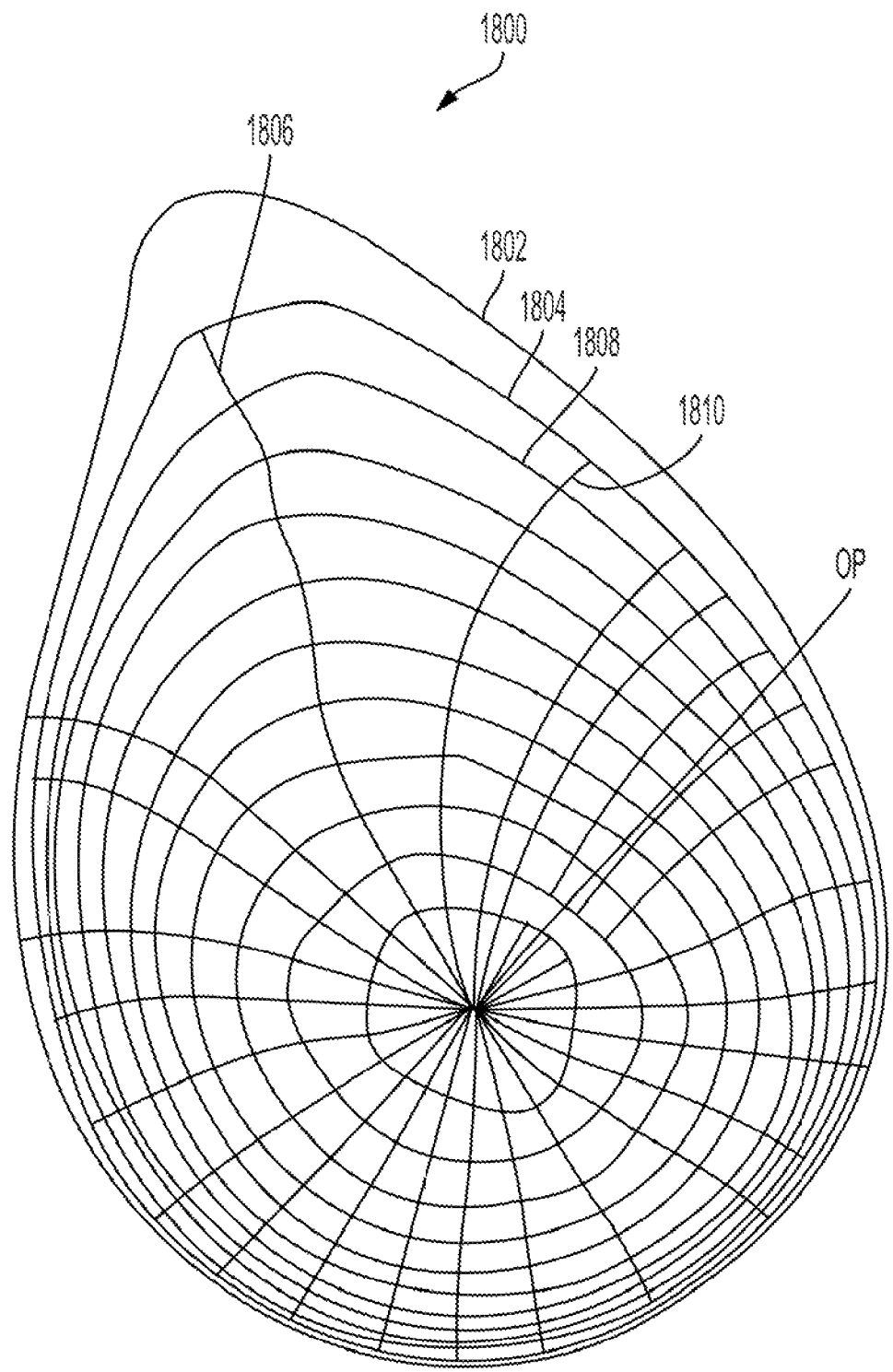
FIG. 18 provides an exemplary configuration for cuts in a substrate according to the present disclosure.

FIG. 18 provides an exemplary configuration for cuts in a substrate according to the present disclosure. As shown, substrate 1800 has defined thereon contour lines 1802, 1804, and 1808. Also defined on substrate 1800 are guide lines 1806 and 1810, which guide lines emanate from origin point OP. A guide line, as shown, can be configured such that the guideline is perpendicular to guide line that the guide line crosses. (This is not, however, a rule or a requirement.)

Figure 19:
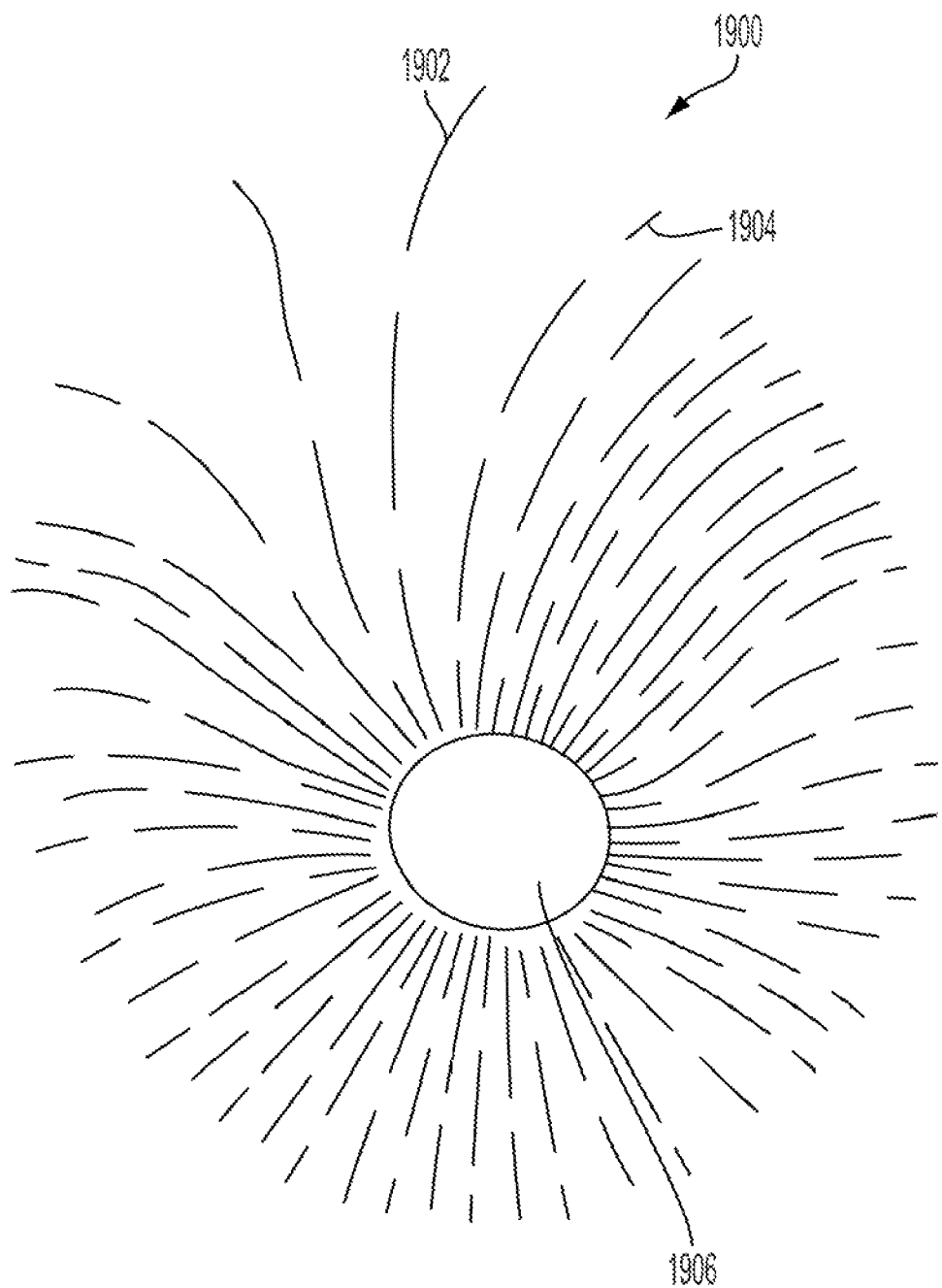
FIG. 19 provides an exemplary configuration for cuts in a substrate according to the present disclosure.

FIG. 19 provides an exemplary configuration for cuts in a substrate according to the present disclosure. As shown, substrate 1900 includes guide line cuts 1902 and 1904 (as well as other guide line cuts), which guide line cuts emanate outward from the center of the substrate 1900. As shown, however, a region 1906 of substrate 1900 is free of guide line cuts (or other cuts).

Figure 20:
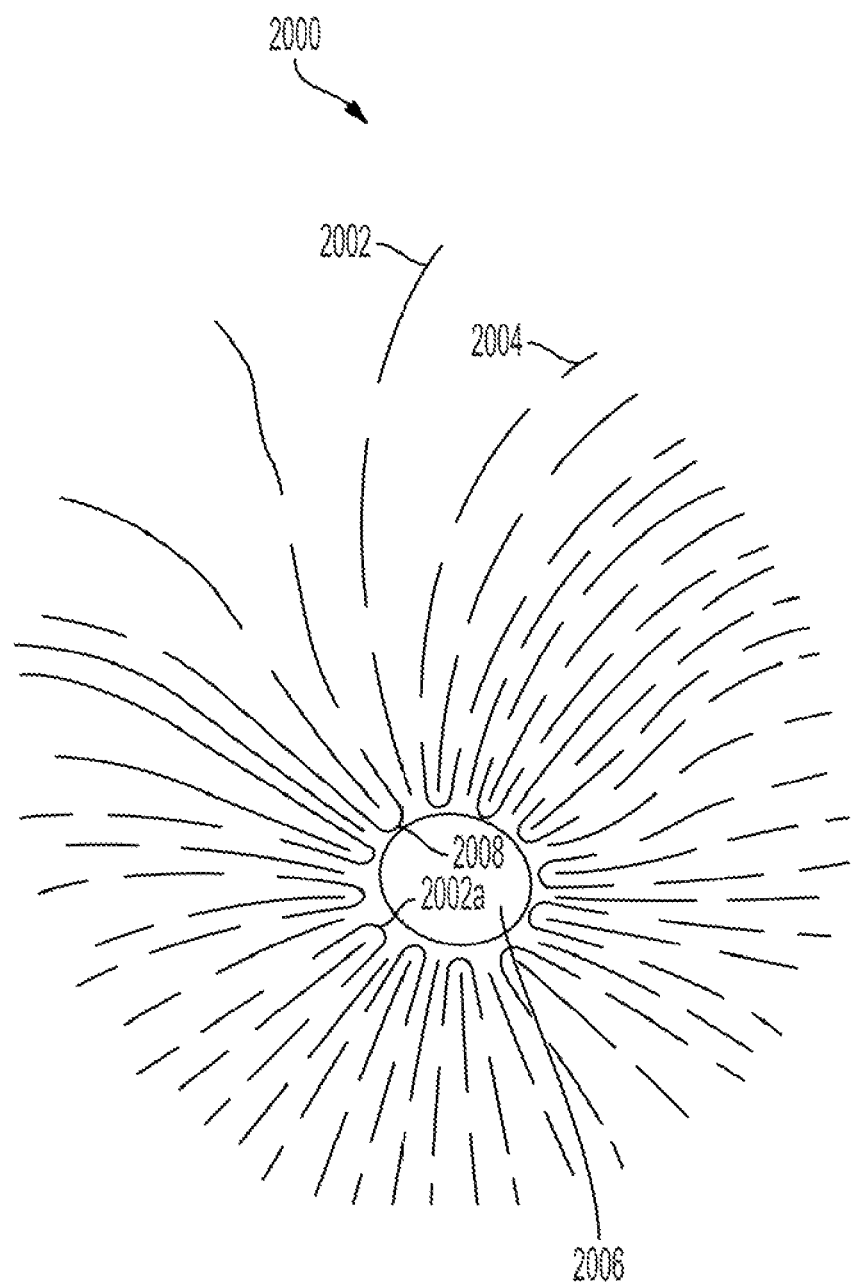
FIG. 20 provides an exemplary configuration for cuts in a substrate according to the present disclosure.

FIG. 20 provides an exemplary configuration for cuts in a substrate according to the present disclosure. As shown, substrate 2000 includes guide line cuts 2002 and 2004 (as well as other guide line cuts), which guide line cuts emanate outward from the center of the substrate 2000. As shown, however, a region 2006 of substrate 2000 is free of guide line cuts (or other cuts). Additional cuts 2008 and 2008a are shown; such cuts can be U-shaped such that they bracket another cut that is disposed within the "U".

Figure 21:
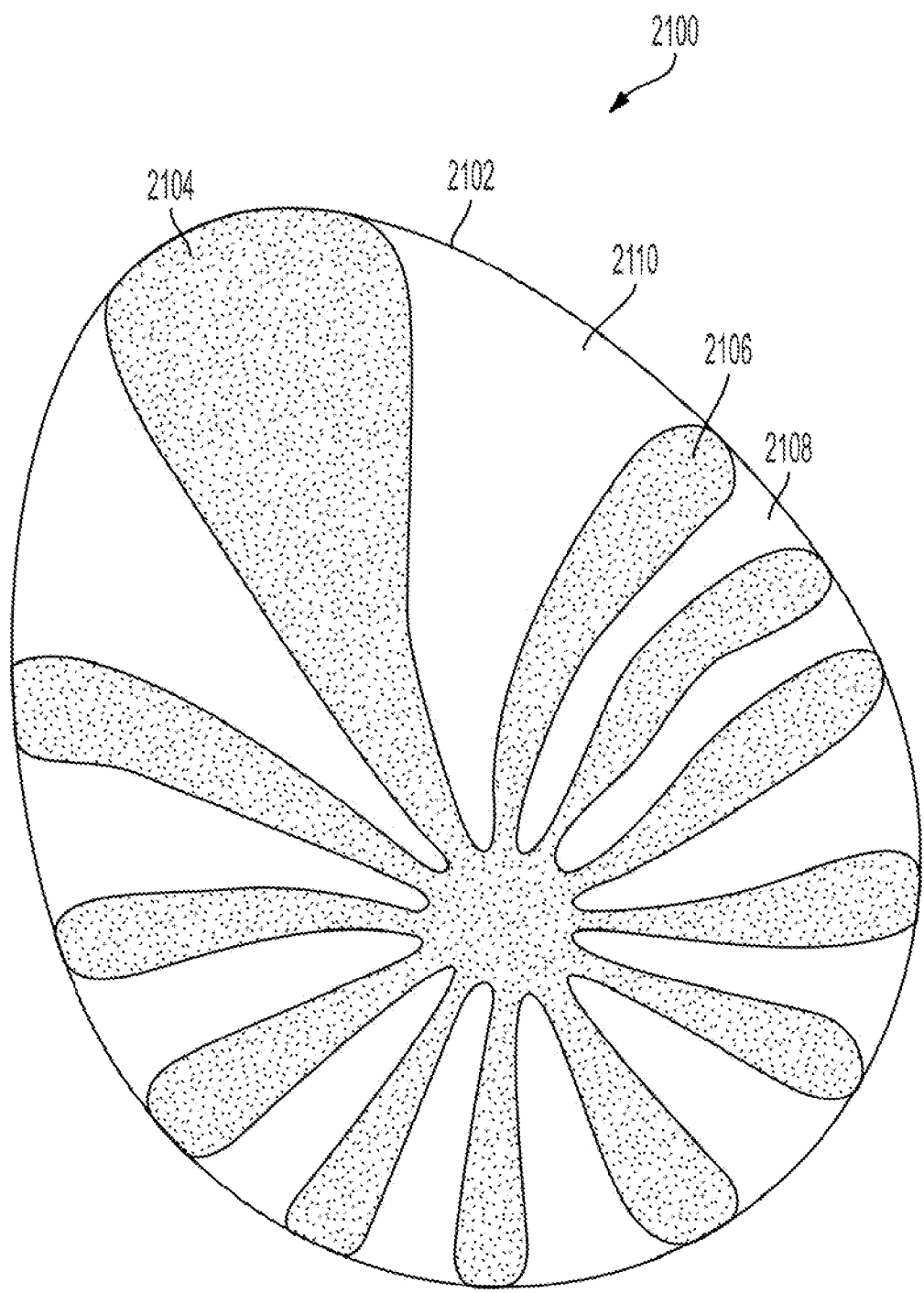
FIG. 21 provides an exemplary view of a substrate according to the present disclosure.

FIG. 21 provides an exemplary view of a substrate according to the present disclosure. As shown in FIG. 21, substrate 2100 with edge 2102 includes regions of different stretchability. In FIG. 21, light regions (2110 and 2108) are of comparatively greater rigidity, and dark regions 2104 and 2106 are of comparatively greater stretchability.

Figure 22:
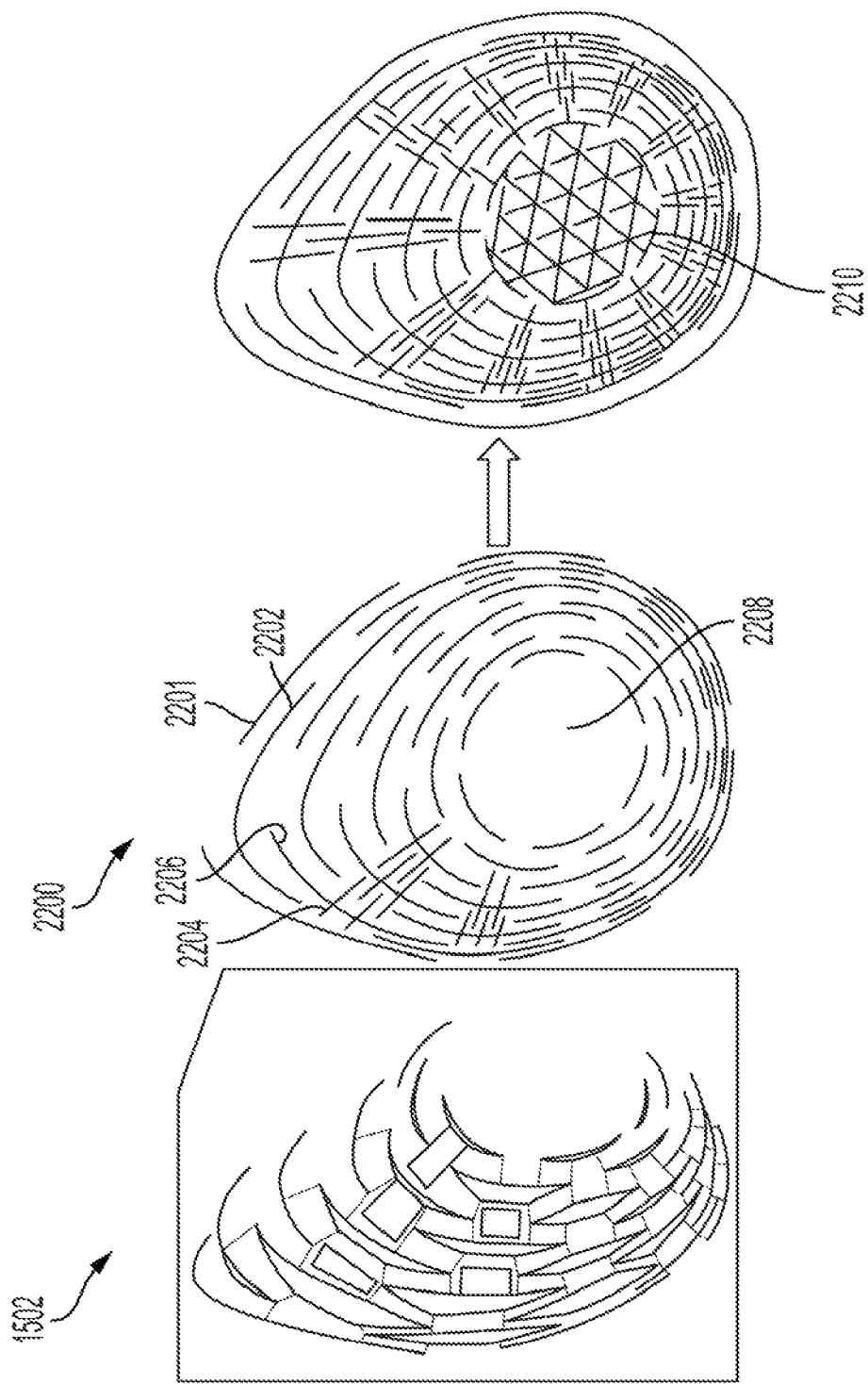
FIG. 22 provides an exemplary view of a 3D and a 2D substrate according to the present disclosure.

FIG. 22 provides an exemplary view of a 3D form and a 2D substrate according to the present disclosure. As shown, 3D form 1502 includes cuts running in various directions. Substrate 2200 provides contour cuts 2201, 2202, and 2206, which cuts can be formed along contour lines (not shown) defined on the substrate. Substrate 2200 also includes hierarchical contour cuts 2204, which hierarchical contour cut can cross a contour cut or otherwise be directed outward toward an edge of the substrate. Substrate 2200 includes a region 2208 that is free of any cuts. The addition of further cuts can give rise to an auxetic region 2210, as shown in FIG. 22.

Figure 23:
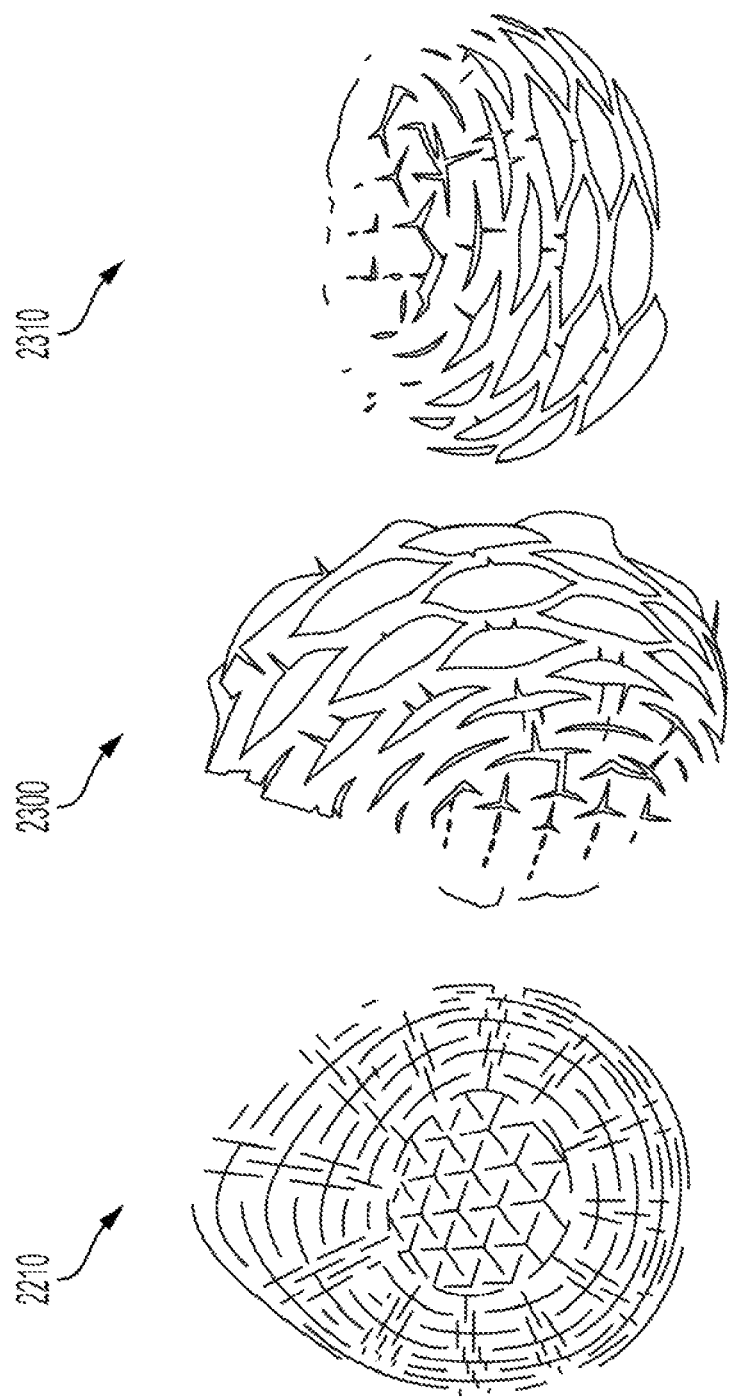
FIG. 23 provides an exemplary view of a 3D form according to the present disclosure.

FIG. 23 provides an exemplary view of a 3D form according to the present disclosure. Exemplary substrate 2210 includes, as shown, a plurality of contour cuts as well as a plurality of hierarchical contour cuts, which hierarchical contour cuts can cross one or more contour lines. A hierarchical contour cut can cross a contour line perpendicular to the contour line, but this is not a requirement. As shown, expanded substrate 2300 (i.e., substrate 2210 in expanded 3D form) is configured to at least partially wrap an implant or tissue. View 2310 provides a view of expanded substrate 2300 from an alternative angle.

Figure 24:
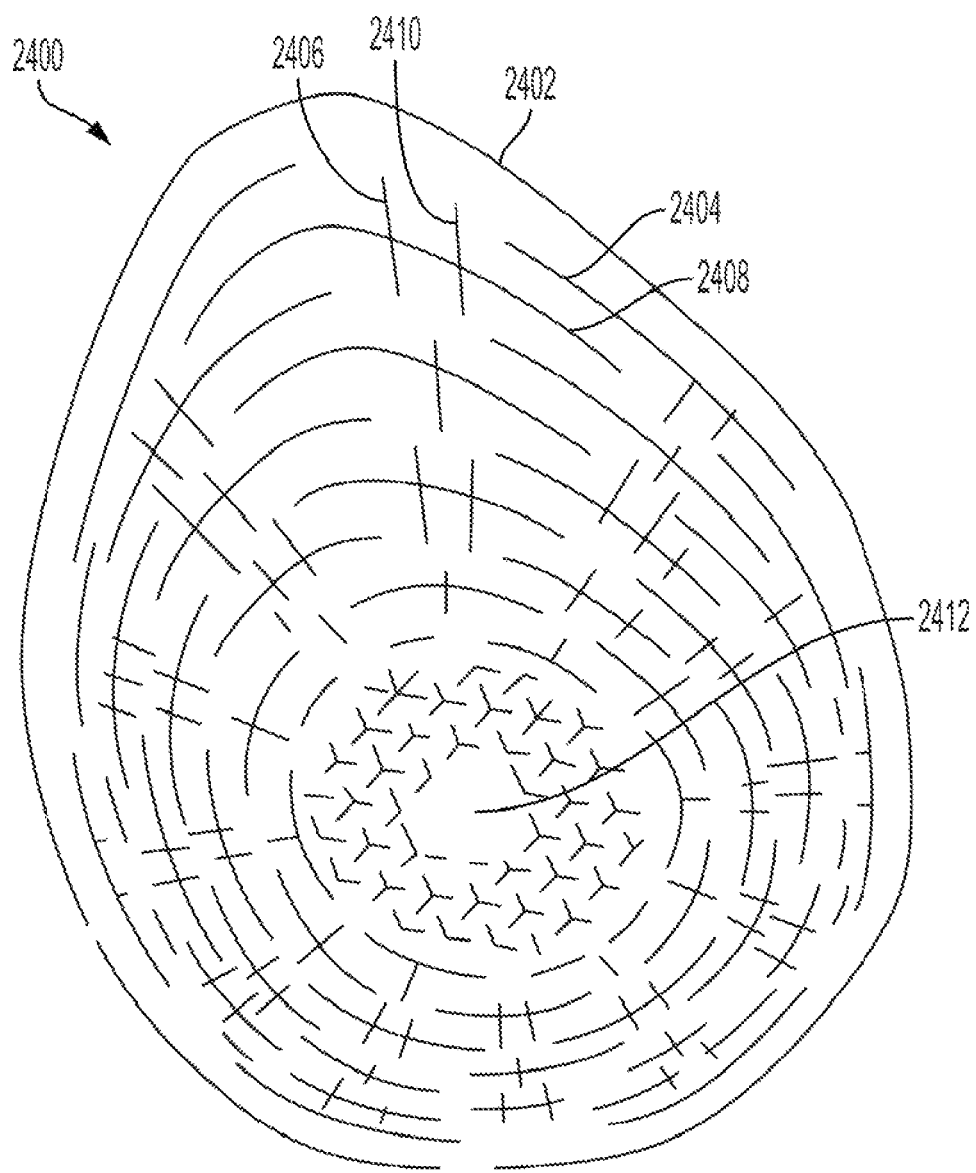
FIG. 24 provides an exemplary view of a substrate according to the present disclosure.

FIG. 24 provides an exemplary view of a substrate according to the present disclosure. As shown, cut substrate 2400 defines edge 2402 and auxetic region 2412. Contour cuts 2404 and 2408 are also shown. Hierarchical contour cuts 2406 and 2410 are shown crossing contour cut 2408. Without being bound to any particular embodiment, hierarchical contour cuts 2406 and 2410 can be formed on/along a guide line, but this is not a requirement.

Figure 25A:
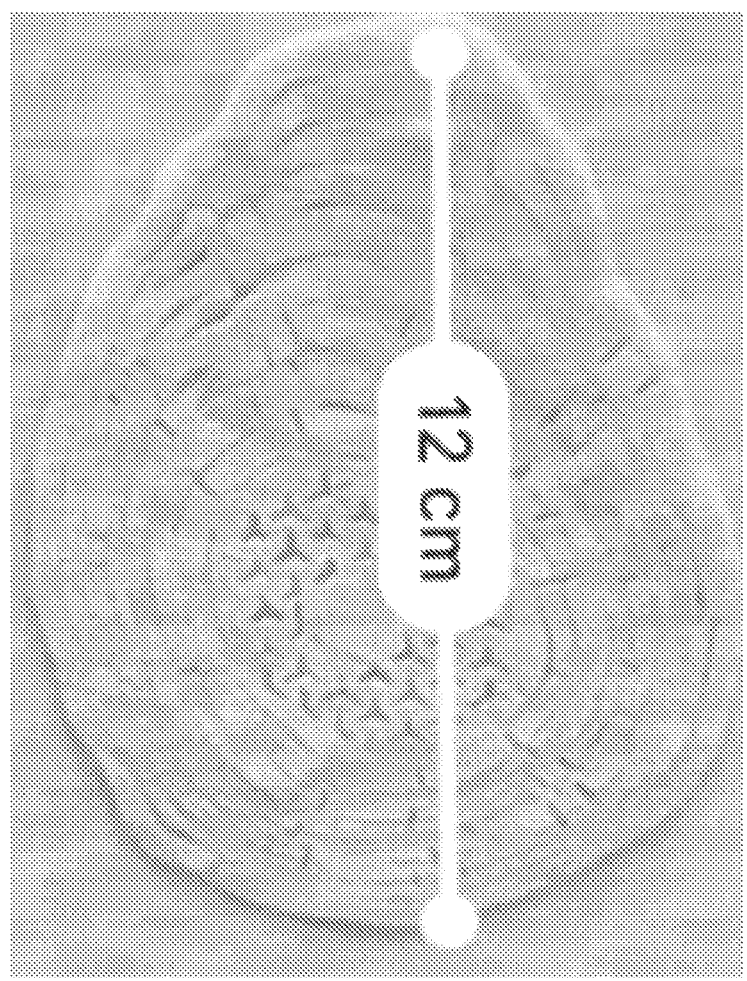
FIG. 25A provides an illustration of an exemplary substrate in unexpanded form according to the present disclosure.
Figure 28B:
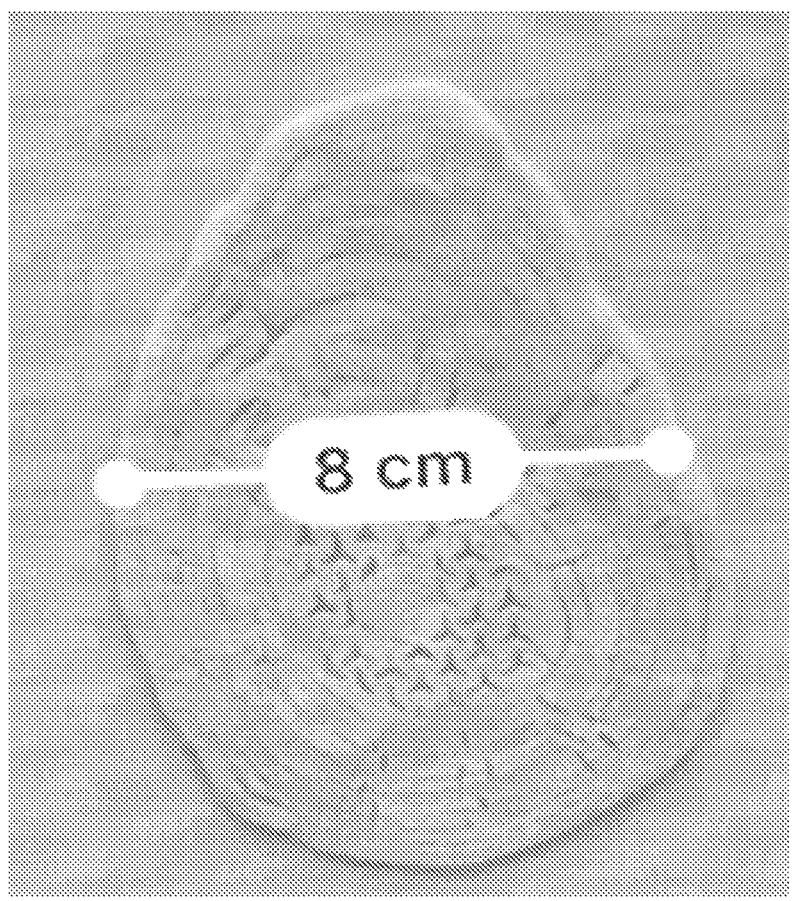
FIG. 28 provides views of a spherical implant wrapped by a substantially uncut substrate (the left panel is a view looking down at the wrapped implant when the implant is placed on a table; the right panel is a view looking sideways at the wrapped implant when the implant is mounted to a table that is tilted vertically so as to mimic the anatomic position of the implant in a patient who is standing and to show the effect of gravity)
Figure 26A:
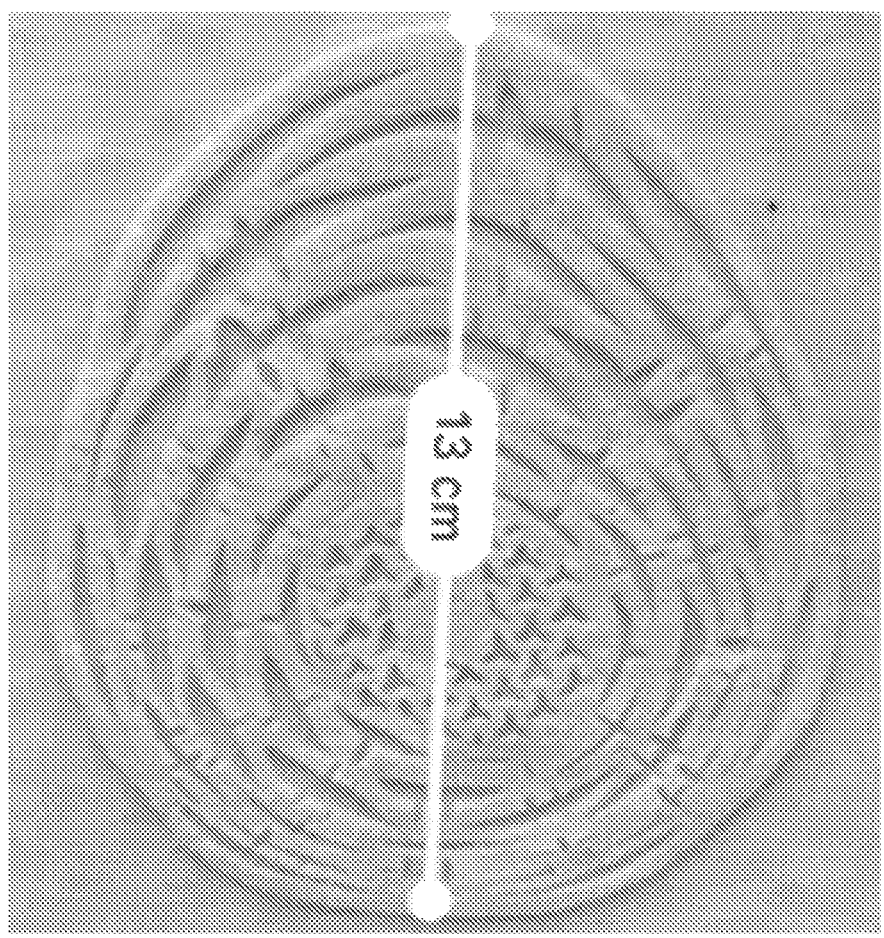
FIG. 26A provides an illustration of the substrate of FIG. 25A and FIG. 25B in an expanded form.
Figure 26B:
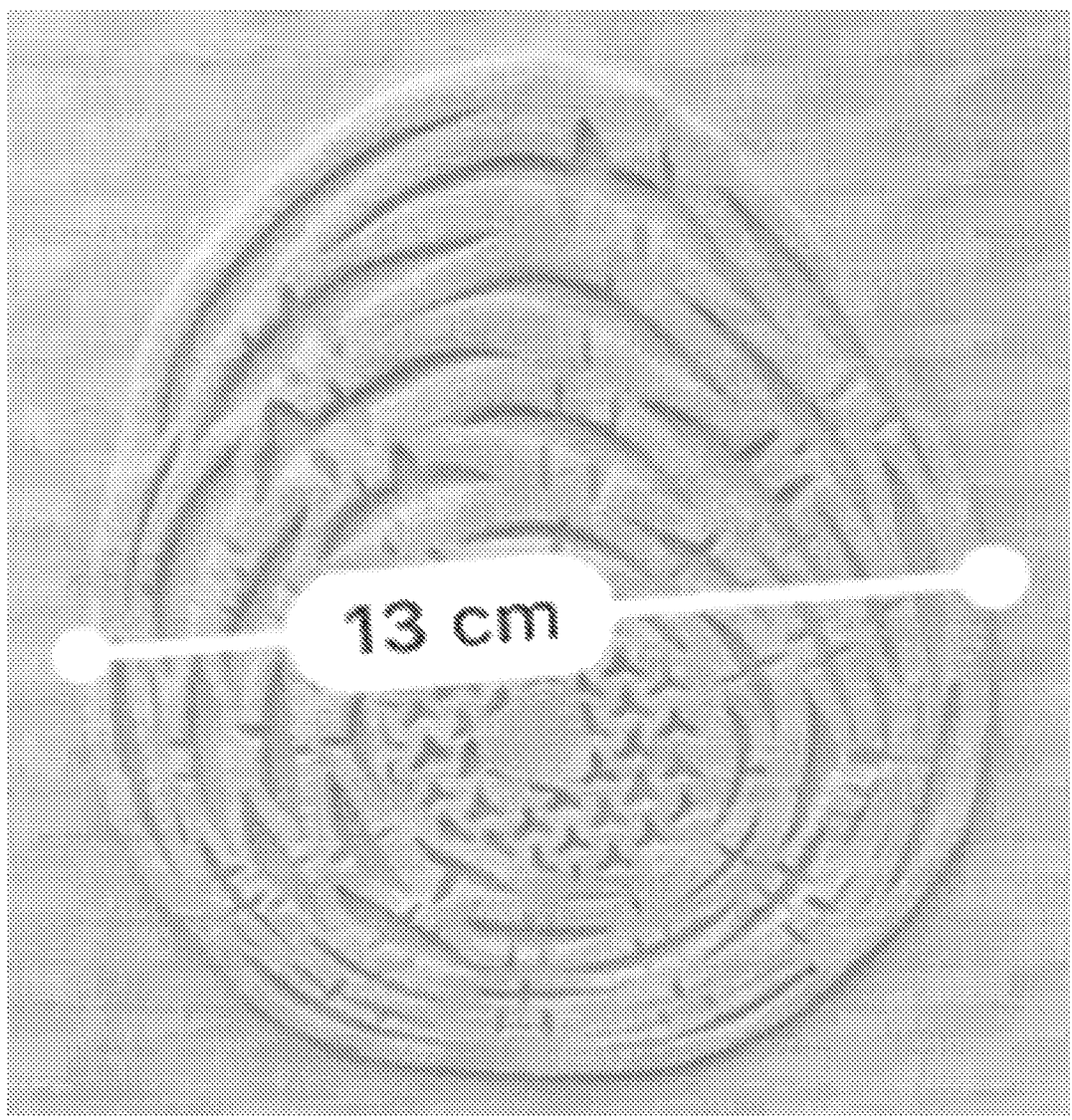
FIG. 26B provides an illustration of the substrate of FIG. 25A and FIG. 25B in an expanded form.
Figure 27:
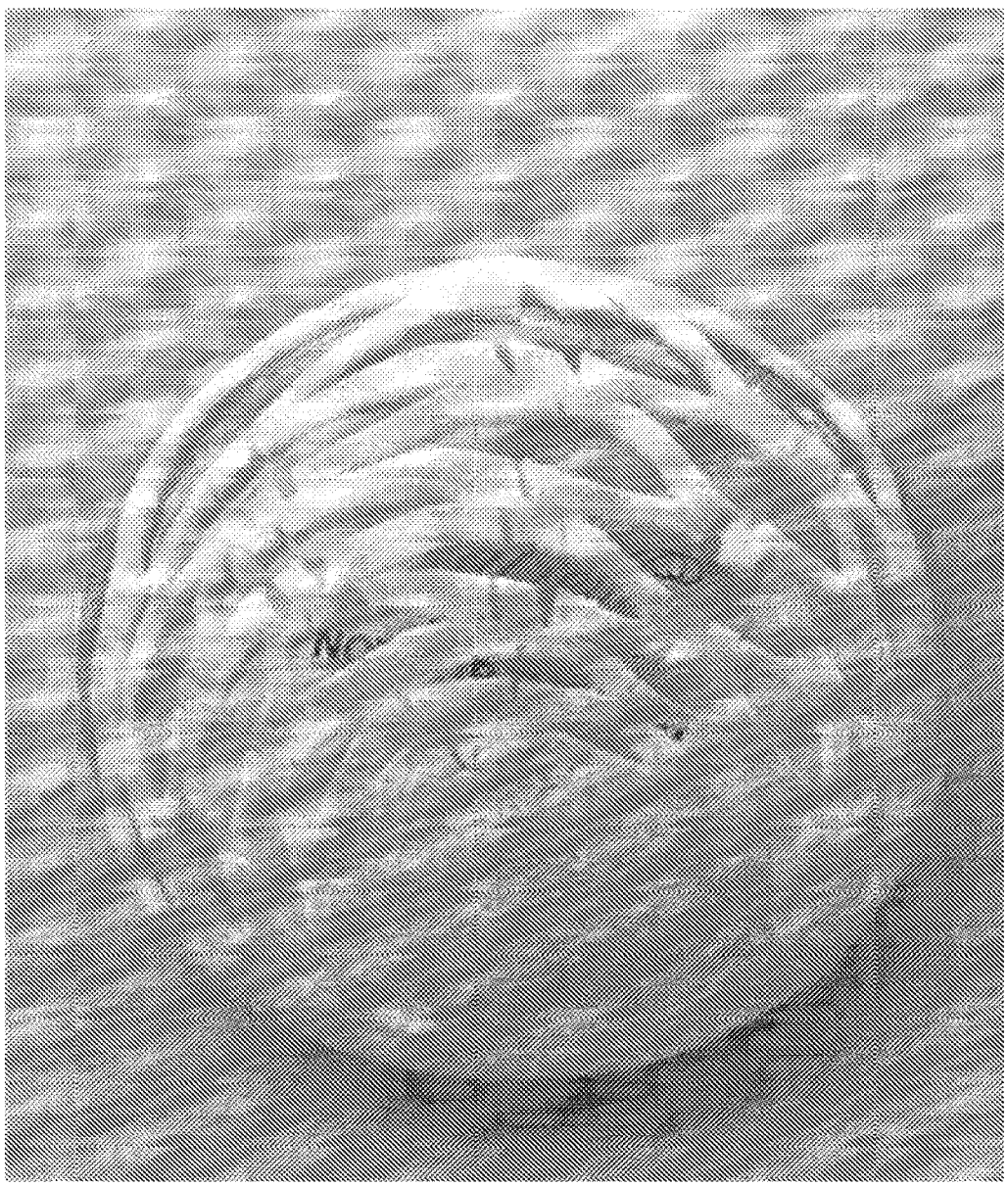
FIG. 27 provides a view of a spherical implant wrapped by the cut substrate of FIG. 26 and FIG. 26.

FIG. 25A and FIG. 25B provide an illustration of an exemplary pre-cut substrate in unexpanded form according to the present disclosure. As shown, the unexpanded cut substrate according to the present disclosure has a height of 12 cm (FIG. 25A) and a width of 8 cm (FIG. 25B), for a total coverage area of 96 cm². Upon application of minimal stretching, the cut substrate attains a height of 13 cm (FIG. 26A) and a width of 13 cm (FIG. 26B), for a total coverage area of 169 cm², a 76% increase over the coverage area in the unexpanded state. As shown, the 12 cm×8 cm substrate cut according to the present disclosure can enclose (FIG. 27) a 375 SCM implant. For comparison, a traditional, standard-of-care uncut substrate must be about 196 cm² in area to enclose a 375 SCM implant. This underscores the significant advantages presented by the disclosed technology, as the disclosed technology allows users to enclose a given implant using far less material that existing approaches.

Figure 28:
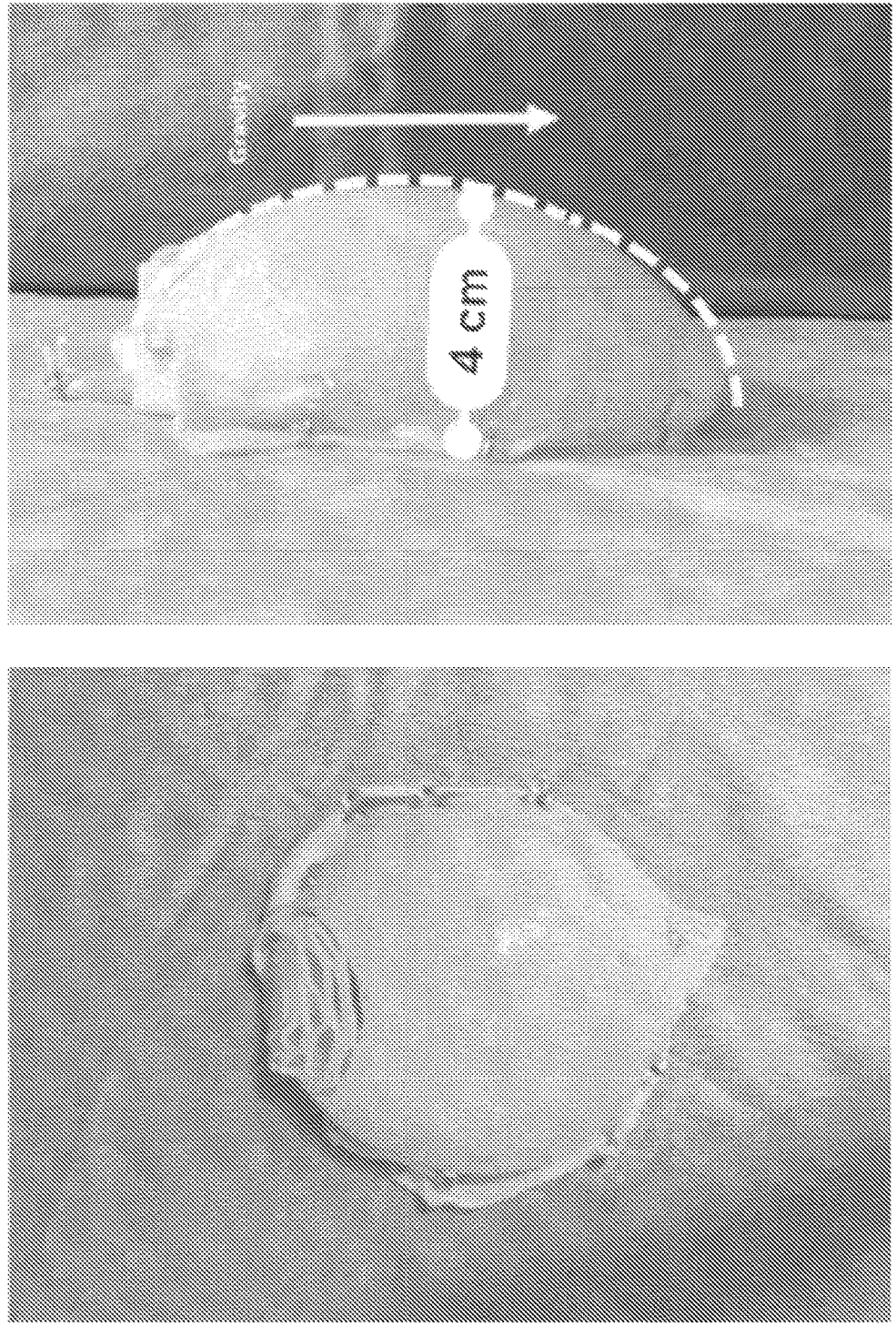

FIG. 28 provides views of a spherical implant wrapped by a substantially uncut substrate (the left panel is a view looking down at the wrapped implant when the implant is placed on a table; the right panel is a view looking sideways at the wrapped implant when the implant is mounted to a table that is tilted vertically so as to mimic the anatomic orientation of the implant in a patient who is standing and to show the effect of gravity). As shown, a spherical implant (left panel, showing implant resting on a table) that has a natural 4.3 cm projection and is enclosed by a traditional intraoperative device that essentially lacks any cuts has the same appx. 4 cm projection (and retains its spherical shape) when placed vertically (right panel; profile shown by dashed line for convenience) to simulate its anatomic position and to show the effect of gravity. Thus, the same projection occurs whether the placement is horizontal or vertical.

Figure 29:
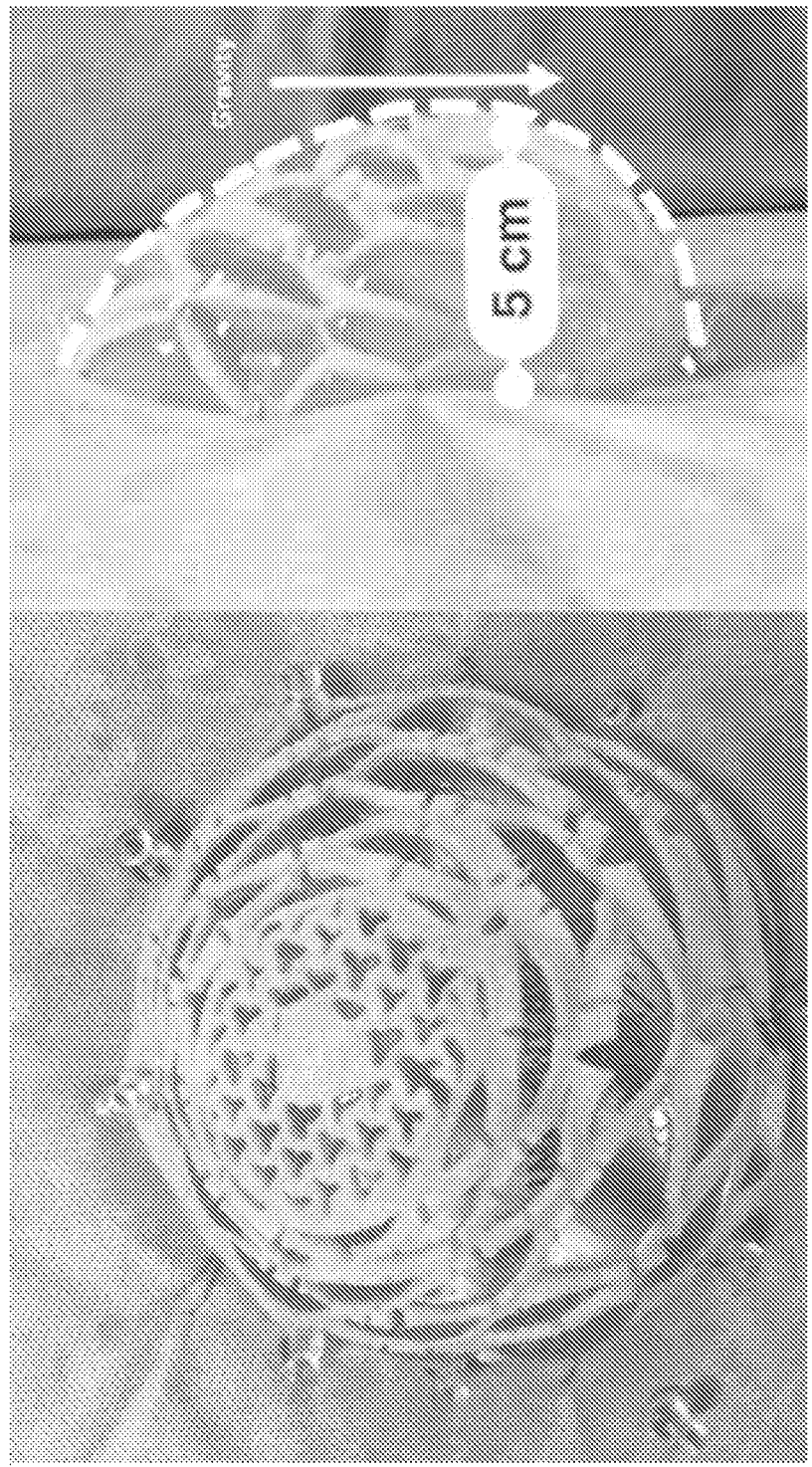
FIG. 29 provides views of a spherical implant wrapped by the cut substrate of FIG. 25 and FIG. 26 (the left panel is a view looking down at the wrapped implant when the implant is placed on a table; the right panel is a view looking sideways at the wrapped implant when the implant is mounted to a table that is tilted vertically so as to mimic the anatomic position of the implant in a patient who is standing)

FIG. 29 provides views of a spherical implant wrapped by a cut substrate according to the present disclosure. As shown in the left panel, the spherical implant retains its shape when placed horizontally and wrapped with a substrate cut according to the present disclosure. When mounted to a vertical surface (to simulate its anatomic position; right panel), however, the implant has a projection of 5 cm and also achieves a more natural teardrop-type shape (profile shown by dashed line for convenience), which can have advantages.

Figure 30:
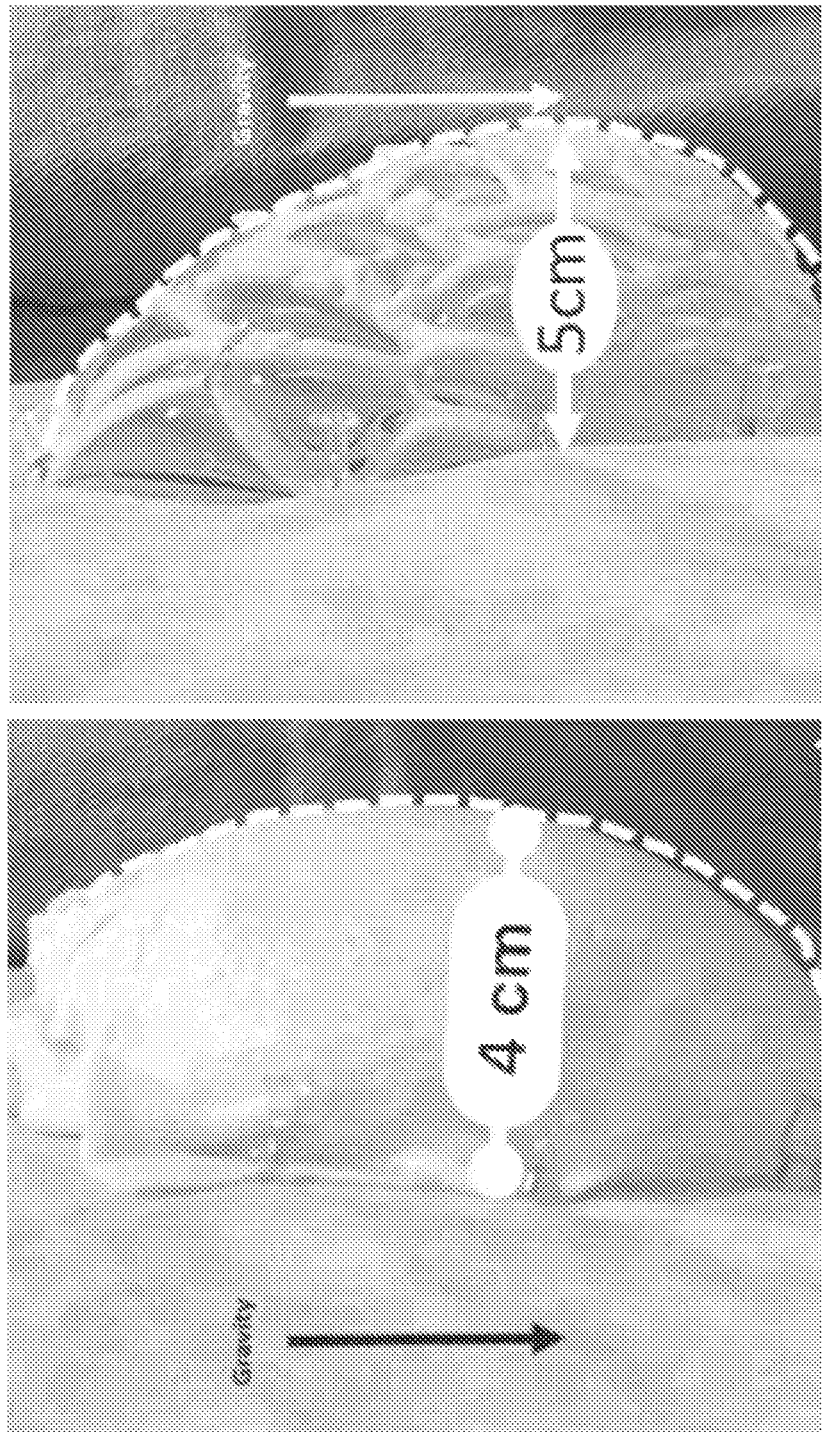
FIG. 30 provides views of a spherical implant wrapped by a substantially uncut substrate (left panel) and by a cut substrate according to the present disclosure (right panel) (in both the right and left panels, the implants are s mounted to a table that is tilted vertically so as to mimic the anatomic position of the implant in a patient who is standing and to explore the effect of gravity on the implant and wrap in that anatomic position)

FIG. 30 provides a comparison of the same spherical implant of FIG. 28 and FIG. 29. As shown, a spherical implant (left panel) that is mounted to a vertical surface to simulate anatomic position (and to show the effect of gravity) and is enclosed by a standard intraoperative device that is essentially free of any cuts retains its spherical shape (profile shown by dashed line for convenience) and has a projection of 5 cm. The same implant (right panel) when mounted to a vertical surface to simulate anatomic position (and to show the effect of gravity) and enclosed by a pre-cut intraoperative device according to the present disclosure has a projection of 5 cm and achieves a more natural teardrop-type shape (profile shown with dashed line for convenience As shown in FIG. 30, the implant when enclosed by a cut substrate according to the present disclosure exhibits an improved projection relative to the traditional approach and also achieves a more natural teardrop-type shape.

FIG. 31 provides an illustration of exemplary parameters used to characterized the disclosed technology. As shown, FIG. 31 provides variables for describing the configurations of substrate cuts in embodiments where the cuts are arranged, relative to one another, in a rectangular fashion, and in a circular fashion. Parameter $1c$ can describe the cut length (e.g., in a unique cut, but also in a periodic or repeating cut), parameter $1x$ can describe the distance between the ends of adjacent cuts as measured in an x-direction, and $1y$ can describe the distance between adjacent cuts as measured in a y-direction. ($1x$, $1y$, and $1c$ can be applied to characterize contour cuts.) Example tests were performed using Tyvek™ material.

Without being bound to any particulars, $1c/1y$ can be from about 0.1 to about 20, from about 0.2 to about 18, from about 0.5 to about 15, from about 1 about 9, from about 2 to about 8, from about 3 to about 7, or even from about 4 to about 6. $1c/1x$ can be from about 0.1 to about 20, from about 0.2 to about 18, from about 0.5 to about 10, from about 1 to about 9, from about 2 to about 8, from about 3 to about 7, or even from about 4 to about 6.

Figure 32:
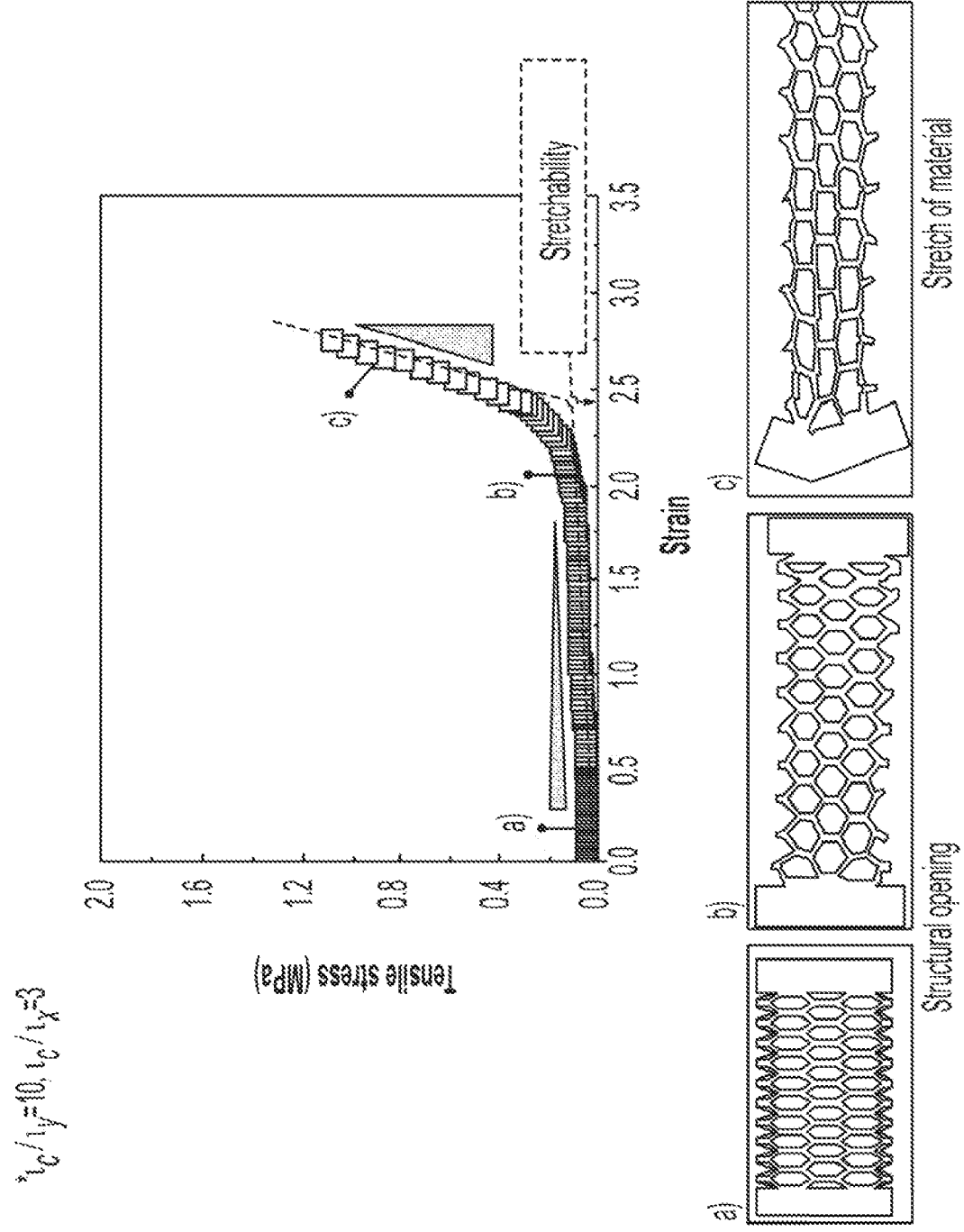
FIG. 32 provides exemplary results of the disclosed technology.

FIG. 32 provides exemplary results of the disclosed technology. As shown, tensile stress and strain vary as an example material (shown in panels, a, b, and c of FIG. 32) is opened by being expanded in the right-hand direction and then stretched as the end the example material is translated to the right. As shown, the example material could be expanded by a significant amount before tensile stress begins to increase. A stretchability characteristic can be defined by the slopes of the tensile stress line during expansion and stretching, as shown. As shown, a substrate according to the present disclosure can undergo structural opening (between panel a and panel b), followed by material stretching (between panel b and panel c). Without being bound to any particular theory, one may desire to form a substrate that undergoes significant structural opening (with little to no tensile stress) before tensile stress (and material stretching) sets in.

Figure 33:
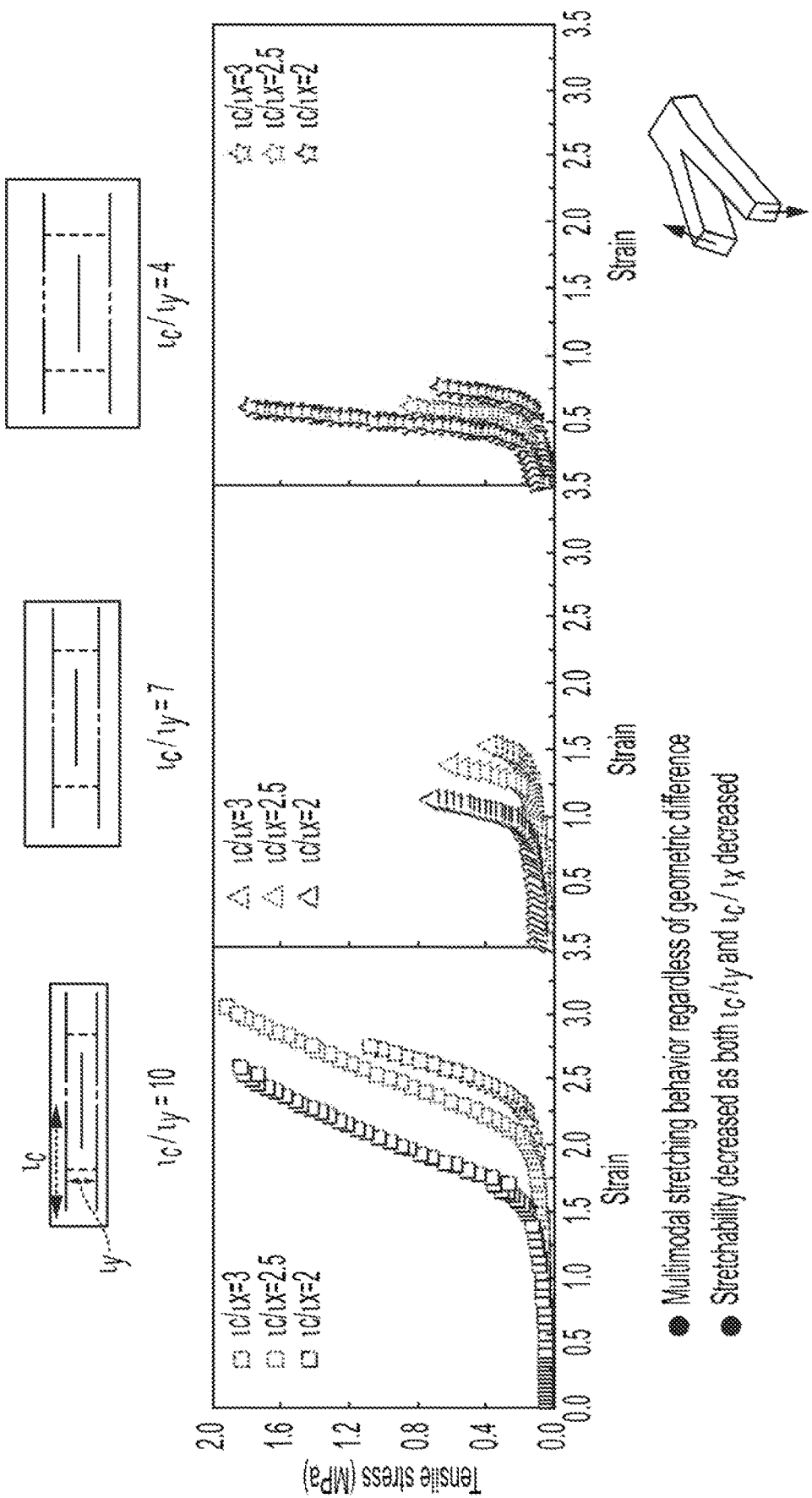
FIG. 33 provides exemplary results of the disclosed technology (in each of the three panels, 1c/1x=2 is the left hand data line, 1c/1x=2.5 is the middle data line, and 1c/1x=3 is the right hand data line)

FIG. 33 provides exemplary results of the disclosed technology (in each of the three panels, $1c/1x=2$ is the left-hand data line, $1c/1x=2.5$ is the middle data line, and $1c/1x=3$ is the right-hand data line). As shown, samples exhibited multimodal stretching behavior, regardless of geometric differences. Stretchability decreased as $1c/1y$ and $1c/1x$ decreased.

Figure 34:
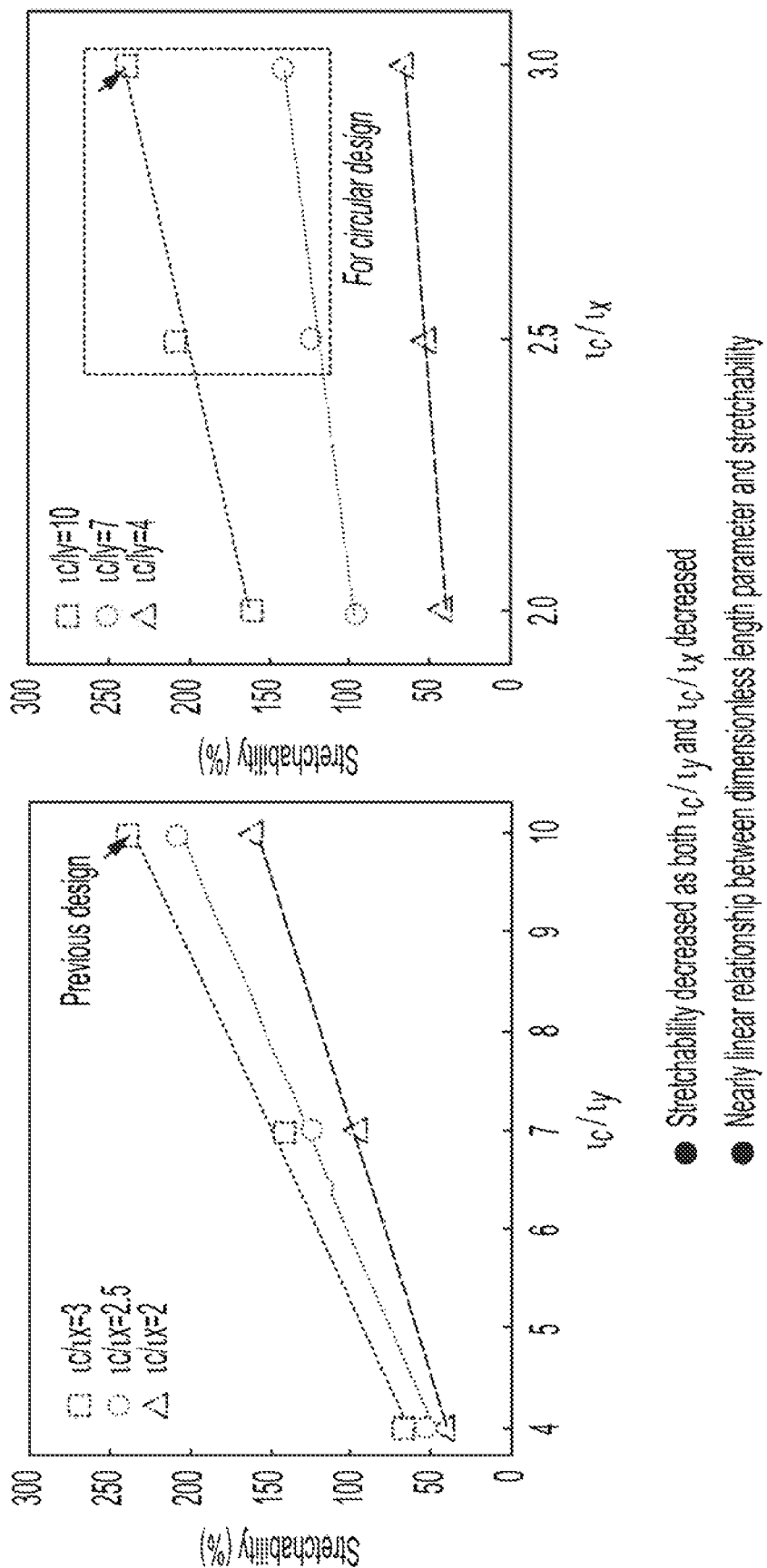
FIG. 34 provides exemplary results of the disclosed technology (in each of the three panels, 1c/1x=2 is shown by triangles, 1c/1x=2.5 is shown by circles, and 1c/1x=3 is shown by squares)

FIG. 34 provides exemplary results of the disclosed technology (in each of the three panels, $1c/1x=2$ is shown by triangles, $1c/1x=2.5$ is shown by circles, and $1c/1x=3$ is shown by squares). As shown, stretchability decreased as $1c/1y$ and $1c/1x$ decreased. Also as shown, there was a nearly linear relationship between the dimensionless length parameter ($1c/1x$ or $1c/1y$) and stretchability.

FIG. 35 provides exemplary embodiments of the disclosed technology. Shown in FIG. 35 are illustrations of circular-type contour cuts made at various $1c/1y$ and $1c/1x$ values.

Figure 36:
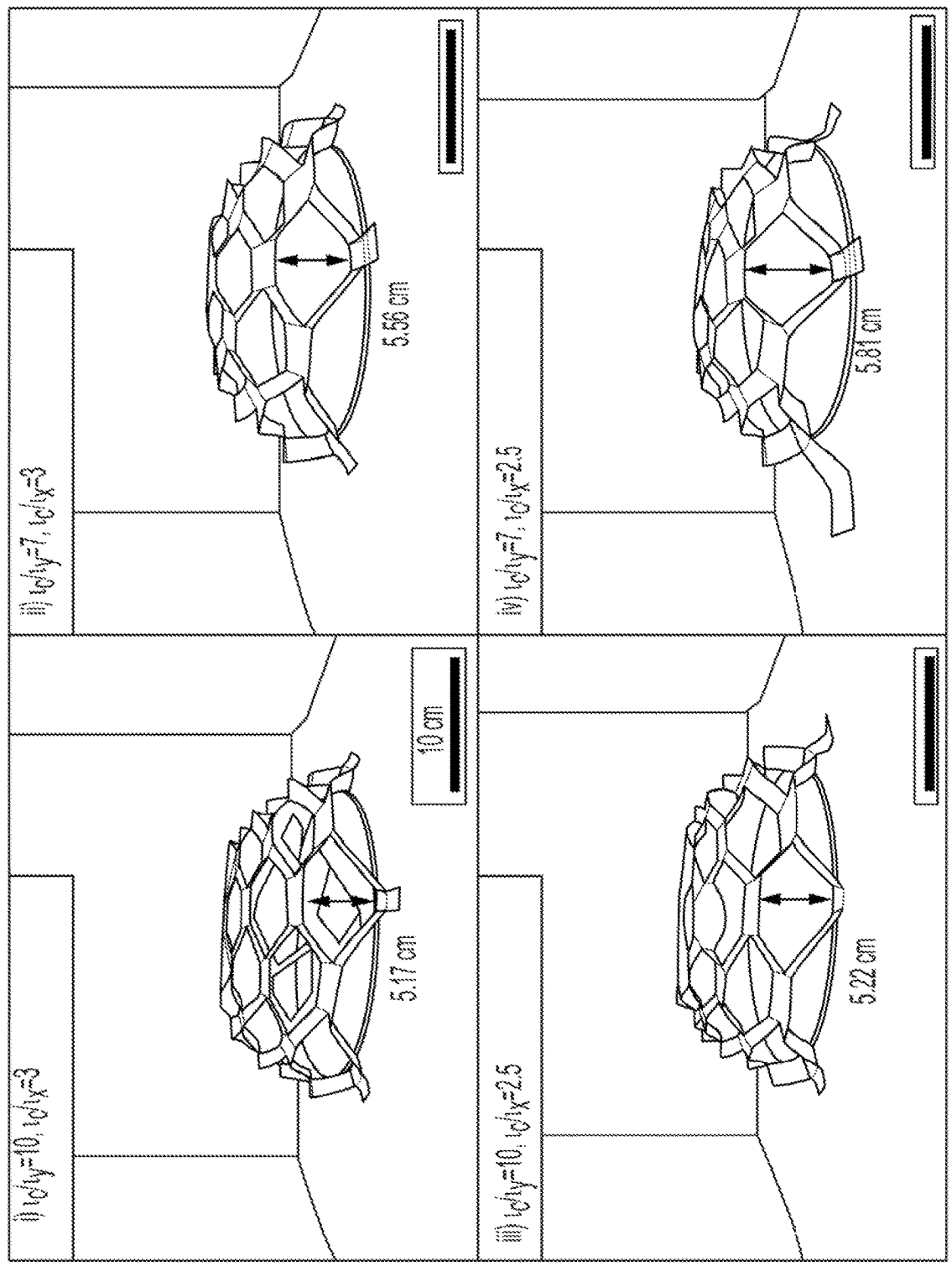
FIG. 36 provides exemplary embodiments of the disclosed technology.

FIG. 36 provides exemplary embodiments of the disclosed technology. As shown, substrates made according to the listed dimensionless length parameters defined in FIG. 35 were used to enclose an exemplary breast implant. As shown, certain length parameters resulted in enclosures that exhibited differently-sized spaces (as measured in the z-direction) between "ligaments" in the enclosing substrate.

Figure 37:
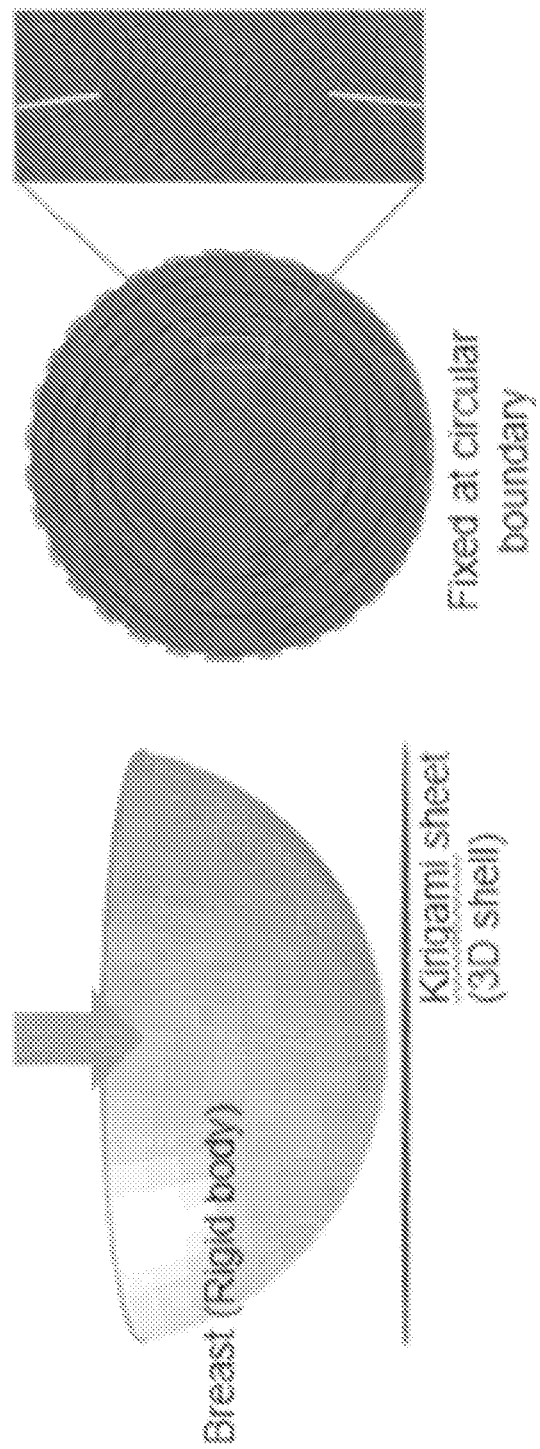
FIG. 37 provides exemplary testing conditions.

FIG. 37 provides exemplary testing conditions for testing non-limiting embodiments of the disclosed technology.

Figure 38:
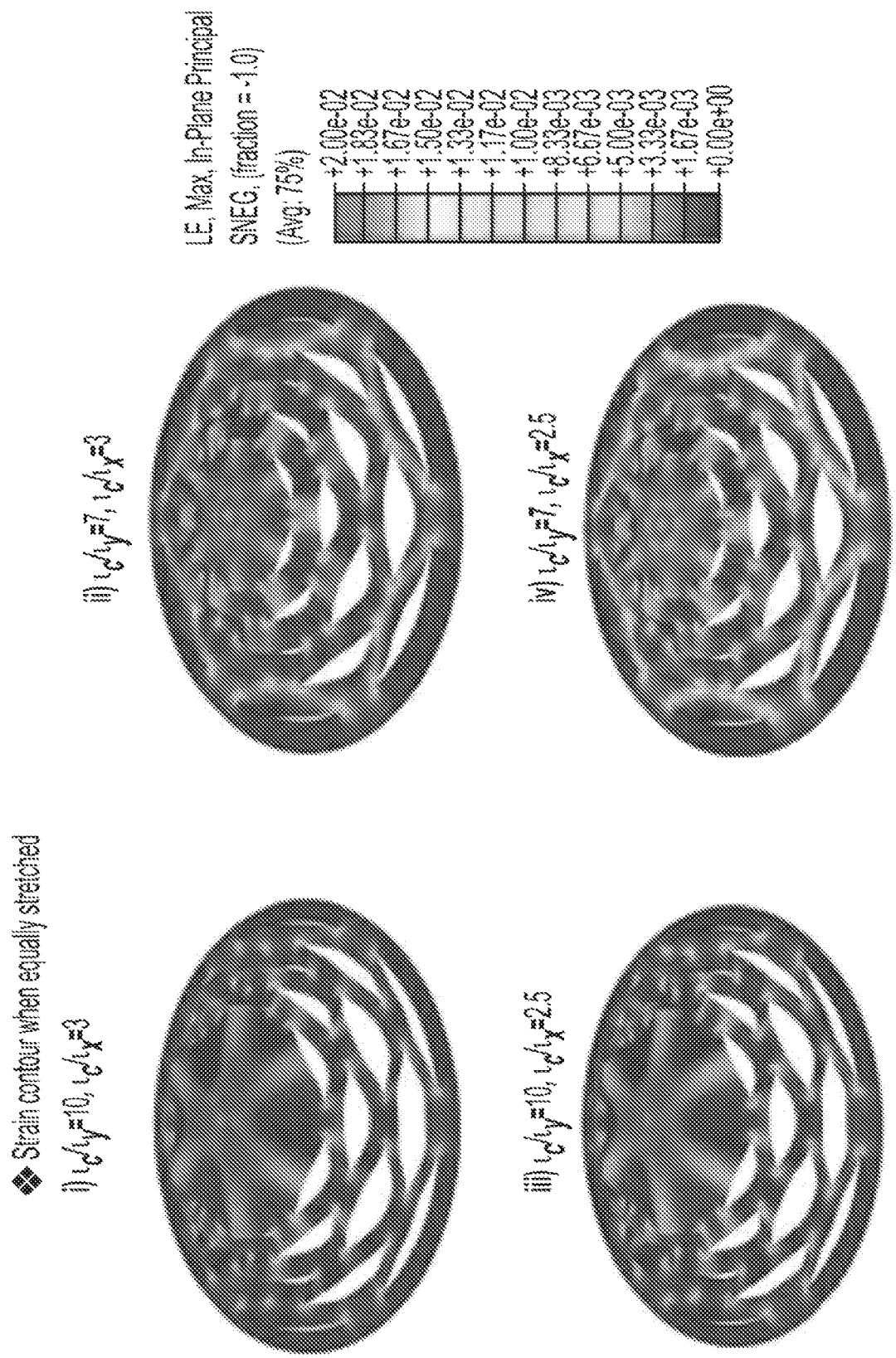
FIG. 38 provides exemplary finite element analysis results of the disclosed technology, showing strain concentration regions (cuts in the substrate), strain distribution, and buckling in the center of certain embodiments)

FIG. 38 provides exemplary strain contour results of the disclosed technology for substrates at various $1c/1x$ and $1c/1y$ values.

Figure 39:
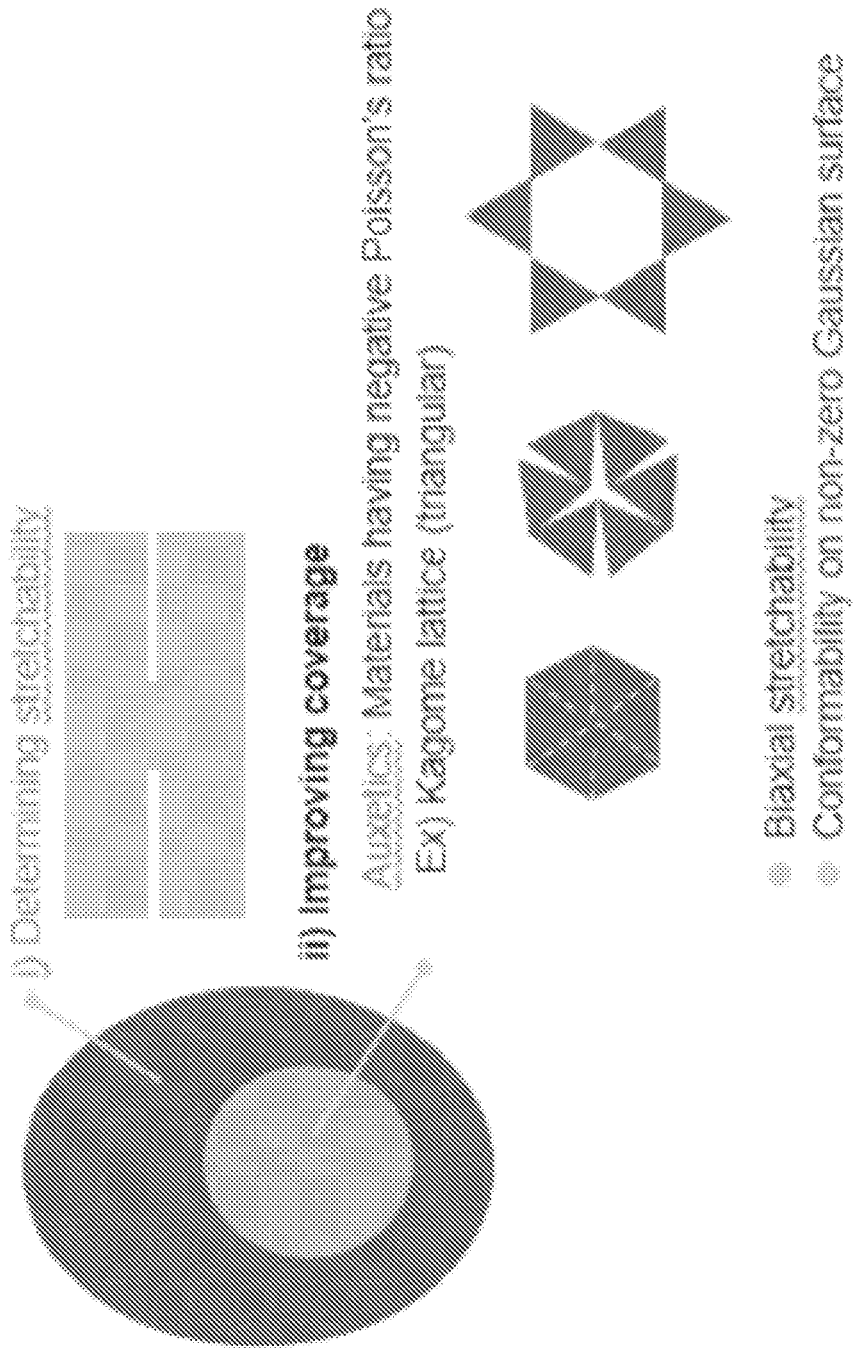
FIG. 39 provides exemplary embodiments of the disclosed technology.

FIG. 39 provides exemplary embodiments of the disclosed technology. As shown in FIG. 39 (and as described elsewhere herein), a substrate according to the present disclosure can include an auxetic region, which auxetic region can include cuts made in a fractal fashion. A substrate according to the present disclosure can include cuts that are arranged in a pattern that is characterized as triangular; cuts can also define a pattern that includes a chevron.

Figure 40:
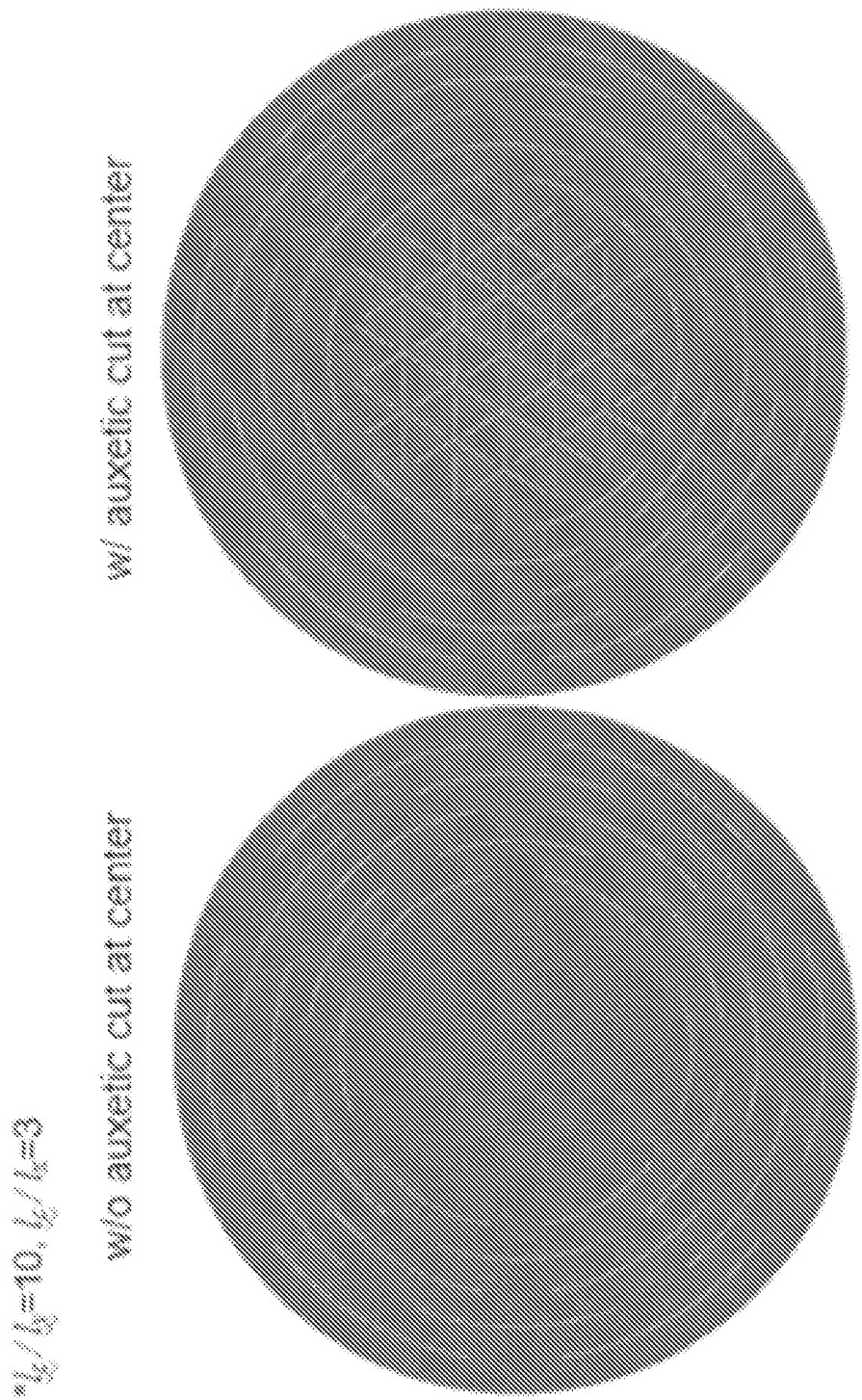
FIG. 40 provides exemplary embodiments of the disclosed technology.

FIG. 40 provides exemplary embodiments of the disclosed technology at the specified 1c/1y and 1c/1x values, within and without an auxetic region. As shown, periodic cuts can give rise to the auxetic region.

Figure 41:
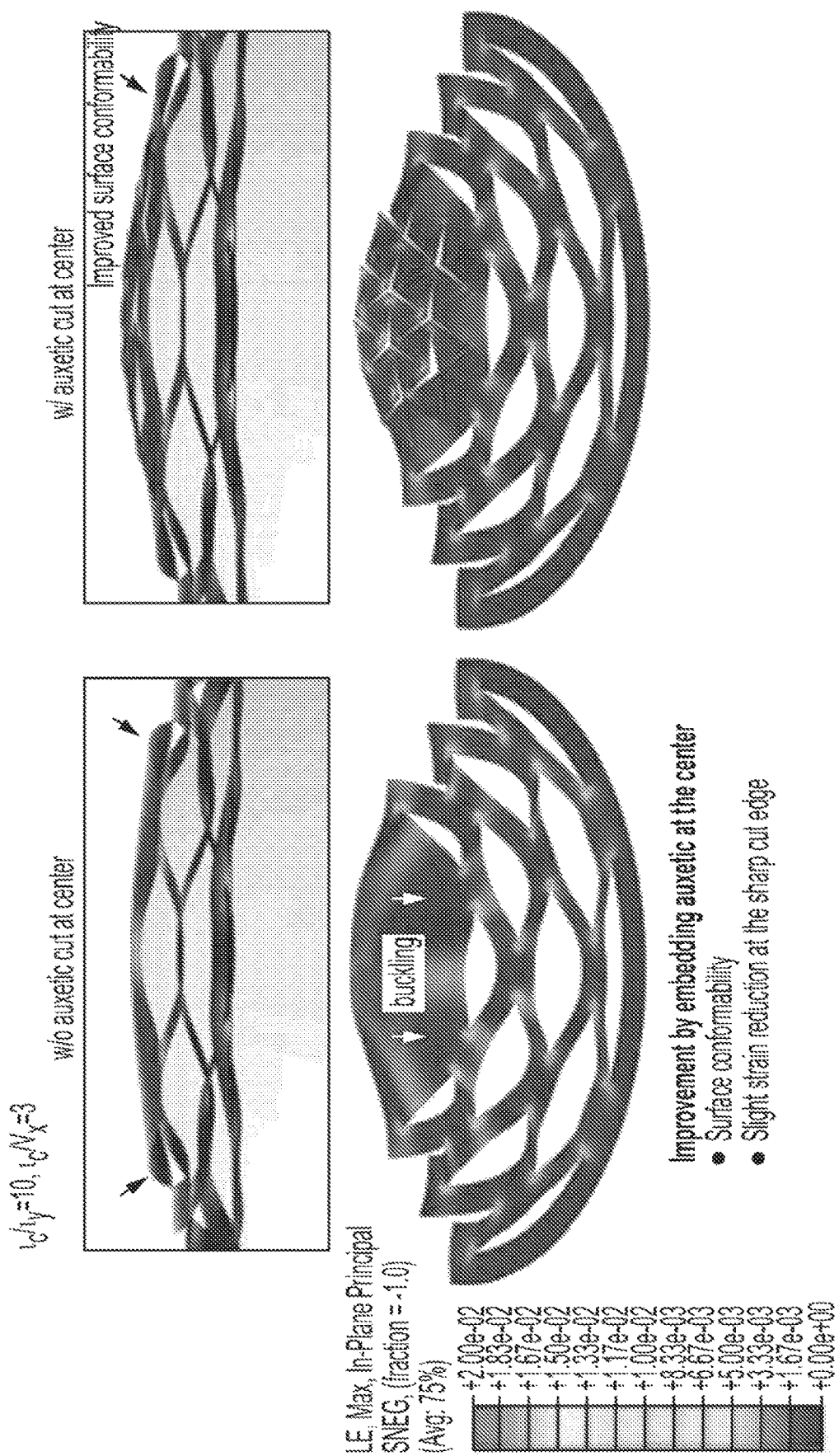
FIG. 41 provides exemplary finite element analysis results of the disclosed technology, showing strain concentration regions (cuts in the substrate), strain distribution, and buckling in the center of certain embodiments)

FIG. 41 provides exemplary results of the disclosed technology. As shown, when stretchability at the edge of a substrate increased, the effect of an auxetic region could be more significant. As shown, the presence of an auxetic region can also allow for increased coverage of a material being enclosed by the substrate, and can also allow for the substrate to better conform to the material being enclosed.

FIG. 42 provides exemplary embodiments of the disclosed technology at the specified 1c/1y and 1c/1x values, within and without an auxetic region. As shown, periodic cuts can give rise to the auxetic region.

Figure 43:
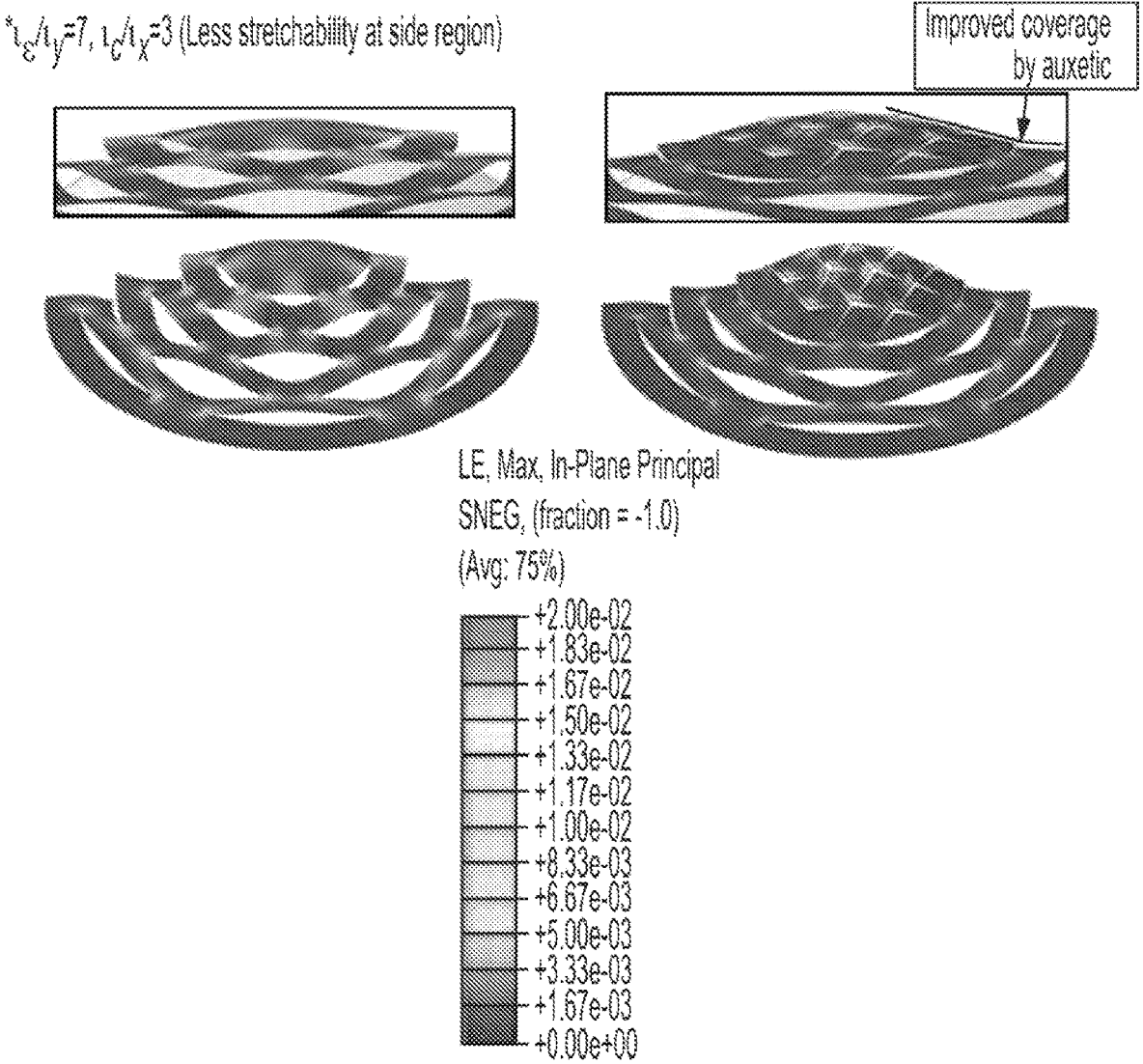
FIG. 43 provides exemplary finite element analysis results of the disclosed technology, showing strain concentration regions (cuts in the substrate), strain distribution, and buckling in the center of certain embodiments)

FIG. 43 provides exemplary results of the disclosed technology. As shown, when stretchability at the edge of a substrate increased, the effect of an auxetic region could be more significant. As shown, the presence of an auxetic region can allow for increased coverage of a material being enclosed by the substrate, and can also allow for the substrate to better conform to the material being enclosed.

Figure 44:
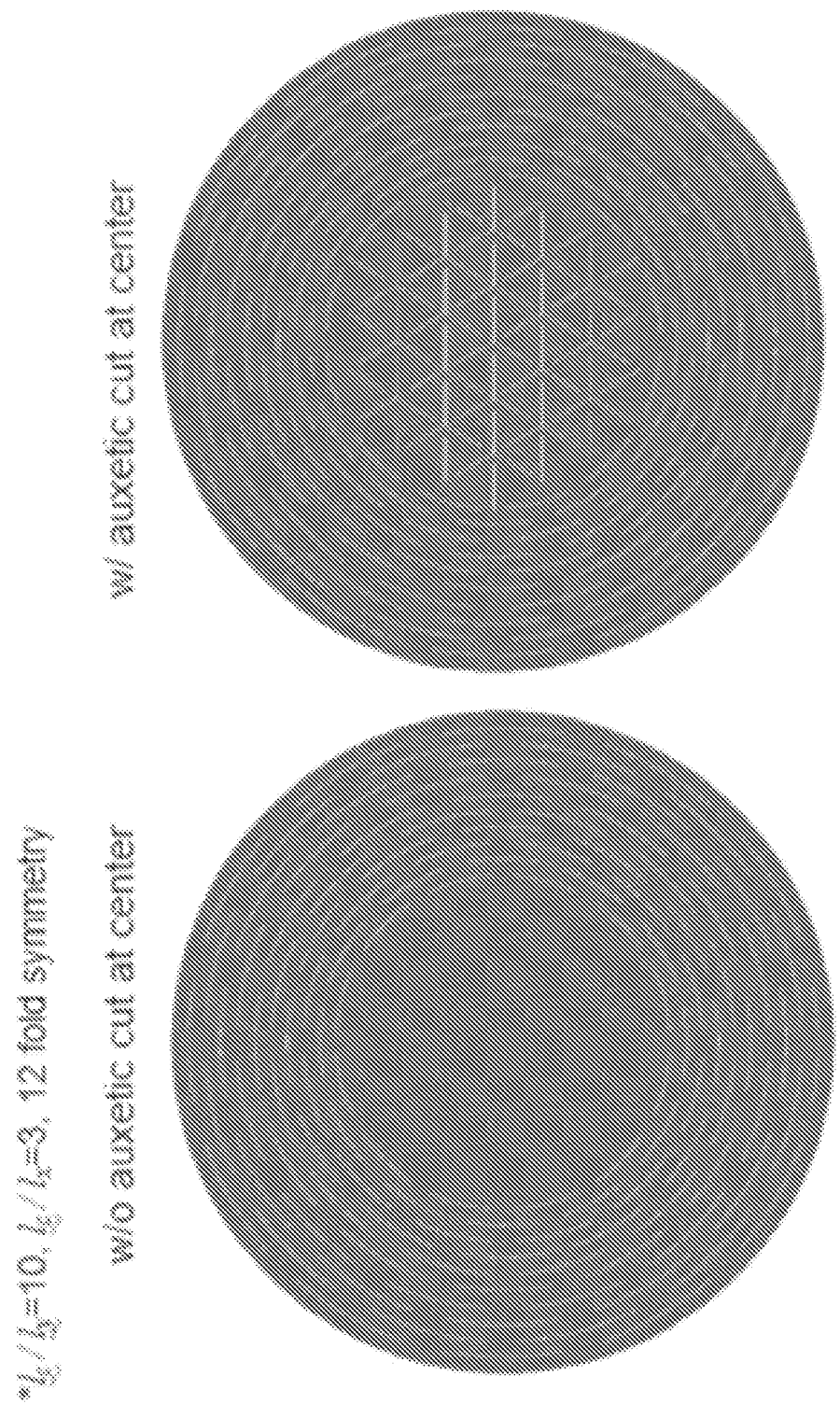
FIG. 44 provides exemplary embodiments of the disclosed technology.

FIG. 44 provides exemplary embodiments of the disclosed technology at the specified 1c/1y and 1c/1x values, within and without an auxetic region. As shown, periodic cuts can give rise to the auxetic region.

FIG. 45 provides exemplary embodiments of the disclosed technology. As shown, cuts can be formed in a fractal pattern. Cuts can also be formed in a branched fashion. As shown between the cuts illustrated in the "Level 1" pattern and the cuts in the "Level 2" pattern, cuts can be formed (Level 1) such that cuts radiate from a center point, e.g., at 120 degrees from one another, and these three-lined "stars" are arranged in a repeating pattern. As shown in Level 2, trunk cuts can be formed from a central point but can then have branch cuts emanating from the trunk cuts, and the trunk-branch "stars" can be arranged in a periodic pattern, e.g., a fractal pattern.

Also as shown in FIG. 45, a given cut can be a traditional-type cut that has a sharp edge; i.e., a rectangular cut. A cut can also, however, include a blunt edge, e.g., a circular, ovoid, or non-sharp edge or end. Without being bound to any particular theory, such a blunt cut can distribute stresses in a more dispersed way than a traditional cut that is rectangular or as a sharp edge or end.

Figure 46:
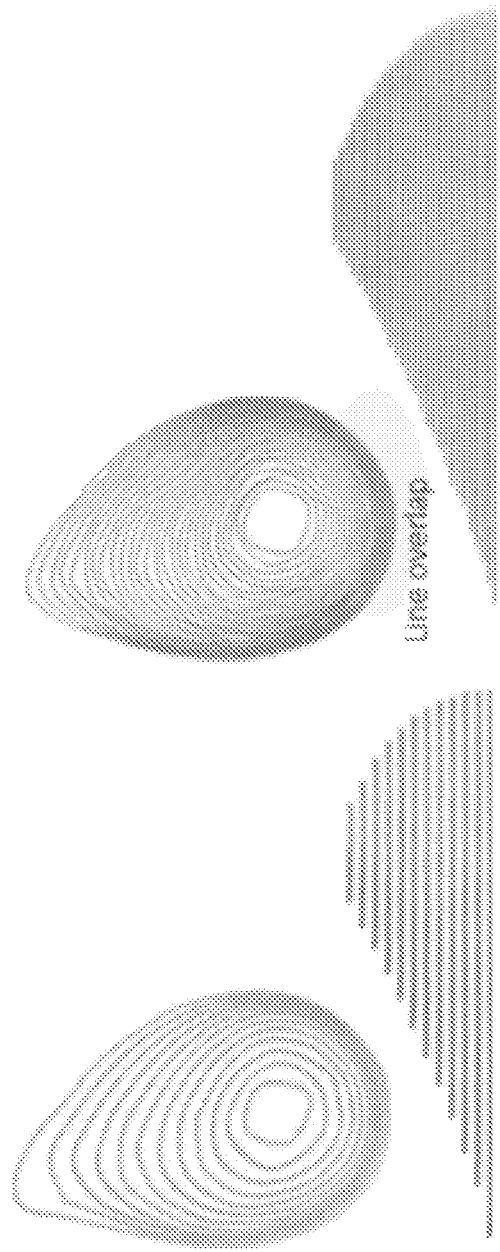
FIG. 46 provides exemplary embodiments of the disclosed technology.

FIG. 46 provides exemplary embodiments of the disclosed technology. As shown, FIG. 46 provides (upper left-hand image) a top view of a 3-D breast implant, showing contour lines. The lower left-hand image provides a side view of that breast implant, showing the stack of contour lines that represent different planes of the implant. As shown in the upper left-hand image, none of the contour lines overlap with one another.

The upper right hand image in FIG. 46 shows a breast implant with a higher density of contour lines, the higher density of contour lines giving rise to a region in which at least some of the lines overlap with one another. As shown in the lower right image in FIG. 46, the contour lines are more densely packed, as neighboring contour lines are relatively closer to one another.

FIG. 47 provides exemplary embodiments of the disclosed technology, again providing (left image) the substrate (and contour lines) of FIG. 46. As shown in FIG. 47, when contour lines that are only a certain distance apart from one another are projected onto a substrate and then cuts are formed according to those contour lines, the projected cut lines can overlap with one another on the substrate.

FIG. 48 provides exemplary embodiments of the disclosed technology. As shown, a substrate can comprise (left image) contour cut lines, an auxetic region, and hierarchical contour cut lines that intersect the contour cut lines. Alternatively, a substrate can include only contour lines and be free of hierarchical contour cut lines.

FIG. 49 provides exemplary embodiments of the disclosed technology, providing (left hand) a substrate that includes an auxetic region and (right hand) a substrate that includes a relatively larger auxetic region.

As shown in FIG. 49, the density of contour lines (not labeled) can vary at different circumferential locations around a substrate. As shown, the density (i.e., number of contour lines per unit length) of contour lines along line A/A1 that radiates outward from a point on the substrate can be different that the density of contour lines along line B/B1 that radiates outward from a point on the substrate, with lines A/B and A1/B1 being offset from one another by angle α. Further, the density of contour lines can vary along a given line that radiates outward from a point on the substrate. As shown, along line B in a direction away from the center of the substrate, the contour lines are less dense closer to the center, and more dense further away from the center. (It should be understood that the foregoing description of contour line densities can apply to any embodiment of the disclosed technology.)

Figure 50:
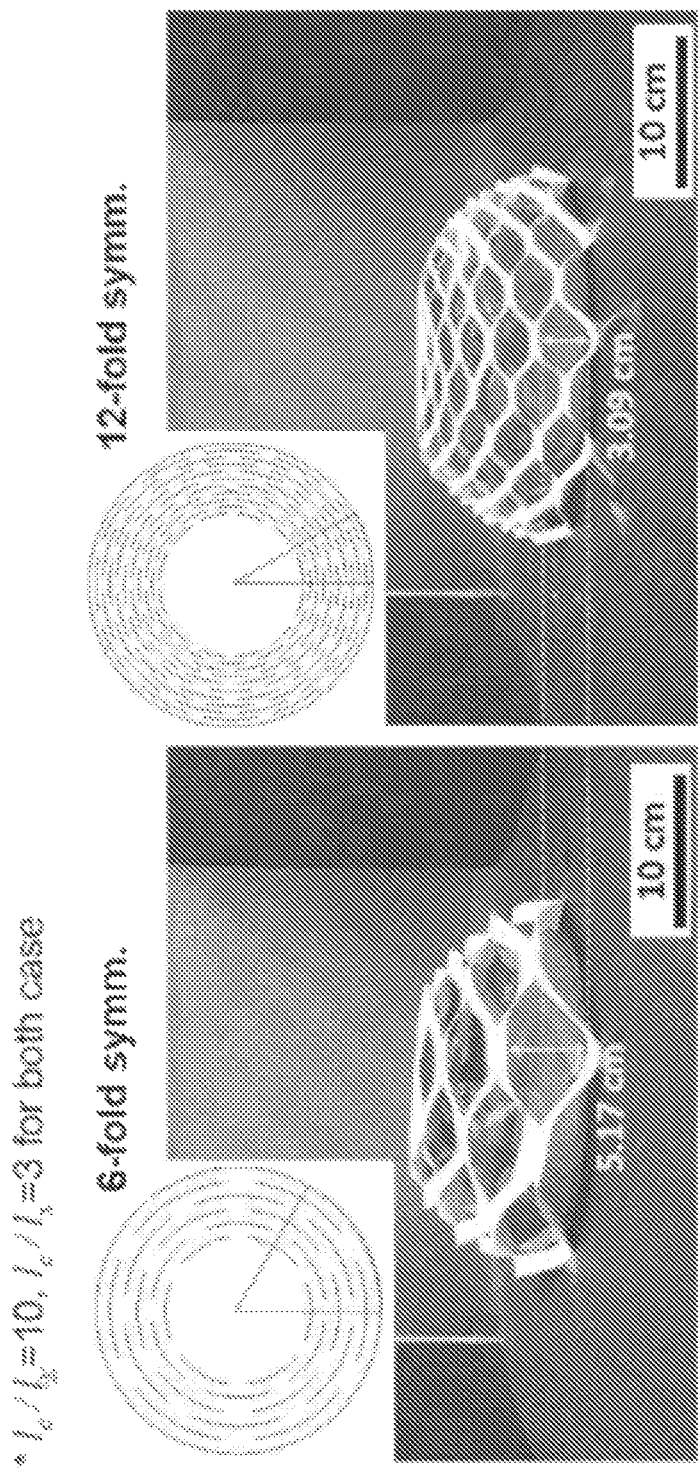
FIG. 50 provides exemplary embodiments of the disclosed technology

FIG. 50 provides an exemplary embodiment of the disclosed technology. As shown, a cut substrate can comprise unit cells (shown in FIG. 50 by pie slice-shaped lines) that repeat in a circumferential direction around the substrate. As one example, a substrate can be a substrate that exhibits a 6-fold symmetry, in which case there are six identical unit cells arrayed circumferentially around the substrate, e.g., each unit cell spans 360/6=60 degrees. As another example, a substrate can exhibit a 12-fold symmetry such that each unit cell spans 360/12=30 degrees. A substrate according to the present disclosure can have multi-fold symmetry. Symmetry in the substrate, however, is not a rule or requirement.

EXEMPLARY EMBODIMENTS

The following embodiments are illustrative only and do not necessarily limit the scope of the present disclosure or the appended claims.

Embodiment 1. An intraoperative device, comprising: a substrate having a plurality of discontinuous cuts formed therein, the plurality of discontinuous cuts being formed such that when the substrate is subjected to deformation, the substrate is capable of deformation beyond an initial state so as to achieve a first shaped three-dimensional (3D) state. As described elsewhere herein, the disclosed devices and methods are applicable to autologous tissue transfer procedures, to breast implant/prosthesis procedures, and to other surgical procedures.

The substrate can comprise one or more materials. Materials that are cut-able are considered especially suitable, e.g., surgical meshes and the like. Polymeric materials are also considered suitable. The cuts can be symmetric or asymmetric in configuration. In some embodiments, cuts are self-symmetric, i.e., a cut is symmetric along a line drawn along the cut.

In some embodiments, cuts are positioned so that one or more cuts is symmetric (i.e., along a line drawn along the substrate) to one or more other cuts. Cuts can be arranged in a circumferential fashion, but this is not a requirement, as those of ordinary skill in the art will arrive at the cut pattern, shape, and size that is suited for their particular use.

Relative to the total possible surface area of an uncut substrate (i.e., "starting" substrate that has not yet been cut and is free of cuts), cuts can from about 0.1 to about 90% of that total possible surface area, e.g., from about 0.1 to about 90%, from about 1 to about 90%, from about 5 to about 80%, from about 10 to about 70%, from about 20 to about 60%, or even from about 30 to about 50% of that total possible surface area. (As an example, for a square substrate that has edges of 10 cm and 10 cm, the total possible surface area of that substrate is 100 cm$^2$.)

In some embodiments, the ratio of the surface area of the substrate to the "void" area of the cuts formed in the substrate is from 1:100 to 100:1, or from about 1:50 to 50:1, or from about 1:25 to 25:1, or from about 1:10 to about 10:1, or from about 1:5 to 5:1, or even from about 1:2 to 2:1.

The first 3D state can define a height of from more than the thickness of the substrate to about, e.g., 1 cm, 2, cm, 3, cm, 4 cm, 5 cm, 6 cm, 7 cm, 8 cm, 9 cm, 10 cm, or greater. A 3D state can comprise one or more bends, curves, concavities, convexities, and the like. A 3D state can have an aspect ratio (e.g., height to width or length) of from about 1:100 to about 1:1, 1:2, 1:5, 1:10, or even greater. The thickness of the substrate can be constant or can be variable. A substrate can define a thickness of, e.g., from about 0.1 mm to about 5 mm, or from about 0.5 mm to about 4 mm, or even from about 1 mm to about 3 mm. (The foregoing thicknesses are illustrative only and are not limiting.)

A substrate can include one or more perforations, score lines, tabs, slots, or and the like to facilitate the shaping of the substrate. As one example, a substrate can include one or more score lines to facilitate bending of the substrate. A score line can be straight or curved.

A substrate can even include one or more tearaway portions or one or more portions that can be detached. For example, a substrate can include a wing that is attached by two bridges to the rest of the substrate. One or both of the bridges can include a score line or even a tearaway portion so as to allow for bending or even removal of the wing.

Embodiment 2. The intraoperative device of Embodiment 1, wherein the discontinuous cuts are formed such that when the substrate is in the first shaped state, the substrate comprises a first region having a first stretchability and/or elasticity and a second region having a second stretchability and/or elasticity, the first stretchability (and/or elasticity) and the second stretchability (and/or elasticity) being different from one another. It should be understood, however, that devices can be uniform or isotropic in terms of rigidity, elasticity, and/or elasticity.

Embodiment 3. The intraoperative device of any of Embodiments 1-2, wherein the discontinuous cuts are formed such that when the substrate is in the first shaped state, the substrate comprises a first region having a first rigidity and a second region having a second rigidity, the first rigidity and the second rigidity being different from one another. It should be understood that a substrate can be selected and/or configured such that the substrate is deformable by hand.

Embodiment 4. The intraoperative device of any of Embodiments 1-3, wherein the initial state of the substrate is a planar state. The initial state of a substrate can have perimeter that is square, but this is not a requirement, as a substrate can have a perimeter that is polygonal, circular, oblate (e.g., elliptical), or even irregular in perimeter.

Embodiment 5. The intraoperative device of any of Embodiments 1-4, wherein one or more discontinuous cuts is characterized as a gap. A gap can be rectangular, spherical, polygonal, triangular, circular, or tapered in shape in some embodiments. It should be understood that a gap can be of any shape or length, as a gap's size can depend on the needs of a user. A gap can have a cross-sectional dimension of from, e.g., about 0.1 to about 10 mm and all intermediate values.

Embodiment 6. The intraoperative device of any of Embodiments 1-5, wherein, at least some of the discontinuous cuts are symmetric to one another across a line crossing at least a portion of the substrate. As one example, cuts can be distributed like the six dots on the "6" face of a die.

Embodiment 7. The intraoperative device of any of Embodiments 1-6, wherein the substrate defines a perimeter.

Embodiment 8. The intraoperative device of Embodiment 7, wherein a length of the perimeter or the shape of the perimeter is based, at least in part, on one or more measurements or estimates of a subject's anatomy. The shape of the device can be selected such that the device, in its deployed state, conforms to tissue of a particular size and/or shape. This can be accomplished by taking actual measurements of a patient's tissue; it can also be accomplished by generating estimates of a patient's tissue.

Embodiment 9. The intraoperative device of any of Embodiments 1-8, wherein a dimension of at least one discontinuous cut is based, at least in part, on one or more measurements or estimates of a subject's anatomy.

Embodiment 10. The intraoperative device of any of Embodiments 1-9, wherein a position of at least one discontinuous cut is based, at least in part, on one or more measurements or estimates of a subject's anatomy.

Embodiment 11. The intraoperative device of any of Embodiments 1-10, wherein the substrate comprises a mesh. Some or all of a substrate can be mesh in configuration. The perforations/holes in the mesh can be of various sizes, e.g., from about 0.01 mm to about 1 mm, in some non-limiting embodiments. Larger and smaller mesh openings can be used.

Embodiment 12. The intraoperative device of any of Embodiments 1-11, wherein the substrate comprises one or more pores, perforations, or both. Apertures formed in the substrate can be cylindrical, conical, or even tortuous in configuration.

Embodiment 13. The intraoperative device of any of Embodiments 1-12, wherein the substrate is characterized as bio-absorbable, bio-degradable, bio-resorbable, non-bio-absorbable, non-bio-degradable, non-bio-resorbable, or any combination thereof. As one example, a substrate can include a bio-degradable region and a non-biodegradable region.

Suitable bio-absorbable materials will be known to those in the art. One can select a bio-absorbable material based on the ability of the material to absorb relatively slowly such that the device supports the tissue at issue until the healing is at least substantially complete and the device is not fully absorbed before that time.

Embodiment 14. The intraoperative device of any of Embodiments 1-12, wherein the substrate is characterized as bio-compatible. As described elsewhere herein, acellular dermal matrix materials are considered especially suitable as substrates for the disclosed technology. It should be understood, however, that acellular dermal matrix materials are not the only suitable substrates for the disclosed technology.

Embodiment 15. The intraoperative device of any of Embodiments 1-12, wherein the substrate is characterized as non-bio-absorbable. In some embodiments, the user can desire a substrate material that is not bio-absorbable, e.g., in applications where the user can desire the substrate to provide permanent support to the tissue being supported.

Embodiment 16. The intraoperative device of any of Embodiments 1-15, wherein the first shaped three-dimensional state is characterized as concave.

Embodiment 17. The intraoperative device of any of Embodiments 1-15, wherein the first shaped three-dimensional state is characterized as an envelope. As one example, an envelope can be a configuration that comprises more of a sphere than a hemisphere. An envelope need not be (hemi)spherical in configuration, however, and can be polygonal, capsule-shaped, lozenge-shaped, or be of virtually any other such shape.

Embodiment 18. The intraoperative device of any of Embodiments 1-15, wherein the first shaped three-dimensional state is characterized as being at least partially circular.

Embodiment 19. The intraoperative device of any of Embodiments 1-18, further comprising a medicament disposed on the substrate. Medicaments can include, e.g., anti-rejection drugs, anti-coagulants, immunosuppressants, and the like.

Embodiment 20. The intraoperative device of any of Embodiments 1-19, wherein the first shaped three-dimensional state is characterized as conforming to at least a portion of a breast.

Embodiment 21. The intraoperative device of any of Embodiments 1-20, wherein the intraoperative device is configured to maintain the first shaped three-dimensional state. Without being bound to any particular theory or configuration, the device can be engineered to include some hysteresis and/or shape memory, e.g., similar to memory wire.

Embodiment 22. The intraoperative device of any of Embodiments 1-20, wherein the intraoperative device is capable of maintain the first shaped three-dimensional state with usage of a single affixation, e.g., a suture or a region of adhesive. Multiple sutures and/or adhesive regions can of course be used.

In some embodiments, the device can include a feature (e.g., a tab, a slot, a wire, a thread, a loop, a cinch, and the like) that is used to secure the device to a subject, to secure the device into a particular configuration/shape, or to otherwise secure the device.

Embodiment 23. The intraoperative device of any of Embodiments 1-20, further comprising a suture positioned to maintain the intraoperative device in the first shaped three-dimensional state.

It should be understood that the present disclosure includes devices according to the disclosure disposed about a subject's tissue and/or a prosthesis, e.g., a breast prosthesis.

Embodiment 24. A method, comprising implanting a device according to any of Embodiments 1-23 into a subject. As one example, one can use a device according to the present disclosure to at least partially enclose and support autologous tissue (e.g., abdominal musculature) of a subject undergoing reconstructive breast surgery that is then transplanted into the chest area of the subject. A user can also use a device according to the present disclosure to at least partially enclose and support a breast prosthesis or other implantable item.

Embodiment 25. A method, comprising contacting the tissue of a subject to an intraoperative device according to any of Embodiments 1-23. The methods can further comprise at least partially conforming the intraoperative to the tissue, e.g., by bending and/or folding. The methods can additionally include affixing (e.g., via suture and/or glue) one portion of the intraoperative device to another portion of the intraoperative device and/or to the tissue). The methods can further comprise affixing the intraoperative device to a location (e.g., chest wall) of a subject.

The tissue can be breast tissue, but this is not a requirement, as the disclosed technology is not limited to breast tissue or to breast-related applications. The disclosed devices can be used in other surgical applications, e.g., bladder support, organ transplantation, grafts, orthopedic procedures, and the like.

Embodiment 26. The method of Embodiment 25, further wherein the intraoperative device is in a first shaped three-dimensional state.

Embodiment 27. The method of any of Embodiments 25-26, further comprising disposing the intraoperative device and the tissue into a subject.

Embodiment 28. A method, comprising contacting a prosthesis to an intraoperative device according to any of Embodiments 1-23.

The methods can further comprise at least partially conforming the intraoperative device to the prosthesis, e.g., by bending and/or folding. The methods can additionally include affixing (e.g., via suture and/or glue) one portion of the intraoperative device to another portion of the intraoperative device (and/or to the tissue). The methods can further comprise affixing the intraoperative device to a location (e.g., chest wall) of a subject.

A prosthesis can be, e.g., a breast prosthesis. Other prostheses (e.g., other cosmetic prostheses) can be used. The disclosed devices can be used in other surgical applications, e.g., bladder support, organ transplantation, grafts, orthopedic procedures, and the like.

Embodiment 29. The method of Embodiment 28, further wherein the intraoperative device is in a first shaped three-dimensional state.

Embodiment 30. The method of any of Embodiments 28-29, further comprising disposing the intraoperative device and the prosthesis into a subject.

Embodiment 31. A template, comprising: a stencil pattern configured to overlay a substrate, the stencil being configured such that cutting the substrate in accordance with the stencil pattern gives rise to an intraoperative device according to any of Embodiments 1-23.

Embodiment 32. The template of Embodiment 31, wherein the stencil pattern is based, at least in part, on one or more measurements or estimates of a subject's anatomy.

Embodiment 33. A method, comprising: forming a plurality of discontinuous cuts in a substrate such that when the substrate is subsequently subjected to deformation, the substrate is capable of deformation beyond an initial state so as to achieve a first shaped three-dimensional state.

Embodiment 34. A method, comprising: defining a plurality of contour lines on a substrate in an initial state, the contour lines corresponding to planes in a first shaped three-dimensional state of the substrate, the planes being parallel to one another and being normal to a direction Z that is normal to the substrate in the initial state defining a plurality of guide lines emanating from an origin point on the substrate; forming a cut through the substrate along a contour line so as to give rise to a contour cut between an intersection of the contour line with a first guide line and an intersection of the contour line with a second guide line that is adjacent to the first guide line, the cut being performed such that when the substrate is subjected to deformation, the substrate is capable of deformation beyond an initial state so as to achieve a first shaped three-dimensional state.

Embodiment 35. The method of claim 34, wherein the cutting is performed such that when the substrate is subjected to deformation, the substrate comprises a region having a first stretchability and/or elasticity and/or rigidity in the direction Z and a second region having a second stretchability and/or elasticity and/or rigidity in the direction Z that differs from the first stretchability and/or elasticity and/or rigidity.

Embodiment 36. The method of claim 35, wherein the cutting is performed such that when the substrate is subjected to deformation, the substrate comprises a region having a first elasticity in the direction Z and a second region having a second elasticity in the direction z that differs from the first elasticity.

Embodiment 37. The method of any one of claims 34-36, further comprising forming a cut through the substrate in a direction perpendicular to the contour cut so as to give rise to at least one hierarchical contour cut that is perpendicular to the contour cut, the hierarchical contour cut optionally crossing the contour cut.

Embodiment 38. The method of any one of claims 34-37, further comprising forming a plurality of contour cuts intersecting a guide line, wherein none of the plurality of contour cuts are formed in adjacent contour lines that intersect the guide line.

Embodiment 39. The method of any one of claims 34-38, wherein the plurality of guide lines comprises P guide lines and wherein each of the P guide lines is offset from each of its immediately adjacent guidelines by D degrees, such that P×D=360.

Embodiment 40. The method of any one of claims 34-39, further comprising cutting through the substrate so as to give rise to an auxetic region of the substrate.

Embodiment 41. The method of any one of claims 34-40, wherein a guide line is perpendicular to a contour line at a location where the guide line intersects the contour line.

Embodiment 42. The method of any one of claims 34-41, further forming cuts through the substrate in a fractal pattern.

Embodiment 43. The method of claim 34, wherein the plurality of object planes are separated from one another, in the first shaped three-dimensional state, by the same distance in the direction Z.

Embodiment 44. The method of any one of claims 34-43, further comprising placing the substrate in the first shaped three-dimensional state.

Embodiment 45. The method of any one of claims 34-44, wherein the substrate comprises an acellular dermal matrix.

Embodiment 46. An intraoperative device, comprising: a substrate having a perimeter, and the substrate having a plurality of contour cuts formed therethrough, a contour cut being formed along at least a portion of a contour line that corresponds to a plane of a three-dimensional template projected onto the substrate, the contour cut optionally being defined between an intersection of the contour line with a first guide line and an intersection of the contour line with a second guide line that is adjacent to the first guide line, the first guide line and the second guide line optionally intersecting at a common origin point on the substrate; the contour cut being formed such that when the substrate is subjected to deformation, the substrate is capable of deformation beyond an initial state so as to achieve a first shaped three-dimensional state, the first shaped three-dimensional state defining a perimeter.

Embodiment 47. The intraoperative device of claim 46, further comprising a hierarchical contour cut that is formed so as to extend from at least one contour cut, the hierarchical contour cut optionally crossing the at least one contour cut, and the hierarchical contour cut optionally being formed perpendicular to the at least one contour cut.

Embodiment 48. The intraoperative device of any one of claims 46-47, wherein when the substrate is subjected to deformation, the substrate comprises a first region having a first stretchability and/or elasticity and/or rigidity in a direction relative to the substrate and a second region having a second stretchability and/or elasticity and/or rigidity in a direction relative to the substrate, the first stretchability and/or elasticity and/or rigidity and the second stretchability and/or elasticity and/or rigidity being different from one another.

Embodiment 49. The intraoperative device of any one of claims 46-48, wherein the substrate is characterized as bio-absorbable, bio-degradable, bio-resorbable, non-bio-absorbable, non-bio-degradable, non-bio-resorbable, or any combination thereof.

Embodiment 50. The intraoperative device of claim 49, wherein the substrate is characterized as bio-compatible.

Embodiment 51. The intraoperative device of claim 49, wherein the substrate is characterized as non-bio-absorbable.

Embodiment 52. The intraoperative device of any one of claims 46-51, wherein the first shaped three-dimensional state is configured to conform to at least a portion of a breast.

Embodiment 53. The intraoperative device of any one of claims 46-52, wherein the first shaped three-dimensional state is configured to conform to at least a portion of a breast implant.

Embodiment 54. The intraoperative device of any one of claims 46-53, wherein the substrate comprises a plurality of contour cuts intersecting a guide line, wherein none of the plurality of contour cuts are formed in adjacent contour lines along the guide line.

Embodiment 55. The intraoperative device of any one of claims 46-54, wherein the plurality of contour cuts connect intersections of a plurality of guide lines with a plurality of P guide lines and wherein each of the P guide lines is offset from each of its neighboring guide lines by D degrees such that P×D=360.

Embodiment 56. The intraoperative device of any one of claims 46-55, wherein the substrate comprises an auxetic region, the auxetic region optionally being formed such that the common origin point lies within the auxetic region.

Embodiment 57. The intraoperative device of any one of claims 46-56, wherein the substrate comprises a plurality of cuts in a fractal pattern.

Embodiment 58. The intraoperative device of any one of claims 46-57, wherein the substrate comprises an acellular dermal matrix material.

Embodiment 59. The intraoperative device of any one of claims 46-58, further comprising an implant, a prosthesis, or an autodonated tissue supported by the substrate in the substrate's first three-dimensional state.

Embodiment 60. The intraoperative device of any one of claims 46-59, further comprising an implant, a prosthesis, or an autodonated tissue contacting the substrate.

Embodiment 61. The intraoperative device of any one of claims 46-60, wherein the substrate defines an ovoid perimeter.

Embodiment 62. The intraoperative device of any one of claims 46-61, wherein the substrate defines a first coverage area bounded by the perimeter of the substrate, wherein first shaped three-dimensional state of the substrate defines a second coverage area bounded by the perimeter of the first shaped three-dimensional state of the substrate, and wherein the second coverage area is from 20 to 200% greater than the first coverage area.

Embodiment 63. The intraoperative device of claim 56, wherein the substrate defines a first coverage area bounded by the perimeter of the substrate, and wherein the auxetic area defines from about 0.1 to about 60% of the first coverage area.

Embodiment 64. The intraoperative device of claim 63, wherein the substrate defines a first coverage area bounded by the perimeter of the substrate, and wherein the auxetic area defines from about 10 to about 30% of the first coverage area.

Embodiment 65. The intraoperative device of any one of claims 46-63, wherein along a line emanating from a point on the substrate, the line crossing a plurality of contour lines, the plurality of contour lines are uniformly spaced relative to one another.

Embodiment 66. The intraoperative device of any one of claims 46-63, wherein along a line emanating from a point on the substrate, the line crossing a plurality of contour lines, the plurality of contour lines are non-uniformly spaced relative to one another.

Embodiment 67. The intraoperative device of any one of claims 46-66, wherein the substrate defines a repeating unit cell pattern of cuts, the repeating unit cell repeating circumferentially about the substrate.

Embodiment 68. The intraoperative device of any one of claims 46-67, wherein at least one contour cut comprises a non-uniform cross section.

Embodiment 69. The intraoperative device of any one of claims 46-68, wherein at least one contour cut comprises a circular region.

Embodiment 70. An intraoperative device, comprising: a substrate having a perimeter, and the substrate having at least a first plurality of contour cuts formed therethrough and a second plurality of contour cuts formed therethrough, wherein the first plurality of contour cuts lie on a first enclosed loop defined on the substrate, the first enclosed loop optionally overlaying or being symmetric with a first contour line that corresponds to a first plane of a three-dimensional template projected onto the substrate, wherein the second plurality of contour cuts lie on a second enclosed loop defined on the substrate, the second enclosed loop optionally overlaying or being symmetric with a second contour line that corresponds to a second plane of a three-dimensional template projected onto the substrate, the second enclosed loop enclosing the first enclosed loop, the first plurality of contour cuts and the second plurality of contour cuts being formed such that when the substrate is subjected to deformation, the substrate is capable of deformation beyond an initial state so as to achieve a first shaped three-dimensional state, the first shaped three-dimensional state defining a perimeter.

It should be understood that an enclosed loop need not actually be drawn or be otherwise formed or visible on the substrate. In some embodiments, the first plurality of contour cuts, if extended, would form the first enclosed loop. In some embodiments, the second plurality of contour cuts, if extended, would form the second enclosed loop. In some embodiments, the first plurality of contour cuts overlies or is symmetric with a first contour line that corresponds to a first plane of a three-dimensional template projected onto the substrate. In some embodiments, the second plurality of contour cuts overlies or is symmetric with a second contour line that corresponds to a second plane of the three-dimensional template projected onto the substrate.

By reference to non-limiting FIG. 13, contour cuts 1130*a*, 1130*b*, 1130*c*, and 1130*d* lie on contour line 1102. Put another way, if each of contour cuts 1130*a*, 1130*b*, 1130*c*, and 1130*d* were extended so as to connect to its neighbor, the result of extending contour cuts 1130*a*, 1130*b*, 1130*c*, and 1130*d* is a loop that overlies contour line 1102.

Embodiment 71. The intraoperative device of claim 70, further comprising a hierarchical contour cut that is formed so as to extend from at least one contour cut, the hierarchical contour cut optionally crossing the at least one contour cut, and the hierarchical contour cut optionally being formed perpendicular to the at least one contour cut. A hierarchical contour cut can connect two (or more) contour cuts, though this is not a rule or requirement.

Embodiment 72. The intraoperative device of any one of claims 70-71, wherein when the substrate is subjected to deformation, the substrate comprises a first region having a first stretchability and/or elasticity and/or rigidity in a direction (e.g., a direction normal to the substrate when the substrate is in flat or 2D form) relative to the substrate and a second region having a second stretchability and/or elasticity and/or rigidity in a direction relative to the substrate, the first stretchability and/or elasticity and/or rigidity and the second stretchability and/or elasticity and/or rigidity being different from one another.

Embodiment 73. The intraoperative device of any one of claims 71-72, wherein the substrate is characterized as bio-absorbable, bio-degradable, bio-resorbable, non-bio-absorbable, non-bio-degradable, non-bio-resorbable, or any combination thereof.

Embodiment 74. The intraoperative device of claim 73, wherein the substrate is characterized as bio-compatible.

Embodiment 75. The intraoperative device of claim 74, wherein the substrate is characterized as non-bio-absorbable.

Embodiment 76. The intraoperative device of any one of claims 70-75, wherein the first shaped three-dimensional state is configured to conform to at least a portion of a breast.

Embodiment 77. The intraoperative device of any one of claims 70-76, wherein the first shaped three-dimensional state is configured to conform to at least a portion of a breast implant.

Embodiment 78. The intraoperative device of any one of claims 70-77, wherein, along a line drawn from an origin point on the substrate, the line intersects the first enclosed loop and the second enclosed loop, and wherein the line does not intersect a contour cut of the first enclosed loop and a contour cut of the second enclosed loop.

Embodiment 79 The intraoperative device of any one of claims 70-78, wherein the plurality of contour cuts connect intersections of a plurality P of guide lines drawn from an origin point on the substrate, wherein each of the P guide lines is offset from each of its neighboring guide lines by D degrees such that P×D=360.

Embodiment 80. The intraoperative device of any one of claims 70-79, wherein the substrate comprises an auxetic region.

Embodiment 81. The intraoperative device of any one of claims 70-80, wherein the substrate comprises a plurality of cuts in a fractal pattern.

Embodiment 82. The intraoperative device of any one of claims 70-81, wherein the substrate comprises an acellular dermal matrix material.

Embodiment 83. The intraoperative device of any one of claims 70-82, further comprising an implant, a prosthesis, or an autodonated tissue supported by the substrate in the substrate's first three-dimensional state.

Embodiment 84. The intraoperative device of any one of claims 70-82, further comprising an implant, a prosthesis, or an autodonated tissue contacting the substrate.

Embodiment 85. The intraoperative device of any one of claims 70-84, wherein the substrate defines an ovoid perimeter.

Embodiment 86. The intraoperative device of any one of claims 70-85, wherein the substrate defines a first coverage area bounded by the perimeter of the substrate, wherein first shaped three-dimensional state of the substrate defines a second coverage area bounded by the perimeter of the first shaped three-dimensional state of the substrate, and wherein the second coverage area is from 20 to 200% greater than the first coverage area. Because a substrate according to the present disclosure can expand so as to achieve a comparatively large coverage area, a user applying the disclosed technology can effectively cover a larger implant with less substrate material. This is an important consideration when considering the cost of substrate materials, as well as the superior mechanical capabilities of the disclosed substrates.

Embodiment 87. The intraoperative device of claim 86, wherein the substrate defines a first coverage area hounded by the perimeter of the substrate, and wherein the auxetic area defines from about 0.1 to about 60% of the first coverage area.

Embodiment 88. The intraoperative device of claim 87, wherein the substrate defines a first coverage area bounded by the perimeter of the substrate, and wherein the auxetic area defines from about 10 to about 30% of the first coverage area.

Embodiment 89. The intraoperative device of any one of claims 70-88, wherein along a line emanating from a point on the substrate, the line crossing a plurality of contour lines, the plurality of contour lines are uniformly spaced relative to one another.

Embodiment 90. The intraoperative device of any one of claims 70-88, wherein along a line emanating from a point on the substrate, the line crossing a plurality of contour lines, the plurality of contour lines are non-uniformly spaced relative to one another.

Embodiment 91. The intraoperative device of any one of claims 70-90, wherein the substrate defines a repeating unit cell pattern of cuts, the repeating unit cell repeating circumferentially about the substrate.

Embodiment 92. The intraoperative device of any one of claims 70-91, wherein at least one contour cut comprises a non-uniform cross section.

Embodiment 93. The intraoperative device of any one of claims 70-92, wherein at least one contour cut comprises a circular region.

Cuts can be formed manually (e.g., by a surgeon or other care provider), but can also be formed in an automated fashion. As one example, a user can use a computer processor to assist with designing a given layout of cuts to form in a substrate, such that the cut substrate exhibits the desired characteristics (e.g., rigidity, stretchability, elasticity, and the like) in its initial 2D state and/or in its deployed 3D state. The substrate can be cut in accordance with custom parameters (e.g., parameters that are specific to a particular subject), but can also be cut in accordance with a design that is based on a sampling or two or more subjects. For example, a user might compile a library of sample dimensions based on measurements of hundreds of subjects and then create a device for a given subject based on the closest "match" in the library to that subject's dimensions.

What is claimed:

1. An intraoperative device, comprising:
a substrate having a plurality of discontinuous cuts formed therein, the plurality of discontinuous cuts being formed such that when the substrate is subjected to deformation, the substrate is capable of deformation beyond an initial state so as to achieve a first shaped three-dimensional state,
wherein the discontinuous cuts are formed such that when the substrate is in the first shaped state, the substrate comprises a first region having a first stretchability and/or elasticity and a second region having a second stretchability and/or elasticity, the first stretchability and/or elasticity and the second stretchability and/or elasticity being different from one another,
wherein the substrate is characterized as bio-compatible, and
wherein the substrate comprises an auxetic region.

2. The intraoperative device of claim 1, wherein the discontinuous cuts are formed such that when the substrate is in the first shaped state, the substrate comprises a first region having a first rigidity and a second region having a second rigidity, the first rigidity and the second rigidity being different from one another.

3. An intraoperative device, comprising:
a substrate having a perimeter, and the substrate having a plurality of contour cuts formed therethrough,
at least one contour cut being formed along at least a portion of a contour line that corresponds to a plane of a three-dimensional template projected onto the substrate,
the at least one contour cut being defined between an intersection of the contour line with a first guide line and an intersection of the contour line with a second guide line that is adjacent to the first guide line,
the first guide line and the second guide line intersecting at a common origin point on the substrate;
the contour cut being formed such that when the substrate is subjected to deformation, the substrate is capable of deformation beyond an initial state so as to achieve a first shaped three-dimensional state, the first shaped three-dimensional state defining a perimeter, and
wherein the substrate comprises an auxetic region, the auxetic region being formed such that the common origin point lies within the auxetic region.

4. The intraoperative device of claim 3, further comprising a hierarchical contour cut that is formed so as to extend from at least one contour cut, the hierarchical contour cut (a) crossing the at least one contour cut, the hierarchical contour cut, (b) being formed perpendicular to the at least one contour cut, or both (a) and (b).

5. The intraoperative device of claim 3, wherein when the substrate is subjected to deformation, the substrate comprises a first region having a first stretchability and/or elasticity and/or rigidity in a direction relative to the substrate and a second region having a second stretchability and/or elasticity and/or rigidity in a direction relative to the substrate, the first stretchability and/or elasticity and/or rigidity and the second stretchability and/or elasticity and/or rigidity being different from one another.

6. The intraoperative device claim 3, wherein the substrate is characterized as bio-absorbable, bio-degradable, bio-resorbable, non-bio-absorbable, non-bio-degradable, non-bio-resorbable, or any combination thereof.

7. The intraoperative device claim 3, wherein the first shaped three-dimensional state is configured to conform to at least a portion of a breast.

8. The intraoperative device of claim 3, wherein the first shaped three-dimensional state is configured to conform to at least a portion of a breast implant.

9. The intraoperative device of claim 3, wherein the substrate comprises a set of contour cuts intersecting a guide line, wherein none of the set of contour cuts are formed in adjacent contour lines along the guide line.

10. The intraoperative device of claim 3, wherein the plurality of contour cuts connect intersections of a plurality of guide lines with a plurality of P guide lines and wherein each of the P guide lines is offset from each of its neighboring guide lines by D degrees such that P×D=360.

11. The intraoperative device of claim 3, wherein the substrate comprises an acellular dermal matrix material.

12. The intraoperative device of claim 3, further comprising an implant, a prosthesis, or an autodonated tissue contacting the substrate.

13. The intraoperative device of claim 3, wherein the substrate defines a first coverage area bounded by the perimeter of the substrate, and wherein the auxetic area defines from about 0.1 to about 60% of the first coverage area.

14. The intraoperative device of claim 3, wherein the substrate defines a repeating unit cell pattern of cuts, the repeating unit cell repeating circumferentially about the substrate.

15. The intraoperative device of claim 3, wherein at least one contour cut comprises a non-uniform cross section.

16. An intraoperative device, comprising:
a substrate having a perimeter, and the substrate having at least a first plurality of contour cuts formed therethrough and a second plurality of contour cuts formed therethrough,
wherein the first plurality of contour cuts lie on a first enclosed loop defined on the substrate,
the first enclosed loop overlaying or being symmetric with a first contour line that corresponds to a first plane of a three-dimensional template projected onto the substrate,
wherein the second plurality of contour cuts lie on a second enclosed loop defined on the substrate,
the second enclosed loop overlaying or being symmetric with a second contour line that corresponds to a second plane of a three-dimensional template projected onto the substrate,
the second enclosed loop enclosing the first enclosed loop,
the first plurality of contour cuts and the second plurality of contour cuts being formed such that when the substrate is subjected to deformation, the substrate is capable of deformation beyond an initial state so as to achieve a first shaped three-dimensional state, the first shaped three-dimensional state defining a perimeter, and
wherein the substrate comprises an auxetic region.

17. The intraoperative device of claim 16, further comprising a hierarchical contour cut that is formed so as to extend from at least one contour cut, the hierarchical contour cut (a) crossing the at least one contour cut, (b) the hierarchical contour cut being formed perpendicular to the at least one contour cut, or both (a) and (b).

18. The intraoperative device claim 16, wherein the first shaped three-dimensional state is configured to conform to at least a portion of a breast.

19. The intraoperative device of claim 16, wherein the first shaped three-dimensional state is configured to conform to at least a portion of a breast implant.

* * * * *

UNITED STATES PATENT AND TRADEMARK OFFICE
CERTIFICATE OF CORRECTION

| | |
|---|---|
| PATENT NO. | : 11,642,215 B2 |
| APPLICATION NO. | : 16/967909 |
| DATED | : May 9, 2023 |
| INVENTOR(S) | : Shu Yang et al. |

It is certified that error appears in the above-identified patent and that said Letters Patent is hereby corrected as shown below:

In the Specification

Under Column No. 4, Line no. 12, Replace:
"3D and"
With:
--3D form and--

Under Column No. 4, Line no. 53, Replace:
"anatomic position)"
With:
--anatomic position);--

Under Column No. 4, Line no. 59, Replace:
"1c/1x=2"
With:
--lc/lx=2--

Under Column No. 4, Line no. 60, Replace:
"1c/1x=2.5"
With:
--lc/lx=2.5--

Under Column No. 4, Line no. 61, Replace:
"1c/1x=3"
With:
--lc/lx=3--

Under Column No. 4, Line no. 63, Replace:
"1c/1x=2"

Signed and Sealed this
Thirty-first Day of October, 2023

Katherine Kelly Vidal
*Director of the United States Patent and Trademark Office*

With:
--lc/lx=2--

Under Column No. 4, Line no. 64, Replace:
"1c/1x=2.5"
With:
--lc/lx=2.5--

Under Column No. 4, Line no. 64, Replace:
"1c/1x=3"
With:
--lc/lx=3--

Under Column No. 5, Lines nos. 34-35, Replace:
"disclosed technology"
With:
--disclosed technology.--

Under Column No. 6, Line no. 35, Replace:
"revisions and complications)"
With:
--revisions and complications).--

Under Column No. 8, Line nos. 29-30, Replace:
"traditional methods"
With:
--traditional methods.--

Under Column No. 11, Line no. 64, Replace:
"Parameter 1c can"
With:
--Parameter lc can--

Under Column No. 11, Line no. 66, Replace:
"parameter 1x can"
With:
--parameter lx can--

Under Column No. 12, Line no. 1, Replace:
"and 1y can"
With:
--and ly can--

Under Column No. 12, Line no. 2, Replace:
"(1x, 1y, and 1c can"

With:
--(lx, ly, and lc can--

Under Column No. 12, Line no. 5, Replace:
"1c/1y can be"
With:
--lc/ly can be--

Under Column No. 12, Line no. 9, Replace:
"1c/1x can be"
With:
--lc/lx can be--

Under Column No. 12, Line no. 31, Replace:
"1c/1x=2"
With:
--lc/lx=2--

Under Column No. 12, Line no. 32, Replace:
"1c/1x=2.5"
With:
--lc/lx=2.5--

Under Column No. 12, Line no. 33, Replace:
"1c/1x=3"
With:
--lc/lx=3--

Under Column No. 12, Line nos. 35-36, Replace:
"1c/1y and 1c/1x decreased."
With:
--lc/ly and lc/lx decreased.--

Under Column No. 12, Line no. 38, Replace:
"1c/1x=2"
With:
--lc/lx=2--

Under Column No. 12, Line no. 39, Replace:
"1c/1x=2.5"
With:
--lc/lx=2.5--

Under Column No. 12, Line no. 39, Replace:
"1c/1x=3"

With:
--lc/lx=3--

Under Column No. 12, Line no. 41, Replace:
"1c/1y and 1c/1x decreased."
With:
--lc/ly and lc/lx decreased.--

Under Column No. 12, Line no. 43, Replace:
"(1c/1x or 1c/1y)"
With:
--(lc/lx or lc/ly)--

Under Column No. 12, Line no. 46, Replace:
"1c/1y and 1c/1x"
With:
--lc/ly and lc/lx--

Under Column No. 12, Line nos. 58-59, Replace:
"1c/1x and 1c/1y values."
With:
--lc/lx and lc/ly values.--

Under Column No. 13, Line no. 2, Replace:
"1c/1y and 1c/1x values,"
With:
--lc/ly and lc/lx values,--

Under Column No. 13, Line no. 13, Replace:
"1c/1y and 1c/1x values,"
With:
--lc/ly and lc/lx values,--

Under Column No. 13, Line no. 24, Replace:
"1c/1y and 1c/1x values,"
With:
--lc/ly and lc/lx values,--

Under Column No. 15, Line no. 2, Replace:
"(i.e., "starting""
With:
--(i.e., a "starting"--

Under Column No. 18, Line no. 1, Replace:
"device and/or"

With:
--device (and/or--

Under Column No. 18, Line no. 56, Replace:
"initial state defining"
With:
--initial state; defining--

In the Claims

Under Column No. 24, Claim 6, Line no. 61, Replace:
"device claim"
With:
--device of claim--

Under Column No. 24, Claim 7, Line no. 65, Replace:
"device claim"
With:
--device of claim--

Under Column No. 26, Claim 18, Line no. 28, Replace:
"device claim"
With:
--device of claim--